(12) United States Patent
Bazhina et al.

(10) Patent No.: US 8,247,425 B2
(45) Date of Patent: Aug. 21, 2012

(54) PERIPHERAL OPIOID RECEPTOR ANTAGONISTS AND USES THEREOF

(75) Inventors: Nataliya Bazhina, Tappan, NY (US); George Joseph Donato, III, Swarthmore, PA (US); Steven R. Fabian, Barnegat, NJ (US); John Lokhnauth, Fair Lawn, NJ (US); Sreenivasulu Megati, New City, NY (US); Charles Melucci, Highland Mills, NY (US); Christian Ofslager, Newburgh, NY (US); Niketa Patel, Lincoln Park, NJ (US); Galen Radebaugh, Chester, NJ (US); Syed M. Shah, East Hanover, NJ (US); Jan Szeliga, Croton on Hudson, NY (US); Huyi Zhang, Garnerville, NY (US); Tianmin Zhu, Monroe, NY (US)

(73) Assignee: Wyeth, Madison, NJ (US)

( * ) Notice: Subject to any disclaimer, the term of this patent is extended or adjusted under 35 U.S.C. 154(b) by 457 days.

(21) Appl. No.: 12/570,891

(22) Filed: Sep. 30, 2009

(65) Prior Publication Data

US 2010/0120813 A1 May 13, 2010

Related U.S. Application Data

(60) Provisional application No. 61/237,428, filed on Aug. 27, 2009, provisional application No. 61/226,581, filed on Jul. 17, 2009, provisional application No. 61/101,201, filed on Sep. 30, 2008.

(51) Int. Cl.
A61K 31/485 (2006.01)
A61K 31/4748 (2006.01)

(52) U.S. Cl. .............................. 514/282; 514/289
(58) Field of Classification Search ............... 514/282, 514/289
See application file for complete search history.

(56) References Cited

U.S. PATENT DOCUMENTS

| | | | |
|---|---|---|---|
| 3,714,159 A | 1/1973 | Janssen et al. |
| 3,723,440 A | 3/1973 | Freter et al. |
| 3,854,480 A | 12/1974 | Zaffaroni |
| 3,884,916 A | 5/1975 | Janssen et al. |
| 3,937,801 A | 2/1976 | Lippmann |
| 3,996,214 A | 12/1976 | Dajani et al. |
| 4,012,393 A | 3/1977 | Markos et al. |
| 4,013,668 A | 3/1977 | Adelstein et al. |
| 4,025,652 A | 5/1977 | Diamond et al. |
| 4,060,635 A | 11/1977 | Diamond et al. |
| 4,066,654 A | 1/1978 | Adelstein et al. |
| 4,069,223 A | 1/1978 | Adelstein |
| 4,072,686 A | 2/1978 | Adelstein et al. |
| 4,115,400 A | 9/1978 | Zimmerman |
| 4,115,564 A | 9/1978 | Diamond et al. |
| 4,116,963 A | 9/1978 | Adelstein |
| 4,125,531 A | 11/1978 | Yen |
| 4,176,186 A | 11/1979 | Goldberg et al. |
| 4,194,045 A | 3/1980 | Adelstein |
| 4,203,920 A | 5/1980 | Diamond et al. |
| 4,241,066 A | 12/1980 | Kobylecki et al. |
| 4,277,605 A | 7/1981 | Buyniski et al. |
| 4,311,833 A | 1/1982 | Namikoshi et al. |
| 4,322,426 A | 3/1982 | Hermann et al. |
| 4,326,074 A | 4/1982 | Diamond et al. |
| 4,326,075 A | 4/1982 | Diamond et al. |
| 4,377,568 A | 3/1983 | Chopra et al. |
| 4,385,078 A | 5/1983 | Onda et al. |
| 4,427,676 A | 1/1984 | White et al. |
| 4,430,327 A | 2/1984 | frederickson et al. |
| 4,452,775 A | 6/1984 | Kent |
| 4,457,907 A | 7/1984 | Porter et al. |
| 4,462,839 A | 7/1984 | McGinley et al. |
| 4,466,968 A | 8/1984 | Bernstein |
| 4,518,433 A | 5/1985 | McGinley et al. |
| 4,533,739 A | 8/1985 | Pitzele et al. |
| 4,556,552 A | 12/1985 | Porter et al. |
| 4,606,909 A | 8/1986 | Bechgaard et al. |
| 4,615,885 A | 10/1986 | Nakagame et al. |
| 4,670,287 A | 6/1987 | Tsuji et al. |

(Continued)

FOREIGN PATENT DOCUMENTS

AU 610 561 8/1988

(Continued)

OTHER PUBLICATIONS

[No Author Listed] Extracolonic Motility Abnormalities. Persistence of Abdominal Symptoms after Successful Surgery from Southern Medical Journal. 2002;95(9);1042-1046. http://www.medscape.com/viewarticle/442893_4, 2 pages.
[No Author Listed] Pathophysiology. Medscape General Medicine. 2005;7(3):17 http://www.medscape.com/viewarticle/506798_5, 3 pages.
[No Author Listed] Methylnaltrexone: MNTX. Drugs R D. 2006;7(6):374-8.
[No Author Listed] Oncology. 1996;10(12):1880.
[No Author Listed] Progenics achieves enrollment target in pivotal phase 3 clinical trial of methylnaltrexone for opioid-induced constipation. Press Release. Progenics Pharmaceuticals, Inc. Dec. 3, 2004.

(Continued)

Primary Examiner — Charanjit Aulakh
(74) Attorney, Agent, or Firm — McCarter & English, LLP; Jonathan M. Sparks; Maneesh Gulati, Esq.

(57) ABSTRACT

The present invention provides a compound of formula I:

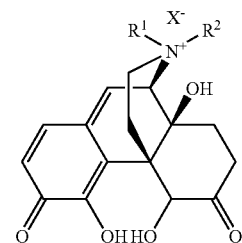

wherein $X^-$, $R^1$, and $R^2$ are as defined herein, and compositions thereof.

50 Claims, 15 Drawing Sheets

U.S. PATENT DOCUMENTS

| | | |
|---|---|---|
| 4,675,189 A | 6/1987 | Kent et al. |
| 4,689,332 A | 8/1987 | McLaughlin et al. |
| 4,719,215 A | 1/1988 | Goldberg |
| 4,730,048 A | 3/1988 | Portoghese |
| 4,765,978 A | 8/1988 | Abidi et al. |
| 4,806,556 A | 2/1989 | Portoghese |
| 4,824,853 A | 4/1989 | Wals et al. |
| 4,836,212 A | 6/1989 | Schmitt et al. |
| 4,837,214 A | 6/1989 | Tanaka et al. |
| 4,857,533 A | 8/1989 | Sherman et al. |
| 4,861,781 A | 8/1989 | Goldberg |
| 4,863,928 A | 9/1989 | Atkinson et al. |
| 4,867,979 A | 9/1989 | Sheth et al. |
| 4,870,084 A | 9/1989 | Eggler et al. |
| 4,888,346 A | 12/1989 | Bihari et al. |
| 4,891,379 A | 1/1990 | Zimmerman et al. |
| 4,912,114 A | 3/1990 | Revesz |
| 4,965,269 A | 10/1990 | Brändström et al. |
| 4,987,136 A | 1/1991 | Kreek et al. |
| 4,990,521 A | 2/1991 | Van Daele et al. |
| 4,999,342 A | 3/1991 | Ahmad et al. |
| 5,102,887 A | 4/1992 | Goldberg |
| 5,116,868 A | 5/1992 | Chen et al. |
| 5,133,974 A | 7/1992 | Paradissis et al. |
| 5,159,081 A | 10/1992 | Cantrell et al. |
| 5,202,159 A | 4/1993 | Chen et al. |
| 5,220,017 A | 6/1993 | Bock et al. |
| 5,236,947 A | 8/1993 | Calvet et al. |
| 5,250,542 A | 10/1993 | Cantrell et al. |
| 5,256,154 A | 10/1993 | Liebert et al. |
| 5,270,328 A | 12/1993 | Cantrell et al. |
| 5,312,899 A | 5/1994 | Schiller |
| 5,391,372 A | 2/1995 | Campbell |
| 5,407,686 A | 4/1995 | Patel et al. |
| 5,426,112 A | 6/1995 | Zagon et al. |
| 5,434,171 A | 7/1995 | Frank et al. |
| 5,472,943 A | 12/1995 | Crain et al. |
| 5,512,578 A | 4/1996 | Crain et al. |
| 5,536,507 A | 7/1996 | Abramowitz et al. |
| 5,567,423 A | 10/1996 | Ying et al. |
| 5,585,348 A | 12/1996 | Crain et al. |
| 5,591,433 A | 1/1997 | Michael et al. |
| 5,597,564 A | 1/1997 | Ying et al. |
| 5,609,871 A | 3/1997 | Michael et al. |
| 5,614,219 A | 3/1997 | Wunderlich et al. |
| 5,614,222 A | 3/1997 | Kaplan et al. |
| 5,626,875 A | 5/1997 | Ballester Rodes et al. |
| 5,629,001 A | 5/1997 | Michael et al. |
| 5,656,290 A | 8/1997 | Kelm et al. |
| 5,686,072 A | 11/1997 | Uhr et al. |
| 5,714,586 A | 2/1998 | Kunstmann et al. |
| 5,739,152 A | 4/1998 | Andersson et al. |
| 5,767,125 A | 6/1998 | Crain et al. |
| 5,804,595 A | 9/1998 | Portoghese et al. |
| 5,811,451 A | 9/1998 | Minoia et al. |
| 5,821,219 A | 10/1998 | Grandy et al. |
| 5,866,154 A | 2/1999 | Bahal et al. |
| 5,866,164 A | 2/1999 | Kuczynski et al. |
| 5,958,452 A | 9/1999 | Oshlack et al. |
| 5,972,954 A | 10/1999 | Foss et al. |
| 5,981,185 A | 11/1999 | Matson et al. |
| RE36,547 E | 2/2000 | Crain et al. |
| 6,025,154 A | 2/2000 | Li et al. |
| 6,096,756 A | 8/2000 | Crain et al. |
| 6,096,763 A | 8/2000 | Hoffman et al. |
| 6,096,764 A | 8/2000 | Bryant et al. |
| 6,099,853 A | 8/2000 | Hertelendy et al. |
| 6,136,780 A | 10/2000 | Zagon et al. |
| 6,153,620 A | 11/2000 | Kornetsky |
| 6,190,691 B1 | 2/2001 | Mak |
| 6,194,382 B1 | 2/2001 | Crain et al. |
| 6,261,599 B1 | 7/2001 | Oshlack et al. |
| 6,274,591 B1 | 8/2001 | Foss et al. |
| 6,277,384 B1 | 8/2001 | Kaiko et al. |
| 6,353,004 B1 | 3/2002 | Farrar et al. |
| 6,359,111 B1 | 3/2002 | Meyer et al. |
| 6,362,194 B1 | 3/2002 | Crain et al. |
| 6,384,044 B1 | 5/2002 | Bihari |
| 6,395,705 B2 | 5/2002 | Crain et al. |
| 6,419,959 B1 | 7/2002 | Walter et al. |
| 6,426,094 B2 | 7/2002 | Piver et al. |
| 6,451,806 B2 | 9/2002 | Farrar |
| 6,455,537 B1 | 9/2002 | Cooper |
| 6,469,030 B2 | 10/2002 | Farrar et al. |
| 6,479,500 B1 | 11/2002 | Fukushima et al. |
| 6,559,158 B1 | 5/2003 | Foss et al. |
| 6,608,075 B2 | 8/2003 | Foss et al. |
| 6,693,125 B2 | 2/2004 | Borisy et al. |
| 6,696,066 B2 | 2/2004 | Kaiko et al. |
| 6,720,336 B2 | 4/2004 | Liras |
| 6,723,712 B2 | 4/2004 | Bourhis et al. |
| 6,734,188 B1 | 5/2004 | Rhodes et al. |
| 6,756,364 B2 | 6/2004 | Barbier et al. |
| 6,777,534 B1 | 8/2004 | Klagsbrun et al. |
| 6,794,370 B2 | 9/2004 | Achterrath |
| 6,800,639 B2 | 10/2004 | Giles et al. |
| 6,833,349 B2 | 12/2004 | Xia et al. |
| 6,838,469 B2 | 1/2005 | Sumegi |
| 6,884,879 B1 | 4/2005 | Baca et al. |
| 6,900,234 B1 | 5/2005 | Fossa |
| 6,946,556 B1 | 9/2005 | Likhotvorik et al. |
| 6,960,596 B2 | 11/2005 | Bissery |
| 6,967,016 B2 | 11/2005 | van Gemen et al. |
| 6,984,403 B2 | 1/2006 | Hagen et al. |
| 6,986,901 B2 | 1/2006 | Meisel et al. |
| 6,989,383 B1 | 1/2006 | Rosen et al. |
| 6,992,106 B2 | 1/2006 | Morinaga et al. |
| 7,012,100 B1 | 3/2006 | Edwards et al. |
| 7,074,825 B2 | 7/2006 | Mo et al. |
| 7,094,775 B2 | 8/2006 | Strugnell et al. |
| 7,129,265 B2 | 10/2006 | Mason |
| 7,132,554 B2 | 11/2006 | Rose |
| 7,141,554 B2 | 11/2006 | Rochat et al. |
| 7,160,913 B2 | 1/2007 | Schneider |
| 7,183,269 B2 | 2/2007 | Kreutz |
| 7,196,115 B2 | 3/2007 | Khanuja et al. |
| 7,259,233 B2 | 8/2007 | Dodd et al. |
| 7,501,434 B2 | 3/2009 | Shah et al. |
| 7,563,899 B2 | 7/2009 | Boyd et al. |
| 7,674,904 B2 | 3/2010 | Doshan et al. |
| 2001/0010919 A1 | 8/2001 | Grandy et al. |
| 2001/0018413 A1 | 8/2001 | Crain et al. |
| 2001/0033865 A1 | 10/2001 | Oshlack et al. |
| 2001/0036469 A1 | 11/2001 | Gooberman |
| 2001/0036476 A1 | 11/2001 | Oshlack et al. |
| 2001/0036951 A1 | 11/2001 | Farrar et al. |
| 2001/0046968 A1 | 11/2001 | Zagon et al. |
| 2001/0047005 A1 | 11/2001 | Farrar et al. |
| 2002/0028825 A1 | 3/2002 | Foss et al. |
| 2002/0064771 A1 | 5/2002 | Zhong et al. |
| 2002/0068712 A1 | 6/2002 | Stevens |
| 2002/0173466 A1 | 11/2002 | Crain et al. |
| 2002/0176888 A1 | 11/2002 | Bartholomaeus et al. |
| 2002/0188005 A1 | 12/2002 | Farrar et al. |
| 2003/0022909 A1 | 1/2003 | Moss et al. |
| 2003/0026801 A1 | 2/2003 | Weiner et al. |
| 2003/0039689 A1 | 2/2003 | Chen et al. |
| 2003/0065003 A1 | 4/2003 | Foss et al. |
| 2003/0105121 A1 | 6/2003 | Bihari |
| 2003/0124086 A1 | 7/2003 | Bentley et al. |
| 2003/0144312 A1 | 7/2003 | Schoenhard |
| 2003/0158220 A1 | 8/2003 | Foss et al. |
| 2003/0187010 A1 | 10/2003 | Foss et al. |
| 2003/0191147 A1 | 10/2003 | Sherman et al. |
| 2003/0219406 A1 | 11/2003 | Schroit et al. |
| 2004/0010996 A1 | 1/2004 | Karlstrom et al. |
| 2004/0010997 A1 | 1/2004 | Close |
| 2004/0010998 A1 | 1/2004 | Turco |
| 2004/0024006 A1 | 2/2004 | Simon |
| 2004/0136908 A1 | 7/2004 | Olson et al. |
| 2004/0162306 A1 | 8/2004 | Foss et al. |
| 2004/0162307 A1 | 8/2004 | Foss et al. |
| 2004/0162308 A1 | 8/2004 | Foss et al. |
| 2004/0167147 A1 | 8/2004 | Foss et al. |
| 2004/0167148 A1 | 8/2004 | Foss et al. |
| 2004/0180916 A1 | 9/2004 | Levine |
| 2004/0242523 A1 | 12/2004 | Weichselbaum et al. |

| | | | |
|---|---|---|---|
| 2004/0254156 A1 | 12/2004 | Le Bourdonnec et al. |
| 2004/0254208 A1 | 12/2004 | Weber et al. |
| 2004/0259898 A1 | 12/2004 | Moss et al. |
| 2004/0259899 A1 | 12/2004 | Sanghvi et al. |
| 2004/0266806 A1 | 12/2004 | Sanghvi et al. |
| 2005/0004029 A1 | 1/2005 | Garcia |
| 2005/0004155 A1 | 1/2005 | Boyd et al. |
| 2005/0011468 A1 | 1/2005 | Moss et al. |
| 2005/0048117 A1 | 3/2005 | Foss et al. |
| 2005/0085514 A1 | 4/2005 | Cosford et al. |
| 2005/0124657 A1 | 6/2005 | Christ et al. |
| 2005/0124885 A1 | 6/2005 | Abend et al. |
| 2005/0187255 A1 | 8/2005 | Lee et al. |
| 2006/0025592 A1 | 2/2006 | Stranix et al. |
| 2006/0063792 A1 | 3/2006 | Dolle et al. |
| 2006/0094658 A1 | 5/2006 | Currie et al. |
| 2006/0115424 A1 | 6/2006 | Gray et al. |
| 2006/0128742 A1 | 6/2006 | Edwards et al. |
| 2006/0204512 A1 | 9/2006 | Krasnoperov et al. |
| 2006/0205753 A1 | 9/2006 | Israel |
| 2006/0258696 A1 | 11/2006 | Moss et al. |
| 2007/0010450 A1 | 1/2007 | Currie et al. |
| 2007/0020261 A1 | 1/2007 | Sliwkowski et al. |
| 2007/0060501 A1 | 3/2007 | Jhamandas et al. |
| 2007/0071761 A1 | 3/2007 | Seon |
| 2007/0082044 A1 | 4/2007 | Yeum |
| 2007/0099946 A1 | 5/2007 | Doshan et al. |
| 2007/0265293 A1 | 11/2007 | Boyd et al. |
| 2008/0064743 A1 | 3/2008 | Shah et al. |
| 2008/0064744 A1 | 3/2008 | Shah et al. |
| 2008/0070975 A1 | 3/2008 | Shah et al. |
| 2008/0075771 A1 | 3/2008 | Vaughn et al. |
| 2008/0103438 A1 | 5/2008 | Prais et al. |
| 2008/0194611 A1 | 8/2008 | Alverdy et al. |
| 2008/0274119 A1 | 11/2008 | Moss et al. |
| 2009/0312359 A1 | 12/2009 | Foss et al. |
| 2010/0087472 A1 | 4/2010 | Foss et al. |
| 2010/0099699 A1 | 4/2010 | Melucci et al. |
| 2010/0105911 A1 | 4/2010 | Wagoner et al. |
| 2010/0249169 A1 | 9/2010 | Shah et al. |

FOREIGN PATENT DOCUMENTS

| | | |
|---|---|---|
| AU | 758 416 B2 | 7/1999 |
| AU | 2003204844 B2 | 9/2007 |
| BE | 876 968 A1 | 10/1979 |
| CA | 2 064 373 A1 | 9/1992 |
| CA | 1 315 689 | 4/1993 |
| CA | 2 312 234 | 5/1999 |
| DE | 3 780 819 T2 | 1/1993 |
| DE | 4 303 214 A1 | 8/1994 |
| DE | 196 51 551 A1 | 6/1998 |
| EP | 0 278 821 A1 | 8/1988 |
| EP | 0 289 070 A1 | 11/1988 |
| EP | 0 306 575 B1 | 3/1989 |
| EP | 0 352 361 A1 | 1/1990 |
| EP | 0 506 468 A1 | 9/1992 |
| EP | 0 643 967 A2 | 3/1995 |
| EP | 0 663 401 A1 | 7/1995 |
| EP | 0 760 661 B1 | 12/1998 |
| EP | 0 984 004 A2 | 3/2000 |
| EP | 1 047 726 B1 | 8/2002 |
| ES | 2226933 T3 | 4/2005 |
| GB | 1 202 148 | 8/1970 |
| JP | 1 068 376 A | 3/1989 |
| JP | 2-25427 | 1/1990 |
| JP | 4-183371 | 6/1992 |
| JP | 4-225922 A | 8/1992 |
| JP | 5-213763 A | 8/1993 |
| JP | 2 625 457 B2 | 7/1997 |
| JP | 4-217924 B2 | 2/2009 |
| NZ | 222911 | 12/1987 |
| SG | 116167 | 1/2008 |
| WO | WO 83/03197 A1 | 9/1983 |
| WO | WO 88/05297 A1 | 7/1988 |
| WO | WO 93/20826 A1 | 10/1993 |
| WO | WO 94/10202 A1 | 5/1994 |
| WO | WO 95/31985 A2 | 11/1995 |
| WO | WO 96/14058 A1 | 5/1996 |
| WO | WO 96/23793 A1 | 8/1996 |
| WO | WO 97/07118 A1 | 2/1997 |
| WO | WO 97/29739 A2 | 8/1997 |
| WO | WO 97/33566 A2 | 9/1997 |
| WO | WO 98/25613 A2 | 6/1998 |
| WO | WO 99/22737 A1 | 5/1999 |
| WO | WO 99/36470 A1 | 7/1999 |
| WO | WO 99/40089 A1 | 8/1999 |
| WO | WO 01/13909 A2 | 3/2001 |
| WO | WO 01/32180 A2 | 5/2001 |
| WO | WO 01/37785 A2 | 5/2001 |
| WO | WO 01/41705 A2 | 6/2001 |
| WO | WO 01/42207 A2 | 6/2001 |
| WO | WO 01/70031 A1 | 9/2001 |
| WO | WO 01/85257 A2 | 11/2001 |
| WO | WO 02/060870 A2 | 8/2002 |
| WO | WO 02/098422 A1 | 12/2002 |
| WO | WO 03/020296 A1 | 3/2003 |
| WO | WO 03/032990 A2 | 4/2003 |
| WO | WO 03/037340 A1 | 5/2003 |
| WO | WO 03/077867 A2 | 9/2003 |
| WO | WO 2004/014291 A2 | 2/2004 |
| WO | WO 2004/043964 A2 | 5/2004 |
| WO | WO 2004/080996 A1 | 9/2004 |
| WO | WO 2004/091623 A1 | 10/2004 |
| WO | WO 2006/096626 A2 | 9/2006 |
| WO | WO 2006/127898 A2 | 11/2006 |
| WO | WO 2006/127899 A2 | 11/2006 |
| WO | WO 2006/132963 A2 | 12/2006 |
| WO | WO 2006/135650 A1 | 12/2006 |
| WO | WO 2007/053194 A2 | 5/2007 |
| WO | WO 2007/053698 A2 | 5/2007 |
| WO | WO 2007/131154 A2 | 11/2007 |
| WO | WO 2008/016704 A1 | 2/2008 |
| WO | WO 2008/019115 A2 | 2/2008 |
| WO | WO 2008/064150 A1 | 5/2008 |
| WO | WO 2008/064351 A2 | 5/2008 |
| WO | WO 2008/064353 A2 | 5/2008 |
| WO | WO 2008/070462 A2 | 6/2008 |
| WO | WO 2008/121348 A2 | 10/2008 |
| WO | WO 2008/121860 A1 | 10/2008 |

OTHER PUBLICATIONS

[No Author Listed] Progenics announces positive top-line results from pivotal phase 3 clinical trial of MNTX in opioid-induced constipation. Pre0ss Release. Progenics Pharmaceuticals, Inc. Mar. 10, 2005.

[No Author Listed] Progenics initiates second phase 3 clinical trial of methylnaltrexone in opioid-induced constipation. Press Release. Progenics Pharmaceuticals, Inc. Jan. 13, 2004.

[No Author Listed] Remington's Pharmaceutical Sciences. 15th Edition. 1995:1614-5.

[No Author Listed] Remington's Pharmaceutical Sciences. 15th Edition. 1995:201-02.

[No Author Listed] Remington's Pharmaceutical Sciences. 15th Edition. 1995:273-74.

[No Author Listed] Remington's Pharmaceutical Sciences. 15th Edition. 1995:1466.

[No Author Listed] The Merck Manual. 17th edition. 1999:312-315.

Akinbami et al., Effect of a peripheral and a central acting opioid antagonist on the testicular response to stress in rats. Neuroendocrinology. Apr. 1994;59(4):343-8.

Altier et al., Opioid receptors in the ventral tegmental area contribute to stress-induced analgesia in the formalin test for tonic pain. Brain Res. Apr. 29, 1996;718(1-2):203-6.

Amin et al., Efficacy of methylnaltrexone versus naloxone for reversal of morphine-induced depression of hypoxic ventilatory response. Anesth Analg. Apr. 1994;78(4):701-5.

Amir et al., Endorphins in endotoxin-induced hyperglycemia in mice. Arch Toxicol Suppl. 1983;6:261-5.

Amir, Naloxone improves, and morphine exacerbates, experimental shock induced by release of endogenous histamine by compound 48/80. Brain Res. Apr. 9, 1984;297(1):187-90.

Arendt et al., Bidirectional effects of endogenous opioid peptides on endothelin release rates in porcine aortic endothelial cell culture: mediation by delta opioid receptor and opioid receptor antagonist-insensitive mechanisms. J Pharmacol Exp Ther. Jan. 1995;272(1):1-7.

Arerangaiah et al., Opioids induce renal abnormalities in tumor-bearing mice. Nephron Exp Nephrol. 2007;105(3):e80-9. Epub Jan. 12, 2007.

Argentieri et al., Interaction of the opiate antagonist, naltrexone methyl bromide, with the acetylcholine receptor system of the motor end-plate. Brain Res. Oct. 31, 1983;277(2):377-9.

Armstead, Relationship among NO, the KATP channel, and opioids in hypoxic pial artery dilation. Am J Physiol. Sep. 1998;275(3 Pt 2):H988-94.

Armstrong et al., The gastrointestinal activity and peripheral selectivity of alvimopan, ADL08-0011, and naloxone in mice. May 21, 2006 DDW Presentation in Los Angeles. Clincial Phar Therap. 2005;77:74. Abstract #221957.

Attali et al., Kappa opiate agonists inhibit Ca2+ influx in rat spinal cord-dorsal root ganglion cocultures. Involvement of a GTP-binding protein. J Biol Chem. Jan. 5, 1989;264(1):347-53.

Aung et al., Methylnaltrexone prevents morphine-induced kaolin intake in the rat. Life Sci. Apr. 16, 2004;74(22):2685-91.

Aung et al., Scutellaria baicalensis decreases ritonavir-induced nausea. AIDS Res Ther. Dec. 20, 2005;2:12.

Bagnol et al., Changes in enkephalin immunoreactivity of sympathetic ganglia and digestive tract of the cat after splanchnic nerve ligation. Regul Pept. Sep. 22, 1993;47(3):259-73. Abstract only.

Baker et al., Functional effects of systemically administered agonists and antagonists of mu, delta, and kappa opioid receptor subtypes on body temperature in mice. J Pharmacol Exp Ther. Sep. 2002;302(3):1253-64.

Balasubramanian et al., Morphine sulfate inhibits hypoxia-induced vascular endothelial growth factor expression in endothelial cells and cardiac myocytes. J Mol Cell Cardiol. Dec. 2001;33(12):2179-87.

Baratti et al., Brain opioid peptides may participate in the reversal of pentylenetetrazol-induced amnesia. Methods Find Exp Clin Pharmacol. Sep. 1990;12(7):451-6.

Basilisco et al., Oral naloxone antagonizes loperamide-induced delay of orocecal transit. Dig Dis Sci. Aug. 1987;32(8):829-32.

Basilisco et al., Effect of loperamide and naloxone on mouth-to-caecum transit time evaluated by lactulose hydrogen breath test. Gut. Jul. 1985;26(7):700-3.

Bedingfield et al., Methylnaltrexone attenuates taste aversion conditioned by low-dose ethanol. Alcohol. Jan. 1998;15(1):51-4.

Belcheva et al,.μ-Opioid receptor-mediated ERK activation involves calmodulin-dependent epidermal growth factor receptor transactivation. J Biol Chem. Sep. 7, 2001;276(36):33847-53. Epub Jul. 16, 2001.

Belcheva et al., μopioid transactivation and down-regulation of the epidermal growth factor receptor in astrocytes: implications for mitogen-activated protein kinase signaling. Mol Pharmacol. Dec. 2003;64(6):1391-401.

Bianchetti et al., Quaternary derivatives of narcotic antagonists: stereochemical requirements at the chiral nitrogen for in vitro and in vivo activity. Life Sci. 1983;33 Suppl 1:415-8.

Bianchi et al., Quaternary narcotic antagonists' relative ability to prevent antinociception and gastrointestinal transit inhibition in morphine-treated rats as an index of peripheral selectivity. Life Sci. May 31, 1982;30(22):1875-83.

Bickel, Stimulation of colonic motility in dogs and rats by an enkephalin analogue pentapeptide. Life Sci. 1983;33 Suppl 1:469-72.

Bigliardi et al., Different expression of mu-opiate receptor in chronic and acute wounds and the effect of beta-endorphin on transforming growth factor beta type II receptor and cytokeratin 16 expression. J Invest Dermatol. Jan. 2003;120(1):145-52.

Bigliardi-Qi et al., Changes of epidermal mu-opiate receptor expression and nerve endings in chronic atopic dermatitis. Dermatology. 2005;210(2):91-9.

Binder et al., Effect of the peripherally selective kappa-opioid agonist, asimadoline, on adjuvant arthritis. Br J Pharmacol. Jun. 1998;124(4):647-54.

Blank et al., Central, stereoselective receptors mediate the acute effects of opiate antagonists on luteinizing hormone secretion. Life Sci. Oct. 27, 1986;39(17):1493-99.

Blebea et al., Differential effects of vascular growth factors on arterial and venous angiogenesis. J Vasc Surg. Mar. 2002;35(3):532-8.

Blebea et al., Opioid growth factor modulates angiogenesis. J Vasc Surg. Aug. 2000;32(2):364-73.

Bond et al., Investigation of small bowel transit time in man utilizing pulmonary hydrogen (H2) measurements. J Lab Clin Med. Apr. 1975;85(4):546-55. Abstract Only.

Bonn, Morphine stimulates tumour growth. Lancet Oncol. Sep. 2002;3(9):520.

Boonstra et al., Engineering novel biocatalytic routes for production of semisynthetic opiate drugs. Biomol Eng. Sep. 2001;18(2):41-7.

Bös et al., A Short and Efficient Synthesis of C-Nor-Dihydrocodeinone—The Antipode of Goto's Sinomenilone. Heterocycles. 1983;20(6):1077-81.

Bowen et al., Antagonism of the antinociceptive and discriminative stimulus effects of heroin and morphine by 3-methoxynaltrexone and naltrexone in rhesus monkeys. J Pharmacol Exp Ther. Jul. 2002;302(1):264-73.

Bowen et al., College on Problems of Drug Dependence 64th Annual Scientific Meeting. Jun. 8-13, 2002. Quebec City, Quebec, Canada. Abstracts. Drug Alcohol Depend. May 1, 2002;66 Suppl 1:S1-220. Abstract No. 65.

Breitbart et al., Control of non-pain symptoms in HIV/AIDS. J Back Musculoskelet Rehabil. 1997;8(3):243-46.

Brix-Christensen et al., Endogenous morphine is produced in response to cardiopulmonary bypass in neonatal pigs. Acta Anaesthesiol Scand. Nov. 2000;44(10):1204-8.

Brix-Christensen et al., Endogenous morphine levels increase following cardiac surgery as part of the nti-inflammatory response? Int J Cardiol. Dec. 19, 1997;62(3):191-7.

Brondsted et al., Hydrogels for site-specific drug delivery to the colon: in vitro and in vivo degradation. Pharm Res. Dec. 1992;9(12):1540-5. Abstract Only.

Brown et al., Opiate antagonists: central sites of action in suppressing water intake of the rat. Brain Res. Sep. 28, 1981;221(2):432-6.

Brown et al., Reversal of morphine-induced catalepsy in the rat by narcotic antagonists and their quaternary derivatives. Neuropharmacology. Mar. 1983;22(3):317-21.

Brown et al., Techniques for mechanical stimulation of cells in vitro: a review. J Biomech. Jan. 2000;33(1):3-14.

Brown et al., The use of quaternary narcotic antagonists in opiate research. Neuropharmacology. Mar. 1985;24(3):181-91.

Bruce et al., Microbial degradation of the morphine alkaloids: identification of morphine as an intermediate in the metabolism of morphine by Pseudomonas putida M10. Arch Microbiol. 1990;154(5):465-70.

Bruley-Des-Varannes et aL,Cholécystokine et ses antagonistes: effets sur la motricitédigestive. Gastroenterol Clin Biol. 1991;15:744-57. French.

Bundgaard et al., (C) Means to Enhance Penetration. (1) Prodrugs as a means to improve the delivery of peptide drugs. J Drug Delivery Rev. 1992;8:1-38.

Burkhart et al., Metkephamid (Tyr-D-Ala-Gly-Phe-N(Me)Met-NH$_2$), a Potent Opioid Peptide: Receptor Binding and Analgesic Properties. Peptides. 1982;3:869-71.

Caballero-Hernandez et al, Potentiation of rat lymphocyte proliferation by novel non-peptidic synthetic opioids. Int Immunopharmacol. Jul. 2005;5(7-8):1271-8. Epub Apr. 12, 2005.

Cadet et al., Differential expression of the human mu opiate receptor from different primary vascular endothelial cells. Med Sci Monit. Oct. 2004;10(10):BR351-5. Epub Sep. 23, 2004.

Cadet at al., Molecular identification and functional expression of mu 3, a novel alternatively spliced variant of the human mu opiate receptor gene. J Immunol. May 15, 2003;170(10):5118-23.

Calcagnetti et al., Quaternary naltrexone reveals the central mediation of conditional opioid analgesia. Pharmacol Biochem Behay. Jul. 1987;27(3):529-31.

Cao et al., Cardioprotection of interleukin-2 is mediated via kappa-opioid receptors. J Pharmacol Exp Ther. May 2004;309(2):560-7. Epub Jan. 27, 2004.

Carr et al., Naltrexone antagonizes the analgesic and immunosuppressive effects of morphine in mice. J Pharmacol Exp Ther. May 1994;269(2):693-8.

Chang et al., An antiabsorptive basis for precipitated withdrawal diarrhea in morphine-dependent rats. J Pharmacol Exp Ther. Feb. 1984;228(2):364-9.

Chang et al., The association between opiates and cytokines in disease. Adv Exp Med Biol. 1998;437:4-6.

Chatterjie et al., Stereospecific synthesis of the 6beta-hydroxy metabolites of naltrexone and naloxone. J Med Chem. May 1975;18(5):490-2. Abstract Only.

Chen et al., Morphine stimulates vascular endothelial growth factor-like signaling in mouse retinal endothelial cells. Curr Neurovasc Res. Aug. 2006;3(3):171-80.

Choi et al., Opioid antagonists: a review of their role in palliative care, focusing on use in opioid-related constipation. J Pain Symptom Manage. Jul. 2002;24(1):71-90. Review.

Choi et al., Inhibition of chemokine-induced chemotaxis of monkey leukocytes by mu-opioid receptor agonists. In Vivo. Sep.-Oct. 1999;13(5):389-96.

Collins et al., Peak plasma concentrations after oral morphine: a systematic review. J Pain Symptom Manage. Dec. 1998;16(6):388-402.

Cone et al., The identification and measurement of two new metabolites of naltrexone in human urine. Res Commun Chem Pathol Pharmacol. Jun. 1978;20(3):413-33. Abstract Only.

Cozzolino et al., Acute effects of beta-endorphin on cardiovascular function in patients with mild to moderate chronic heart failure. Am Heart J. Sep. 2004;148(3):E1-7.

Culpepper-Morgan et al., Treatment of opioid-induced constipation with oral naloxone: a pilot study. Clin Pharmacol Ther. Jul. 1992;52(1):90-5. Abstract Only.

D'Amato et al., Studies of three non-peptide cholecystokinin antagonists (devazepide, lorglumide and loxiglumide) in human isolated alimentary muscle and guinea-pig ileum. Br J Pharmacol. Feb. 1991;102(2):391-5.

Dajani et al., Effects of E prostaglandins, diphenoxylate and morphine on intestinal motility in vivo. Eur J Pharmacol. Nov. 1975;34(1):105-13. Abstract Only.

Dajani et al., The pharmacology of SC-27166: a novel antidiarrheal agent. J Pharmacol Exp Ther. Dec. 1977;203(3):512-26. Abstract Only.

Daniel et al., Effects of morphine and other drugs on motility of the terminal ileum. Gastroenterology. Apr. 1959;36(4):510-23.

De Ponti et al., Methylnaltrexone Progenics. Curr Opin Investig Drugs. Apr. 2002;3(4):614-20. Review.

De Schryver et al., New developments in the treatment of irritable bowel syndrome. Scand J Gastroenterol Suppl. 2000;(232):38-42. Review.

Doherty et al., Route-dependent metabolism of morphine in the vascularly perfused rat small intestine preparation. Pharm Res. Mar. 2000;17(3):291-8.

Dragonetti et al., Levallorphan methyl iodide (SR 58002), a potent narcotic antagonist with peripheral selectivity superior to that of other quaternary compounds. Life Sci. 1983;33 Suppl 1:477-80.

Egan et al., Prospective pharmacokinetic and pharmacodynamic validation of propofol's context sensitive T1/2. Anesthesiology. Sep. 1999;91(3A): Abstract A347.

Eisenberg, Effects of naltrexone on plasma corticosterone in opiate-naïve rats: a central action. Life Sci. Mar. 19, 1984;34(12):1185-91.

Eisenstein et al., Effect of opioids on oral Salmonella infection and immune function. Adv Exp Med Biol. 2001;493:169-76.

Epstein et al., Naltrexone attenuates acute cigarette smoking behavior. Pharmacol Biochem Behav. Jan. 2004;77(1):29-37.

Farooqui et al., μopioid receptor stimulates a growth promoting and pro-angiogenic tumor microenvironment. Proc Amer Assoc Cancer Res. 2005;46. AACR Meeting Abstract, Abstract #4650.

Farooqui et al., Naloxone acts as an antagonist of estrogen receptor activity in MCF-7 cells. Mol Cancer Ther. Mar. 2006;5(3):611-20.

Farthing et al., New drugs in the management of the irritable bowel syndrome. Drugs. Jul. 1998;56(1):11-21.

Farup et al., The Symptomatic Effect of Cisapride in Patients with Irritable Bowel Syndrome and Constipation. Scand J Gastronenerol. 1998;33:28-31.

Faura et al., Systematic review of factors affecting the ratios of morphine and its major metabolites. Pain. Jan. 1998;74(1):43-53.

Fecho et al., Assessment of the involvement of central nervous system and peripheral opioid receptors in the immunomodulatory effects of acute morphine treatment in rats. J Pharmacol Exp Ther. Feb. 1996;276(2):626-36.

Fernandez-Tome et al., Interaction between opioid agonists or naloxone and 5-HTP on feeding behavior in food-deprived rats. Pharmacol Biochem Behav. Feb. 1988;29(2):387-92.

Fingl, Chapter 43: Laxatives and cathartics. In Pharmacological Basis of Therapeutics. 1980: 1002-12.

Finn et al., Endocytosis of the mu opioid receptor reduces tolerance and a cellular hallmark of opiate withdrawal. Neuron. Dec. 6, 2001;32(5):829-39.

Flores et al., Mechanisms of morphine-induced immunosuppression: effect of acute morphine administration on lymphocyte trafficking. J Pharmacol Exp Ther. Mar. 1995;272(3):1246-51.

Foss, A review of the potential role of methylnaltrexone in opioid bowel dysfunction. Am J Surg. Nov. 2001;182(5A Suppl):19S-26S.

Foss et al., Alvimopan (Entereg™), a novel opioid antagonist, achieves active systemic concentrations. Amer Soc Clin Pharma Ther. 2005:74. Abstract P11-90.

Foss et al., Dose-related antagonism of the emetic effect of morphine by methylnaltrexone in dogs. J Clin Pharmacol. Aug. 1993;33(8):747-51.

Foss et al., Effects of methylnaltrexone on morphine-induced cough suppression in guinea pigs. Life Sci. 1996;59(15):PL235-8.

Foss et al., Enteric-coated methylnaltrexone prevents opioid-induced oral-cecal transit delay in humans. Anesth Analg. 2000;90. Abstract S409.

Foss et al., Methylnaltrexone does not antagonize the analgesic effect of morphine: a clinical study. 1995 Annual scientific meeting of the American Society of Anesthesiologists. Atlanta, Georgia, Oct. 21-25, 1995. Abstracts. Anesthesiology. Sep. 1995;83(3A Suppl):A361.

Foss et al., Methylnaltrexone reduces morphine-induced postoperative emesis by 30%. Anesth Analg. 1994;78:S119.

Foss et al., Prevention of apomorphine- or cisplatin-induced emesis in the dog by a combination of methylnaltrexone and morphine. Cancer Chemother Pharmacol. 1998;42(4):287-91.

Foss et al., Safety and tolerance of methylnaltrexone in healthy humans: a randomized, placebo-controlled, intravenous, ascending-dose, pharmacokinetic study. J Clin Pharmacol. Jan. 1997;37(1):25-30.

Foss et al., Subcutaneous methylnaltrexone reduces morphine-induced subjective effects in humans. Anesthesiology. 2001;95. Abstract A-817.

Foss et al., The efficacy or oral methylnaltrexone in decreasing the subjective effects of IV morphine. Anesth Analg. 1997;84. Abstract 5484.

France et al., Morphine, saline and naltrexone discrimination in morphine-treated pigeons. J Pharm and Exper Ther. 1987;242:195-202.

France et al., Comparison of naltrexone and quaternary naltrexone after systemic and intracerebroventricular administration in pigeons. Neuropharmacology. Jun. 1987;26(6):541-8.

France et al., Intracerebroventricular drug administration in pigeons. Pharmacol Biochem Behav. Nov. 1985;23(5):731-6.

Fraser et at, Methods for evaluating addiction liability. (A) "Attitude" of opiate addicts toward opiate-like drugs. (B) a short-term "direct" addiction test. J Pharmacol Exp Ther. Sep. 1961;133:371-87. Abstract Only.

Frässdorf et aL, Morphine induces late cardioprotection in rat hearts in vivo: the involvement of opioid receptors and nuclear transcription factor kappaB. Anesth Analg. Oct. 2005;101(4):934-41.

Frederickson et al., Metkephamid, a Systemically Active Analog of Methionine Enkephalin with Potent Opioid δ5- Receptor Activity. Science. 1991;211:603-05.

French et al., Purification and characterization of morphinone reductase from Pseudomonas putida M10. Biochem J. Jul. 1, 1994;301 ( Pt 1):97-103.

Friedman et al., Opioid antagonists in the treatment of opioid-induced constipation and pruritus. Ann Pharmacother. Jan. 2001;35(1):85-91.

Funke et al., A proton and carbon-13 nuclear magnetic resonance study of three quaternary salts of naloxone and oxymorphone. J Chem Soc. 1986:735-8.

Galligan et al., Centrally mediated inhibition of small intestinal transit and motility by morphine in the rat. J Pharmacol Exp Ther. Aug. 1983;226(2):356-61. Abstract Only.

Gan et al., Consensus guidelines for managing postoperative nausea and vomiting. Anesth Analg. Jul. 2003;97(1):62-71. Review.

Gervitz, Targeted approach: methylnaltrexone blocks opioid-induced constipation and other peripheral side effects. Topics in Pain Management. 2005;21(1):6-8. Quiz on p. 11.

Giles et al., Quaternary opiate antagonists lower blood pressure and inhibit leucine-enkephalin responses. Eur J Pharmacol. Nov. 25, 1983;95(3-4):247-52.

Gmerek et al., Independent central and peripheral mediation of morphine-induced inhibition of gastrointestinal transit in rats. J Pharmacol Exp Ther. Jan. 1986;236(1):8-13.

Goumon et al., Ascaris suum, an intestinal parasite, produces morphine. J Immunol. Jul. 1, 2000;165(1):339-43.

Green, Comparative effects of analgesics on pain threshold, respiratory frequency and gastrointestinal propulsion. Br J Pharmacol Chemother. Mar. 1959;14(1):26-34.

Grigoriev et al., Clinical gastroenterology. Ministry of Health of the Russian Federation. Russian State Medical University. 2001;491-492. Russian.

Gupta et al., Angiogenesis: a curse or cure? Postgrad Med J. Apr. 2005;81(954):236-42.

Gupta et al., Morphine mimics VEGF in vascular endothelium by promoting pro-angiogenic and survival promoting signaling and angiogenesis. FASEB Journal. 2002;16(4):A207. Abstract #182.12.

Gupta et al., Morphine stimulates angiogenesis by activating proangiogenic and survival-promoting signaling and promotes breast tumor growth. Cancer Res. Aug. 1, 2002;62(15):4491-8.

Gutstein et al., Role of inositol 1,4,5-trisphosphate receptors in regulating apoptotic signaling and heart failure. Heart Vessels. 1997;Suppl 12:53-7.

Guy et al., Chapter 1. Structural models of $Na^+$, $Ca2^+$, and $K^+$channels. In: Ion Channels and Genetic Diseases. Dawson et al., eds. 1995:1-28.

Hailes et al., Biological synthesis of the analgesic hydromorphone, an intermediate in the metabolism of morphine, by Pseudomonas putida M10. Appl Environ Microbiol. Jul. 1993;59(7):2166-70.

Hanif et al., Hypotensive effect of novel chimeric peptides of met-enkephalin and FMRFa. Regul Pept. Feb. 15, 2005;125(1-3):155-61.

He et al., Improvement of Bowel Dysfunction Caused by Opioid Analgesics: Research Advances on Methylnaltrexone. Chinese Journal of Clinical Rehabilitation. 2002;6(20):3104-05.

Hein et al., Pharmacological analysis of the discriminative stimulus characteristics of ethylketazocine in the rhesus monkey. J Pharmacol Exp Ther. Jul. 1981;218(1):7-15.

Hicks et al., Differential effects of the novel non-peptidic opioid 4-tyrosylamido-6-benzyl-1,2,3,4 tetrahydroquinoline (CGPM-9) on in vitro rat t lymphocyte and macrophage functions. Life Sci. May 4, 2001;68(24):2685-94.

Hirota et al., Loss of a gp130 cardiac muscle cell survival pathway is a critical event in the onset of heart failure during biomechanical stress. Cell. Apr. 16, 1999;97(2):189-98.

Ho et al., Beta-endorphin: peripheral opioid activity of homologues from six species. Int J Pept Protein Res. Apr. 1987;29(4):521-4.

Ho et al., Methylnaltrexone antagonizes opioid-mediated enhancement of HIV infection of human blood mononuclear phagocytes. J Pharmacol Exp Ther. Dec. 2003;307(3):1158-62. Epub Oct. 14, 2003.

Ho et al., Suppression of immunological functions in morphine addicted mice. NIDA Res Monogr. 1986;75:599-602.

Hoffmann et al., [Calcium in the prevention of stress ulcer in the rat] Langenbecks Arch Chir. 1976;Suppl:228-32. German.

Hofmann et al., Hypocalcemia during restraint stress in rats. Indication that gastric ulcer prophylaxis by exogenous calcium interferes with calcitonin release. Res Exp Med (Berl). May 30, 1979;175(2):159-68.

Hou et al., A mu-receptor opioid agonist induces AP-1 and NF-kappa B transcription factor activity in primary cultures of rat cortical neurons. Neurosci Lett. Jul. 19, 1996;212(3):159-62.

Howd et al., Naloxone and intestinal motility. Experientia. Oct. 15, 1987;34(10):1310-1.

Hussain et al., Improvement of the oral bioavailability of naltrexone in dogs: a prodrug approach. J Pharm Sci. May 1978;76(5):356-8.

Hussain et al., Naltrexone-3-salicylate (a prodrug of naltrexone): synthesis and pharmacokinetics in dogs. Pharm Res. Feb. 1988;5(2):113-5.

Hutchinson et al., Assessment in the guinea-pig ileum and mouse vas deferens of benzomorphans which have strong antinociceptive activity but do no substitute for morphine in the dependent monkey. Br J Pharmacol. Dec. 1975;55(4):541-6.

Hutchinson et al., Scintigraphic measurement of ileocaecal transit in irritable bowel syndrome and chronic idiopathic constipation. Gut. Apr. 1995;36(4):585-9.

Iorio et al., Diastereoisomeric Quaternary Morphinium Salts: Synthesis, Stereochemistry and Analgesic Properties. European Journal of Medicinal Chemistry. 1984;19(1):11-16.

Iorio et al., Narcotic agonist/antagonist properties of quaternary diastereoisomers derived from oxymorphone and naloxone. Eur J Med Chem. 1984;19(4):301-3.

Jalowiec et al., Suppression of juvenile social behavior requires antagonism of central opioid systems. Pharmacol Biochem Behav. Jul. 1989;33(3):697-700.

Jankovic et al., Quaternary naltrexone: its immunomodulatory activity and interaction with brain delta and kappa opioid receptors. Immunopharmacology. Sep.-Oct. 1994;28(2):105-12.

Jasinski, Assessment of the Abuse Potentiality of Morphinelike Drugs (Methods Used in Man). Drug Addiction J. 1997:197-258.

Jasinski, Tolerance and Dependence to opiates. Acta Anaesthesiol Scand. Jan. 1997;41(1 Pt 2):184-6.

Jenab et al., Ethanol and naloxone differentially upregulate delta opioid receptor gene expression in neuroblastoma hybrid (NG108-15) cells. Brain Res Mol Brain Res. Nov. 1994;27(1):95-102.

Johnson et al., Stability of tacrolimus with morphine sulfate, hydromorphone hydrochloride, and ceftazidime during simulated intravenous coadministration. Am J Health Syst Pharm. Jan. 15, 1999;56(2):164-9.

Kakeji et al., Preclinical studies of the combination of angiogenic inhibitors with cytotoxic agents. Invest New Drugs. 1997;15(1):39-48.

Kasamatsu et al., Attenuation of aortic baroreflex responses by microinjections of endomorphin-2 into the rostral ventrolateral medullary pressor area of the rat. Am J Physiol Regul Integr Comp Physiol. Jul. 2005;289(1):R59-67. Epub Feb. 17, 2005.

Kaufman et al., Role of opiate receptors in the regulation of colonic transit. Gastroenterology. Jun. 1988;94(6):1351-6.

Kehlet et al., Review of postoperative ileus. Am J Surg. Nov. 2001;182(5A Suppl):3S-10S. Review.

Keith et al., Failure of naloxone to prevent the emetic activity of apomorphine in dogs. J Vet Pharmacol Ther. Dec. 1981;4(4):315-6.

Kim et al., Assay for methylnaltrexone in rat brain regions and serum by high-performance liquid chromatography with coulometric electrochemical detection. Chromatographia. Oct. 1989;28(7-8):359-63.

King et al., Hypothalamic-pituitary-adrenocortical (HPA) axis response and biotransformation of oral naltrexone: preliminary examination of relationship to family history of alcoholism. Neuropsychopharmacology. Jun. 2002;26(6):778-88.

Kinsman et al., Effect of naloxone on feedback regulation of small bowel transit by fat. Gastroenterology. Aug. 1984;87(2):335-7.

Knowles et al., Slow transit constipation: a model of human gut dysmotility. Review of possible aetiologies. Neurogastroenterol Motil. Apr. 2000;12(2):181-96.

Koblish et al., Behavioral profile of ADL 8-2698, a novel GI-restricted μopioid receptor antagonist. Society for Neuroscience Abstracts. 2001;27(2):2407. Abstract Only.

Kobylecki et al., N-Methylnalorphine: definition of N-allyl conformation for antagonism at the opiate receptor. J Med Chem. Nov. 1982;25(11):1278-80.

Koch et al., Inhibitory neuropeptides and intrinsic inhibitory innervation of descending human colon. Dig Dis Sci. Jun. 1, 1991.;36(6):712-8. Abstract Only.

Koczka, et al., Selective Quaternization of Compounds with Morphine Skeleton. Acta Chimica Academica Scien Hung. 1967;51(4):393-02.

Kodani et al., Delta-opioid receptor-induced late preconditioning is mediated by cyclooxygenase-2 in conscious rabbits. Am J Physiol Heart Circ Physiol. Nov. 2002;283(5):H1943-57.

Koob et al., Effects of opiate antagonists and their quaternary derivatives on heroin self-administration in the rat. J Pharmacol Exp Ther. May 1984;229(2):481-6.

Kosten et al., Naltrexone and morphine alter the discrimination and plasma levels of ethanol. Behav Pharmacol. Feb. 1999;10(1):1-13.

Kostic, CAS Abstract Document No. 127: 13345, 1997.

Kotake et al., Variations in demethylation of N-methylnaltrexone in mice, rats, dogs, and humans. Xenobiotica. Nov. 1989;19(11):1247-54.

Kratzel et al., An Efficient Synthesis of 14-Halogenomethyl-Substituted C-Normorphinans. Heterocycles. 1987;26(10):2703-10.

Kratzel et al., Synthesis of 5a,11b-Propanonaphtho[1,2-e][1,2]oxazepines as Potential Opioid Analgesics. J Chem Soc Perkin 1. 1994;11:1541-43.

Kromer et al., Endogenous opioids, the enteric nervous system and gut motility. Dig Dis. 1990;8(6):361-73.

Kromer et al., The current status of opioid research on gastrointestinal motility. Life Sci. 1989;44(9):579-89.

Law et al., Agonist activation of delta-opioid receptor but not mu-opioid receptor potentiates fetal calf serum or tyrosine kinase receptor-mediated cell proliferation in a cell-line-specific manner. Mol Pharmacol. Jan. 1997;51(1):152-60.

Law et al., Properties of delta opioid receptor in neuroblastoma NS20Y: receptor activation and neuroblastoma proliferation. J Pharmacol Exp Ther. Jan. 1995;272(1):322-32.

Law et al., Regulation of opioid receptor activities. J Pharmacol Exp Ther. May 1999;289(2):607-24.

Lazar et al., Synthesis and biological activity of the phosphate and sulfate esters of naloxone and naltrexone. Eur J Med Chem. 1994;29:45-53.

Leander, A kappa opioid effect: increased urination in the rat. J Pharmacol Exp Ther. Jan. 1983;224(1):89-94.

Li et al., Methadone enhances human immunodeficiency virus infection of human immune cells. J Infect Dis. Jan. 1, 2002;185(1):118-22. Epub Dec. 14, 2001.

Lim et al., Morphine preconditions Purkinje cells against cell death under in vitro simulated ischemia-reperfusion conditions. Anesthesiology. Mar. 2004;100(3):562-8.

Linn et al., Peripherally restricted μ-opioid receptor antagonists: a review. Tech Reg Anesth Pain Manag. Jul. 2007;11(1):27-32.

Little, et al., ADL 8-2698, a GI restricted opioid antagonist, blocks the antisecretory and colorectal transit effects of morphine and loperamide. Society for Neuroscience Abstracts. 2001; 27(2):2407. Abstract Only.

Livingston et al., Postoperative ileus. Dig Dis Sci. Jan. 1990;35(1):121-32.

Lopez et al., Demonstration of long-lasting blockade of experimental ileus in rats by an opioid k-agonist. Gastroenterology. 1995;108(4):Abstract A640.

Lydon et al., Intravenous methylnaltrexone attenuates intrathecal morphine induced delayed gastric emptying in rats. ESA Free Paper Prize Competition. Eur J Anaesthesiol. Apr. 2001;18 Suppl 21:92. Abstract A-327.

Lysle et al., Evidence for the involvement of the caudal region of the periaqueductal gray in a subset of morphine-induced alterations of immune status. J Pharmacol Exp Ther. Jun. 1996;277(3):1533-40.

Lysle et al., Modulation of immune status by a conditioned aversive stimulus: evidence for the involvement of endogenous opioids. Brain Behav Immun. Jun. 1992;6(2):179-88.

Machelska et al., Selectins and integrins but not platelet-endothelial cell adhesion molecule-1 regulate opioid inhibition of inflammatory pain. Br J Pharmacol. Jun. 2004;142(4):772-80. Epub May 24, 2004.

Mack, Paralytic ileus: response to naloxone. Br J Surg. Oct. 1989;76(10):1101.

Magazine et al., Morphine-induced conformational changes in human monocytes, granulocytes, and endothelial cells and in invertebrate immunocytes and microglia are mediated by nitric oxide. J Immunol. Jun. 15, 1996;156(12):4845-50.

Magnan et al., The binding spectrum of narcotic analgesic drugs with different agonist and antagonist properties. Naunyn Schmiedebergs Arch Pharmacol. Jun. 1982;319(3):197-205.

Maguire et al., Pharmacological profiles of fentanyl analogs at mu, delta and kappa opiate receptors. Eur J Pharmacol. Mar. 24, 1992;213(2):219-25. Abstract Only.

Malspeis et al., Metabolic Reduction of Naltrexone I. Synthesis, Separation and Characterization of Naloxone and Maltrexone Reduction Products and Qualitative Assay of Urine and Bile Following Adminstration of Naltrexone, α-naltrexol, or β-naltrexol. Chem Pathol Pharmacol. 1975;12(1):43-65.

Manara et al., Inhibition of gastrointestinal transit by morphine in rats results primarily from direct drug action on gut opioid sites. J Pharmacol Exp Ther. Jun. 1986;237(3):945-9. Abstract Only.

Manara et al., Peripheral selectivity of quaternary narcotic antagonists: relative ability to prevent gastrointestinal transit inhibition and antinociception in morphinized rats. Adv. Endog. Exog. Opioids, Poroc. Int. Narc. Res. Conf., 12th (1981): 402-4.

Manara et al., The central and peripheral influences of opioids on gastrointestinal propulsion. Annu Rev Pharmacol Toxicol. 1985;25:249-73.

Mančev et al., The immunomodulating effects of specific opioid receptor antagonists after their intracerebroventricular application. Intl J Thymol. 1999;7(12-13):589-95.

Marmor et al., Coronary artery disease and opioid use. Am J Cardiol. May 15, 2004;93(10):1295-7.

McBride et al., delta2 opioid receptor agonist facilitates mean arterial pressure recovery after hemorrhage in conscious rats. Shock. Mar. 2005;23(3):264-8.

McCance-Katz et al., Interactions between buprenorphine and antiretrovirals. II. The protease inhibitors nelfinavir, lopinavir/ritonavir, and ritonavir. Clin Infect Dis. Dec. 15, 2006;43 Suppl 4:S235-46.

McCarthy et al., Opioids, opioid receptors, and the immune response. Drug Alcohol Depend. Apr. 1, 2001;62(2):111-23.

McCarthy et al., Preliminary studies on the use of plasma β-endorphin in horses as an indicator of stress and pain. J Equine Vet Sci. 1993;13(4):216-9.

McQuay, et al., Opioid problems and morphine metabolism and excretion. http://www.medicine.ox.ac.uk/bandolier/booth/painpag/wisdom/c14.html. Last accessed Feb. 8, 2010. 24 pages.

McQuay, Opioid use in chronic pain. Acta Anaesthesiol Scand. Jan. 1997;41(1 Pt 2):175-83.

Mellon et al., Evidence for central opioid receptors in the immunomodulatory effects of morphine: review of potential mechanism(s) of action. J Neuroimmunol. Mar. 15, 1998;83(1-2):19-28.

Melzig et al., Stimulation of endothelial angiotensin-converting enzyme by morphine via non-opioid receptor mediated processes. Pharmazie. Sep. 1998;53(9):634-7.

Mickley et al., Quaternary naltrexone reverses morphine-induced behaviors. Physiol Behav. Aug. 1985;35(2):249-53.

Miedema et al., Methods for decreasing postoperative gut dysmotility. Lancet Oncol. Jun. 2003;4(6):365-72.

Misra et al., Intravenous kinetics and metabolism of [15,16-3H]naltrexonium methiodide in the rat. J Pharm Pharmacol. Mar. 1987;39(3):225-7.

Miyagi et al., Morphine induces gene expression of CCR5 in human CEMx174 lymphocytes. J Biol Chem. Oct. 6, 2000;275(40):31305-10.

Moerman et al., Evaluation of methylnaltrexone for the reduction of postoperative vomiting and nausea incidences. Acta Anaesthesiol Belg. 1995;46(3-4):127-32.

Moss, et al., Selective postoperative inhibition of gastrointestinal opioid receptors. N. Engl. J. Med. 2002;346(6):455.

Moss et al., Methylnaltrexone prevents morphine-induced CCR5 receptor expression. Anesthesiology. 2003;99. Abstract A-961.

Moss et al., Opioid-induced changes in pulmonary barrier integrity may explain heroid-induced pulmonary edema. American Society of Anesthesiologists presentation, Oct. 17, 2007 in San Francisco, CA. Abstract A1980.

Moss et al., Pain relief without side effects: peripheral opiate antagonists. 33$^{rd}$ ASA Refresher Courses in Anesthesiology, Philadelphia, Lippincott Williams * Wilkins, Schwartz, A.J. editor. 2006;33:175-86.

Mucha, Is the motivational effect of opiate withdrawal reflected by common somatic indices of precipitated withdrawal? A place conditioning study in the rat. Brain Res. Aug. 25, 1987;418(2):214-20.

Mucha, Taste aversion involving central opioid antagonism is potentiated in morphine-dependent rats. Life Sci. 1989;45(8):671-8.

Murphy et al., Pharmaconkinetic of epidural administered methylnaltrexone a novel peripheral opioid anatagonist. American Society of Anesthesiologists, 1999 annual meeting. Dallas, Texas, USA. Oct. 9-13, 1999. Anesthesiology. Sep. 1999;91(3A Suppl):A349.

Murphy et al., Opioid antagonist modulation of ischaemia-induced ventricular arrhythmias: a peripheral mechanism. J Cardiovasc Pharmacol. Jan. 1999;33(1):122-5.

Murphy et al., Opioid-induced delay in gastric emptying: a peripheral mechanism in humans. Anesthesiology. Oct. 1997;87(4):765-70.

Murphy et al., Pharmacokinetic profile of epidurally administered methylnaltrexone, a novel peripheral opioid antagonist in a rabbit model. Br J Anaesth. Jan. 2001;86(1):120-2.

Nair et al., Morphine Modulates the Expression of Chemokines and their Receptors by Peripheral Blood Mononuclear Cells (PBMC) from Normal Donors. J Allergy Clin Immunol. 1998:101(1):S57. Abstract 244.

Naranjo et al., Evidence for a central but not adrenal, opioid mediation in hypertension induced by brief isolation in the rat. Life Sci. May 26, 1986;38(21):1923-30.

Nelson, Morphine modulation of the contact hypersensitivity response: A pharmacological and immunological characterization. University of North Carolina at Chapel Hill. Dissertation Abstracts International. 2001;62/03-B:1635. 94 pages. Abstract Only.

Nelson et al., Involvement of central mu- but not delta- or kappa-opioid receptors in immunomodulation. Brain Behav Immun. Sep. 2000;14(3):170-84.

Nemeth-Lefkowitz et al., Hematological and Immunological Effects of Methadone Administration in Mice. Research Communication in Substances of Abuse. 1980;1(2):177-83.

Neumann et al., Plasma morphine concentrations during chronic oral administration in patients with cancer pain. Pain. Jul. 1982;13(3):247-52.

Nielsen et al., Glycolamide Esters as Biolabile Prodrugs of Carboxylic Acid Agents: Synthesis, Stability, Biocenversion, and Physicochemical Properties. J Pharma Sci. 1988;77:285-98.

Niemegeers et al., Difenoxine (R 15403), the active metabolite of diphenoxylate (R 1132). 2. Difneozine, a potent, orally active and safe antidiarrheal agent in rats. Arzneimittelforschung. Mar. 1972;22(3):516-8.

Novick et al., Natural killer cell activity and lymphocyte subsets in parenteral heroin abusers and long-term methadone maintenance patients. J Pharmacol Exp Ther. Aug. 1989;250(2):606-10.

Odio et al., Central but not peripheral opiate receptor blockade prolonged pituitary-adrenal responses to stress. Pharmacol Biochem Behav. Apr. 1990;35(4):963-9.

O'Keefe et al., Bowel Disorders Impair Functional Status and Quality of Life in the Elderly: A Population-Based Study. J Gerontol. 1995;50:184-89.

Osinski et al., Determination of methylnaltrexone in clinical samples by solid-phase extraction and high-performance liquid chromatography for a pharmacokinetics study. J Chromatogr B Analyt Technol Biomed Life Sci. Nov. 25, 2002;780(2):251-9.

Papapetropoulos et al., Nitric oxide synthase inhibitors attenuate transforming-growth-factor-beta 1-stimulated capillary organization in vitro. Am J Pathol. May 1997;150(5):1835-44.

Pappagallo, Incidence, prevalence, and management of opioid bowel dysfunction. Am J Surg. Nov. 2001;182(5A Suppl):11S-18S.

Pasi et al., Angiogenesis: modulation with opioids. Gen Pharmacol. 1991;22(6):1077-9.

Patel et al., COX-2 and iNOS in opioid-induced delayed cardioprotection in the intact rat. Life Sci. May 28, 2004;75(2):129-40.

Paulson et al., Alvimopan: an oral, peripherally acting, mu-opioid receptor antagonist for the treatment of opioid-induced bowel dysfunction—a 21-day treatment-randomized clinical trial. J Pain. Mar. 2005;6(3):184-92.

Peart et al., Opioid-induced preconditioning: recent advances and future perspectives. Vascul Pharmacol. Apr.-May 2005;42(5-6):211-8. Epub Mar. 17, 2005.

Peeters et al., The motilin antagonist ANQ-11125 blocks motilide-induced contractions in vitro in the rabbit. Biochem Biophys Res Commun. Jan. 28, 1994;198(2):411-6. Abstract Only.

Peterson et al., Morphine promotes the growth of HIV-1 in human peripheral blood mononuclear cell cocultures. AIDS. Sep. 1990;4(9):869-73.

Pham et al., Drugs of Abuse: Chemistry, Pharmacology, Immunology and AIDS; National Institute of Drug Research 96: Monograph Series. U.S. Department of Health and Human Services; 1990. 243 pages.

Polak et al., Enkephalin-like immunoreactivity in the human gastrointestinal tract. Lancet. May 7, 1977;1(8019):972-4.

Polakiewicz et al., mu-Opioid receptor activates signaling pathways implicated in cell survival and translational control. J Biol Chem. Sep. 4, 1998;273(36):23534-41.

Poonawala et al., Opioids heal ischemic wounds in the rat. Wound Repair Regen. Mar.-Apr. 2005;13(2):165-74.

Powell et al., Paradoxical effects of the opioid antagonist naltrexone on morphine analgesia, tolerance, and reward in rats. J Pharmacol Exp Ther. Feb. 2002;300(2):588-96.

Pugsley et al., Cardiovascular actions of the kappa-agonist, U-50,488H, in the absence and presence of opioid receptor blockade. Br J Pharmacol. Mar. 1992;105(3):521-6.

Quang-Contagrel et al., Long-term methadone treatment: effect on CD4+ lymphocyte counts and HIV-1 plasma RNA level in patients with HIV infection. Eur J Pain. 2001;5(4):415-20.

Quock, et al, Microwave facilitation of methylnaltrexone antagonism of morphine-induced analgesia in mice. J Bioelect. 1986;5(1):35-46.

Quock et al., Narcotic antagonist-induced hypotension in the spontaneously hypertensive rat. Life Sci. Sep. 2, 1985;37(9):819-26.

Quock et al., Narcotic antagonist potentiation of apomorphine drug effect: a stereospecific, centrally mediated drug action. Prog Neuropsychopharmacol Biol Psychiatry. 1985;9(3):239-43.

Radulovićet al., Opioid receptor-mediated suppression of humoral immune response in vivo and in vitro: involvement of kappa opioid receptors. J Neuroimmunol. Mar. 1995;57(1-2):55-62.

Ramabadran, Effects of N-methylnaloxone and N-methylnaltrexone on nociception and precipitated abstinence in mice. Life Sci. Sep. 20-27, 1982;31(12-13):1253-6.

Read et al., Interpretation of the breath hydrogen profile obtained after ingesting a solid meal containing unabsorbable carbohydrate. Gut. Aug. 1985;26(8):834-42.

Reisine et al., Opioid Analgesics and Antagonists. In: Goodman & Goodman's The Pharmacological Basis of Therapeutics. 9$^{th}$ Ed. 1996:521-55.

Resnick et al., Delayed gastric emptying and postoperative ileus after nongastric abdominal surgery: part I. Am J Gastroenterol. May 1997;92(5):751-62.

Resnick et al., Delayed gastric emptying and postoperative ileus after nongastric abdominal surgery: part II. Am J Gastroenterol. Jun. 1997;92(6):934-40.

Risdahl et al., Opiates and infection. J Neuroimmunol. Mar. 15, 1998;83(1-2):4-18.

Rivière et al., Fedotozine reverses ileus induced by surgery or peritonitis: action at peripheral kappa-opioid receptors. Gastroenterology. Mar. 1993;104(3):724-31.

Robinson et al., Oral naloxone in opioid-associated constipation. Lancet. Aug. 31, 1991;338(8766):581-2.

Roger et al., Colonic motor responses in the pony: relevance of colonic stimulation by opiate antagonists. Am J Vet Res. Jan. 1985;46(1):31-5.

Roy et al., Morphine modulates NF kappa B activation in macrophages. Biochem Biophys Res Commun. Apr. 17, 1998;245(2):392-6.

Russell et al., Antagonism of gut, but not central effects of morphine with quaternary narcotic antagonists. Eur J Pharmacol. Mar. 12, 1982;78(3):255-61.

Sachs et al., Peripheral analgesic blockade of hypernociception: activation of arginine/NO/cGMP/protein kinase G/ATP-sensitive K+ channel pathway. Proc Natl Acad Sci U S A. Mar. 9, 2004;101(10):3680-5. Epub Feb. 27, 2004.

Saffran et al., A new approach to the oral administration of insulin and other peptide drugs. Science. Sep. 5, 1986;233(4768):1081-4. Abstract Only.

Sakurada et al., Differential antagonism of endomorphin-1 and endomorphin-2 supraspinal antinociception by naloxonazine and 3-methylnaltrexone. Peptides. May 2002;23(5):895-901.

Sandner-Keisling et al., Pharmacology of opioid inhibition to noxious uterine cervical distension. Anesthesiology. Oct. 2002;97(4):966-71.

Sawhney et al., Bioerodible Hydrogels Based on Photopolymerized Poly(ethylene glycol)-co-poly(α-hydroxy acid) Diacrylate Macromers. Macromolecules. 1993;26:581-87.

Schaefer et al., Effects of opioid antagonists and their quaternary derivatives on locomotor activity and fixed ratio responding for brain self-stimulation in rats. Pharmacol Biochem Behav. Nov. 1985;23(5):797-802.

Schang et al., Beneficial effects of naloxone in a patient with intestinal pseudoobstruction. Am J Gastroenterol. Jun. 1985;80(6):407-11.

Schang et al., How does morphine work on colonic motility? An electromyographic study in the human left and sigmoid colon. Life Sci. Feb. 24, 1986;38(8):671-6.

Schiller et al., Studies of the mechanism of the antidiarrheal effect of codeine. J Clin Invest. Nov. 1982;70(5):999-1008.

Schmidhammer, et al., Synthesis and biological evaluation of 14-alkoxymorphinans. Part 9[1]. 14-O-ethyl-5-methylnaltrexone, an opioid antagonist with unusual selectivity. Helv Chim Acta. 1993;(1):476-80.

Schmidhammer, et al., Synthesis and biological evaluation of 14-alkoxymorphinans. Part 10[1]. 14-O-methyl derivatives of 5-methylnalthrexone and 5-methylnaloxone. Helv Chim Acta. 1994;77(6):1585-9.

Schmidt et al., Alvimopan* (ADL 8-2698) is a novel peripheral opioid antagonist. Am J Surg. Nov. 2001;182(5A Suppl):27S-38S.

Scholz, Managing constipation that's opioid-induced. 2000;63(6):103.

Schreier et al., Central regulation of intestinal function: morphine withdrawal diarrhea. Proc West Pharmacol Soc. 1982;25:151-4.

Schubert-Zsilavecz et al., [Das reizdarmsyndrom] The irritable bowel syndrome. Deutsche apotheker zeitung. Aug. 22, 2002;142(34): 40-9. German.

Schug et al., A long-term survey of morphine in cancer pain patients. J Pain Symptom Manage. Jul. 1992;7(5):259-66. Abstract Only.

Schuller et al., M6G, but not morphine, inhibits GI transit in mu opioid receptor deficient mice. Society of Neuroscience Abstracts. 1998;24:524. Abstract 210.7.

Sezen et al., Renal excretory responses produced by the delta opioid agonist, BW373U86, in conscious rats. J Pharmacol Exp Ther. Oct. 1998;287(1):238-45.

Shahbazian et al., Involvement of mu- and kappa-, but not delta-, opioid receptors in the peristaltic motor depression caused by endogenous and exogenous opioids in the guinea-pig intestine. Br J Pharmacol. Feb. 2002;135(3):741-50.

Shavit et al., Effects of a single administration of morphine or footshock stress on natural killer cell cytotoxicity. Brain Behav Immun. Dec. 1987;1(4):318-28.

Shi et al., Cardioprotective effects of morphine on rat heart suffering from ischemia and reperfusion. Chin Med J (Engl). Jul. 2003;116(7):1059-62.

Simonin et al., kappa-Opioid receptor in humans: cDNA and genomic cloning, chromosomal assignment, functional expression, pharmacology, and expression pattern in the central nervous system.. Proc Natl Acad Sci U S A. Jul. 18, 1995;92(15):7006-10.

Simonin et al, The human delta-opioid receptor: genomic organization, cDNA cloning, functional expression, and distribution in human brain. Mol Pharmacol. Dec. 1994;46(6):1015-21. Abstract Only.

Soldani et al., Central and peripheral involvement of mu receptors in gastric secretory effects of opioids in the dog. Eur J Pharmacol. Nov. 19, 1985;117(3):295-301.

Solvason et al., Naltrexone blocks the expression of the conditioned elevation of natural killer cell activity in BALB/c mice. Brain Behav Immun. Sep. 1989;3(3):247-62.

Stankski et al., Kinetics of intravenous and intramuscular morphine. Clin Pharmacol Ther. Jul. 1978;24(1):52-9.

Steele et al., HIV-1 Infection and Opioid Administration Modulate the Expression of Chemokine Receptors. Drug and Alcohol Dependence. 2000:60(Supp 1):S212. Abstract 599.

Stefano et al., Delta2 opioid receptor subtype on human vascular endothelium uncouples morphine stimulated nitric oxide release. Int J Cardiol. Apr. 30, 1998;64 Suppl 1:S43-51.

Stefano et al., Long-term exposure of human blood vessels to HIV gp120, morphine, and anandamide increases endothelial adhesion of monocytes: uncoupling of nitric oxide release. J Cardiovasc Pharmacol. Jun. 1998;31(6):862-8.

Stefano et al., Morphine enhances nitric oxide release in the mammalian gastrointestinal tract via the micro(3) opiate receptor subtype: a hormonal role for endogenous morphine. J Physiol Pharmacol. Mar. 2004;55(1 Pt 2):279-88.

Stefano et al., Presence of the mu3 opiate receptor in endothelial cells. Coupling to nitric oxide production and vasodilation. J Biol Chem. Dec. 22, 1995;270(51):30290-3.

Steinbrook et al., An opioid antagonist for postoperative ileus. N Engl J Med. Sep. 27, 2001;345(13):988-9.

Stephenson et al., Methylnaltrexone reverses opioid-induced constipation. Lancet Oncol. Apr. 2002;3(4):202.

Sternini et al., The opioid system in the gastrointestinal tract. Neurogastroenterol Motil. Oct. 2004;16 Suppl 2:3-16.

Stewart et al., Central and peripheral actions of morphine on intestinal transit. J Pharmacol Exp Ther. Jun. 1978;205(3):547-55.

Stiene-Martin et al., Regional, developmental, and cell cycle-dependent differences in mu, delta, and kappa-opioid receptor expression among cultured mouse astrocytes. Glia. Mar. 1998;22(3):249-59.

Suzuki et al., Morphine suppresses lymphocyte apoptosis by blocking p53-mediated death signaling. Biochem Biophys Res Commun. Sep. 5, 2003;308(4):802-8.

Swan, et al., NIDA plays key role in studying links between AIDS and drug abuse. AIDS Research, NIDA Notes. 1995; 10(3):1-4.

Sykes, Oral naloxone in opioid-associated constipation. Lancet. Jun. 15, 1991;337(8755):1475.

Sykes, Chapter 9. Using oral naloxone in management of opioid bowel dysfunction. Handbook of Opioid Bowel Syndrome, New York, Haworth Medical Press, Yuan, C-S, editor. 2005:175-95.

Szabo et al., Interactions of opioid receptors, chemokines, and chemokine receptors. Adv Exp Med Biol. 2001;493:69-74.

Taguchi et al., Selective postoperative inhibition of gastrointestinal opioid receptors. N Engl J Med. Sep. 27, 2001;345(13):935-40.

Talley et al., Pharmacologic therapy for the irritable bowel syndrome. Am J Gastroenterol. Apr. 2003;98(4):750-8.

Tavani et al., Morphine is most effective on gastrointestinal propulsion in rats by intraperitoneal route: evidence for local action. Life Sci. Dec. 8, 1980;27(23):2211-7.

Tegeder et al., Opioids as modulators of cell death and survival—unraveling mechanisms and revealing new indications. Pharmacol Rev. Sep. 2004;56(3):351-69.

Thomas et al., A phase III double-blind placebo-controlled trial of methylnaltrexone (MNTX) for opioid-induced constipation (OIC) in advanced medical illness (AMI). Abstract No LBA8003 from the 2005 ASCO Annual Meeting. 3 pages.

Thomas et al., Amelioration of peripheral side effects of opioids: clinical experience with methylnaltrexone (MNTX). Proc World Congr Anesth. 2004:107. Abstract Only.

Thompson et al., Laxatives: clinical pharmacology and rational use. Drugs. Jan. 1980;19(1):49-58.

Thompson et al., Opioid stimulation in the ventral tegmental area facilitates the onset of maternal behavior in rats. Brain Res. Dec. 16, 1996;743(1-2):184-201.

Tomiyasu et al., Analysis of intercostal nerve damage associated with chronic post-thoracotomy pain. Anesthesiology. 2001;95. Abstract A-964.

Tryoen-Toth et al., Regulation of kappa-opioid receptor mRNA level by cyclic AMP and growth factors in cultured rat glial cells. Brain Res Mol Brain Res. Mar. 30, 1998;55(1):141-50.

Ukai et al., Suppression of deprivation-induced water intake in the rat by opioid antagonists: central sites of action. Psychopharmacology (Berl). 1987;91(3):279-84.

Uwai et al., Syntheses and receptor-binding studies of derivatives of the opioid antagonist naltrexone. Bioorg Med Chem. Jan. 15, 2004;12(2):417-21.

Valentino et al., Quaternary naltrexone: evidence for the central mediation of discriminative stimulus effects of narcotic agonists and antagonists. J Pharmacol Exp Ther. Jun. 1981;217(3):652-9.

Valentino et al., Receptor binding, antagonist, and withdrawal precipitating properties of opiate antagonists. Life Sci. Jun. 20, 1983;32(25):2887-96.

Vallejo et al., Opioid therapy and immunosuppression: a review. Am J Ther. Sep.-Oct. 2004;11(5):354-65.

Vaughan et al., Human antibodies by design. Nat Biotechnol. Jun. 1998;16(6):535-9.

Vermiere et al., Stability and compatibility of morphine. International Journal of Pharmaceutics. 1999;187:17-51.

Waldhoer et al., Opioid receptors. Annu Rev Biochem. 2004;73:953-90.

Walker, et al., Role of central versus peripheral opioid receptors in analgesia induced by repeated administration of opioid antagonists. Psychopharmacology. 1991;104(2):164-6.

Walsh et al., the symptoms of advanced cancer: relationship to age, gender, and performance status in 1,000 patients. Support Care Cancer. May 2000;8(3):175-9. Abstract Only.

Wang et al., A non-peptide substance P antagonist (CP-96,345) inhibits morphine-induced NF-kappa B promoter activation in human NT2-N neurons. J Neurosci Res. Feb. 15, 2004;75(4):544-53.

Wang et al., Determination of tungsten in bulk drug substance and intermediates by ICP-AES and ICP-MS. J Pharm Biomed Anal. May 1999;19(6):937-43. Abstract Only.

Wang et al., Human mu opiate receptor. cDNA and genomic clones, pharmacologic characterization and chromosomal assignment. FEBS Lett. Jan. 31, 1994;338(2):217-22. Abstract Only.

Wang et al., Mobilization of calcium from intracellular stores as one of the mechanisms underlying the antiopioid effect of cholecystokinin octapeptide. Peptides. Sep.-Oct. 1992;13(5):947-51.

Wang et al., Morphine negatively regulates interferon-gamma promoter activity in activated murine T cells through two distinct cyclic AMP-dependent pathways. J Biol Chem. Sep. 26, 2003;278(39):37622-31. Epub Jul. 3, 2003

Wang et al., The immunosuppressive effects of chronic morphine treatment are partially dependent on corticosterone and mediated by the mu-opioid receptor. J Leukoc Biol. May 2002;71(5):782-90.

Warren et al., Effects of quaternary naltrexone and chlordiazepoxide in squirrel monkeys with enhanced sensitivity to the behavioral effects of naltrexone. J Pharmacol Exp Ther. Nov. 1985;235(2):412-7.

Wei et al., Effects of Subcutaneous Methylnaltrexone on Morphine-Induced Gut Motility Changes: A Clinical Trial. Abstracts of the 2002 Annual Meeting of the American Society for Clinical Pharmacology and Therapeutics. Atlanta, Georgia, USA. Mar. 24-27, 2002. Clin Pharmacol Ther. Feb. 2002;71(2):P11. Abstract MPI-26.

Wei et al., Opioid-induced immunosuppression: is it centrally mediated or peripherally mediated? Biochem Pharmacol. Jun. 1, 2003;65(11):1761-6.

Wei et al., Pharmacokinetics of subcutaneous methylnaltrexone: different route administration comparison. 2001. ASA Annual Meeting Abstracts. Oct. 14-18, 2001. Chicago, IL. Abstract A-962.

Wentland et al., Synthesis and opioid receptor binding properties of a highly potent 4-hydroxy analogue of naltrexone. Bioorg Med Chem Lett. Apr. 15, 2005;15(8):2107-10.

Whistler et al., Functional dissociation of mu opioid receptor signaling and endocytosis: implications for the biology of opiate tolerance and addiction. Neuron. Aug. 1999;23(4):737-46.

Willett et al., Direct evidence that the VEGF-specific antibody bevacizumab has antivascular effects in human rectal cancer. Nat Med. Feb. 2004;10(2):145-7. Epub Jan. 25, 2004.

Willette, et al., Evidence for anticholinergic effects of naltrexone methylbromide. Res Comm Subst Abuse. 1983;4(4):325-37.

Wilmore et al., Can we minimize the effects of opioids on the bowel and still achieve adequate pain control? Am J Surg. Nov. 2001;182(5A Suppl):1S-2S.

Wingo et al., Cancer statistics, 1995. CA Cancer J Clin. Jan.-Feb. 1995;45(1):8-30.

Witkin et al., Pharmacology of 2-amino-indane hydrochloride (Su-8629): a potent non-narcotic analgesic. J Pharmacol Exp Ther. Sep. 1961;133:400-8. Abstract Only.

Wittert et al., Tissue distribution of opioid receptor gene expression in the rat. Biochem Biophys Res Commun. Jan. 26, 1996;218(3):877-81.

Wolff et al., Alvimopan, a novel, peripherally acting mu opioid antagonist: results of a multicenter, randomized, double-blind, placebo-controlled, phase III trial of major abdominal surgery and postoperative ileus. Ann Surg. Oct. 2004;240(4):728-34; discussion 734-5.

Wybran et al., Suggestive evidence for receptors for morphine and methionine-enkephalin on normal human blood T lymphocytes. J Immunol. Sep. 1979;123(3):1068-70.

Yamamoto et al., Inhibition of stress-stimulated colonic propulsion by alpha 2-adrenoceptor antagonists in rats. Neurogastroenterol Motil. Dec. 1998;10(6):523-32. Abstract Only.

Yeh et al., Stability of morphine in aqueous solution. Am J Hosp Pharmacy. 1960;17(2):101-103.

Yoshida et al., Effect of surgical stress on endogenous morphine and cytokine levels in the plasma after laparoscopoic or open cholecystectomy. Surg Endosc. Feb. 2000;14(2):137-40.

Yuan et al., Antagonism of chronic opioid-induce gut effects. Anesth Analg. 2000;90:S1-523. Abstract 5479.

Yuan et al., Antagonism of gastrointestinal opioid effects. Reg Anesth Pain Med. Nov.-Dec. 2000;25(6):639-42.

Yuan et al., Clinical status of methylnaltrexone, a new agent to prevent and manage opioid-induced side effects. J Support Oncol. Mar.-Apr. 2004;2(2):111-7; discussion 119-22.

Yuan et al., Dose-related effects of oral acetaminophen on cold-induced pain: a double-blind, randomized, placebo-controlled trial. Clin Pharmacol Ther. Mar. 1998;63(3):379-83.

Yuan et al., Effects of enteric-coated methylnaltrexone in preventing opioid-induced delay in oral cecal transit time. Clin Pharmacol Ther. Apr. 2000;67(4):398-404.

Yuan et al., Effects of intravenous methylnaltrexone on opioid-induced gut motility and transit time changes in subjects receiving chronic methadone therapy: a pilot study. Pain. Dec. 1999;83(3):631-5.

Yuan et al., Effects of low-dose morphine on gastric emptying in healthy volunteers. J Clin Pharmacol. Nov. 1998;38(11):1017-20.

Yuan et al., Effects of methylnaltrexone on chronic opioid induced gut motility and transit time changes. Br J Anaesth. 1998;81(1):94. Abstract Only.

Yuan et al., Effects of methylnaltrexone on chronic opioid-induced gut motility and transit time changes. University of Leicester—Abstracts from the Eighth International Symposium on Pain, Anaesthesia and Endocrinology. Sep. 18-19, 1997.

Yuan et al., Effects of methylnaltrexone on morphine-induced inhibition of contractions in isolated guinea-pig and human intestine. Anesthesiology. Sep. 1995; 83(3A). Abstract A358.

Yuan et al., Effects of methylnaltrexone on morphine-induced inhibition of contraction in isolated guinea-pig ileum and human intestine. Eur J Pharmacol. Mar. 24, 1995;276(1-2):107-11.

Yuan et al., Effects of subcutaneous methylnaltrexone on morphine-induced peripherally mediated side effects: a double-blind randomized placebo-controlled trial. J Pharmacol Exp Ther. Jan. 2002;300(1):118-23.

Yuan et al., Efficacy of orally administered methylnaltrexone in decreasing subjective effects after intravenous morphine. Drug Alcohol Depend. Oct. 1, 1998;52(2):161-5.

Yuan et al., Gastric effects of methylnaltrexone on mu, kappa, and delta opioid agonists induced brainstem unitary responses. Neuropharmacology. 1999 Mar;38(3):425-32.

Yuan et al., Gastric effects of mu-, delta- and kappa-opioid receptor agonists on brainstem unitary responses in the neonatal rat. Eur J Pharmacol. Oct. 24, 1996;314(1-2):27-32.

Yuan et al., Gut and brain effects of American ginseng root on brainstem neuronal activities in rats. Amer J Chin Med. 1998; 26: 47-55.

Yuan et al., Gut motility and transit changes in patients receiving long-term methadone maintenance. J Clin Pharmacol. Oct. 1998;38(10):931-5.

Yuan et al., Methylnaltrexone, a novel peripheral opioid receptor antagonist for the treatment of opioid side effects. Expert Opin Investig Drugs. May 2006;15(5):541-52.

Yuan et al., Methylnaltrexone (MNTX) for chronic opioid-induced constipation. 2002 ASCO Annual Meeting. Proc Am Soc Clin Oncol. 2002;21:376a. Abstract 1501.

Yuan et al., Methylnaltrexone (MNTX) reverses chronic opioid constipation: a double-blind, randomized, placebo-controlled trial. Anesthesiology. Sep. 1991; 91 (3A). Abstract A973.

Yuan et al., Methylnaltrexone changes gut motility and transit time in chronic methadone-maintained subjects. Anesth Analg. 1999;88: S1-424. Abstract S404.

Yuan et al., Methylnaltrexone effects on morphine-induced inhibition in isolated guinea-pig and human intestine. Clin Pharm & Therapeut. Feb. 1995;57:138. Abstract PI-11.

Yuan et al., Methylnaltrexone for reversal of constipation due to chronic methadone use: a randomized controlled trial. JAMA. Jan. 19, 2000;283(3):367-72.

Yuan et al., Methylnaltrexone prevents morphine-induced delay in oral-cecal transit time without affecting analgesia: a double-blind randomized placebo-controlled trial. Clin Pharmacol Ther. Apr. 1996;59(4):469-75.

Yuan et al., Methylnaltrexone prevents morphine-induced kaolin intake in the rat. Anesthesiology. 2003;99. Abstract A-922.

Yuan et al., Methylnaltrexone reduces oral-cecal transit time in humans. Dig Dis Week Abstr. 2003:A-578. Abstract T1840.

Yuan et al., Methylnaltrexone reverses morphine-induced changes in gastrointestinal motility: a clinical study. Anesthesiology Sep. 1995; 83(3A): Abstract A360.

Yuan et al., Methylnaltrexone: investigation of clinical applications. Drug Develop Res. 2000;50(2):133-41.

Yuan et al., Opioid analgesia without gut side effects: effects of methylnaltrexone as a novel peripheral opioid antagonist. Assoc Univ Anesth Abst. 2003: PD2.

Yuan et al., Oral methylnaltrexone for opioid-induced constipation. JAMA. Sep. 20, 2000;284(11):1383-4.

Yuan et al., Oral methylnaltrexone reverses chronic opioid-induced constipation. Anesthesiology. Sep. 2000;93(3A). Abstract A-872.

Yuan et al., Oral methylnaltrexone reverses morphine-induced changes in gastrointestinal motility. Anesthesiology. Sep. 1995;85(3A). Abstract A335.

Yuan et al., Pain control without side effects: clinical studies on methylnaltrexone as a novel peripheral opioid antagonist. $7^{th}$ America-Japan Anesth Congr. Yamanashi, Japan. 2002:41.

Yuan et al., Pharmacokinetics of intravenous vs. oral methylnaltrexone: evidence for direct gut effects. Anesth Analg. 2001;92: S1-363. Abstract S274.

Yuan et al., Safety and tolerance of oral methylnaltrexone in healthy volunteers. Anesth Analg. 1997;84:S1-599. Abstract S574.

Yuan et al., Subcutaneous methylnaltrexone prevents morphine-induced delay in gut transit time: a clinical trial. Anesthesiology. 2001;95. Abstract A-963.

Yuan et al., The safety and efficacy of oral methylnaltrexone in preventing morphine-induced delay in oral-cecal transit time. Clin Pharmacol Ther. Apr. 1997;61(4):467-75.

Yuan et al., Tolerability, gut effects, and pharmacokinetics of methylnaltrexone following repeated intravenous administration in humans. J Clin Pharmacol. May 2005;45(5):538-46.

Zagon et al., Opioids and differentiation in human cancer cells. Neuropeptides. Oct. 2005;39(5):495-505. Epub Sep. 15, 2005.

Zagon et al., Opioids and the apoptotic pathway in human cancer cells. Neuropeptides. Apr. 2003;37(2):79-88.

Zagon et al., Opioid antagonists inhibit the growth of metastatic murine neuroblastoma. Cancer Lett. Nov. 1983;21(1):89-94.

Zagon et al., Opioid growth factor regulates the cell cycle of human neoplasias. Int J Oncol. Nov. 2000;17(5):1053-61.

Zhang et al., Dynorphin A as a potential endogenous ligand for four members of the opioid receptor gene family. J Pharmacol Exp Ther. Jul. 1998;286(1):136-41.

Zhang et al., Effect of the endogenous kappa opioid agonist dynorphin A(1-17) on cocaine-evoked increases in striatal dopamine levels and cocaine-induced place preference in C57BL/6J mice. Psychopharmacology (Berl). Apr. 2004;172(4):422-9. Epub Jan. 8, 2004.

Zimmerman et al., Discovery of a potent, peripherally selective trans-3,4-dimethyl-4-(3-hydroxyphenyl) piperidine opioid antagonist for the treatment of gastrointestinal motility disorders. J Med Chem. Jul. 22, 1994 37(15):2262-5.

International Search Report and Written Opinion for PCT/US2009/059058 mailed Mar. 3, 2010.

PERIPHERAL OPIOID RECEPTOR ANTAGONISTS AND USES THEREOF

CROSS REFERENCE TO RELATED APPLICATIONS

The present application claims priority to U.S. provisional patent applications Ser. Nos. 61/101,201, filed Sep. 30, 2008, 61/226,581, filed Jul. 17, 2009, and 61/237,428, filed Aug. 27, 2009, the entirety of each of which is hereby incorporated herein by reference.

BACKGROUND OF THE INVENTION

Opioids are widely used in patients with advanced cancers and other terminal diseases to reduce suffering. Opioids are narcotic medications that activate opioid receptors located in the central nervous system to relieve pain. Opioids, however, also react with receptors outside of the central nervous system, resulting in side effects including constipation, nausea, vomiting, urinary retention, and severe itching. Most notable are the effects in the gastrointestinal tract (GI) where opioids inhibit gastric emptying and propulsive motor activity of the intestine, thereby decreasing the rate of intestinal transit and producing constipation. The effectiveness of opioids for pain is often limited due to resultant side effects, which can be debilitating and often cause patients to cease use of opioid analgesics.

In addition to analgesic opioid induced side effects, studies have suggested that endogenous opioid compounds and receptors may also affect activity of the gastrointestinal (GI) tract and may be involved in normal regulation of intestinal motility and mucosal transport of fluids in both animals and man. (Koch, T. R, et al, Digestive Diseases and Sciences 1991, 36, 712-728; Schuller, A. G. P., et al., Society of Neuroscience Abstracts 1998, 24, 524, Reisine, T., and Pasternak, G., Goodman & Gilman's The Pharmacological Basis of Therapeutics Ninth Edition 1996, 521-555 and Bagnol, D., et al., Regul. Pept. 1993, 47, 259-273). Thus, an abnormal physiological level of endogenous compounds and/or receptor activity may lead to bowel dysfunction.

For example, patients who have undergone surgical procedures, especially surgery of the abdomen, often suffer from a particular bowel dysfunction, called post-operative (or post-surgical) ileus, that may be caused by fluctuations in natural opioid levels. Similarly, women who have recently given birth commonly suffer from post-partum ileus, which is thought to be caused by similar natural opioid fluctuations as a result of birthing stress. Gastrointestinal dysfunction associated with post-operative or post partum ileus can typically last for 3 to 5 days, with some severe cases lasting more than a week. Administration of opioid analgesics to a patient after surgery, which is now an almost universal practice, may exacerbate bowel dysfunction, thereby delaying recovery of normal bowel function, prolonging hospital stays, and increasing medical care costs.

Methylnaltrexone ("MNTX") is a derivative of the opioid antagonist, naltrexone, whereby the amine is quarternized. MNTX is commonly provided as a salt, for example, a bromide salt. The bromide salt of MNTX is also known in the literature as: methylnaltrexone bromide; N-methylnaltrexone bromide; naltrexone methobromide; naltrexone methyl bromide; and MRZ 2663BR. MNTX was first reported by Goldberg et al. as described in U.S. Pat. No. 4,176,186. It is believed that addition of the methyl group to the ring nitrogen of naltrexone forms a charged compound with greater polarity and less liposolubility than naltrexone, preventing MNTX from crossing the blood-brain barrier in humans. As a consequence, MNTX exerts its effects in the periphery rather than in the central nervous system with the advantage that it does not counteract the analgesic effects of opioids on the central nervous system.

Generally, pharmaceutical compositions require a high level of purity to meet regulated standards for drug quality and purity. For example, during synthesis and/or storage of MNTX, impurities may form which may hinder the therapeutic effects of MNTX and/or may be toxic if present in high enough quantity. As such, it is desirable to have the ability to determine the purity of MNTX. To that end, it is important to identify, isolate, and chemically characterize impurities and degradants which can be used in chromatographic procedures as standards to confirm the purity of MNTX.

SUMMARY

In certain embodiments, the present invention relates to the identification, purification, and synthesis of an impurity of MNTX. It has been discovered that this compound can arise as an impurity either in the process for manufacturing MNTX or as a degradant when certain solutions of MNTX are stored under certain conditions. Accordingly, in certain embodiments, the present invention provides a compound of formula I:

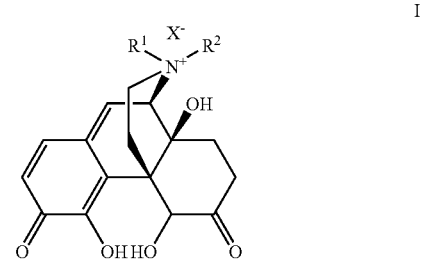

wherein $X^-$, $R^1$, and $R^2$ are as defined and described herein. In some embodiments, provided compounds are peripheral μ opioid receptor antagonists. Other uses of provided compounds are set forth infra.

The present invention also provides a prefilled syringe comprising a liquid composition comprising methylnaltrexone. In some embodiments, a prefilled syringe is substantially free of tungsten, or a derivative thereof. Such prefilled syringes, and uses thereof, are described in detail herein.

DETAILED DESCRIPTION OF CERTAIN EMBODIMENTS OF THE INVENTION

Figure 1:
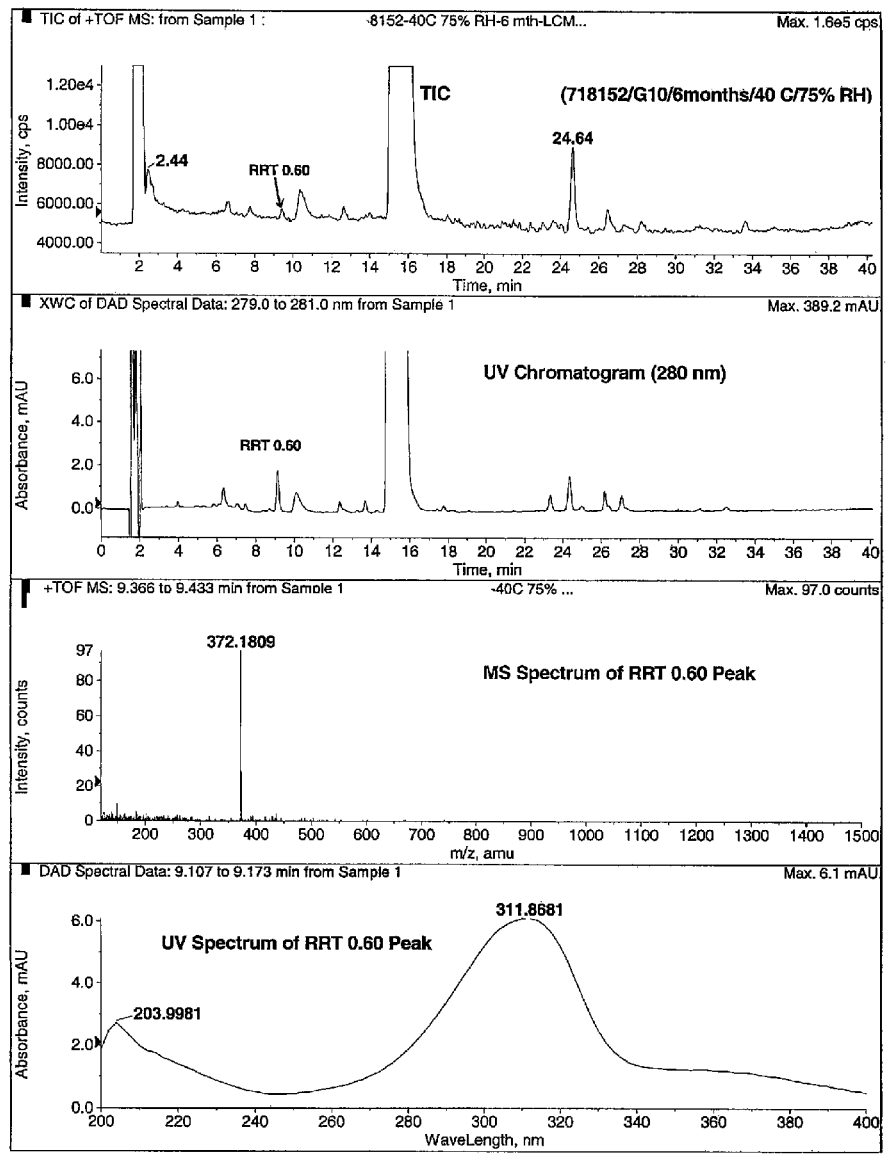
FIG. 1 depicts the LC/MS result of a stability study of a methylnaltrexone pre-filled syringe at 40° C. and 75% relative humidity after 6 months.

1. Compounds and Definitions:

In certain embodiments, the present invention provides a compound of formula I:

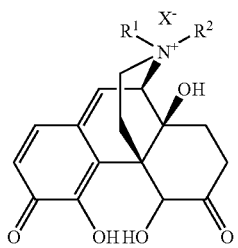

I wherein:
$R^1$ and $R^2$ are each independently $C_{1-6}$ aliphatic; and
$X^-$ is a suitable anion.

The term "aliphatic" or "aliphatic group", as used herein, means a straight-chain (i.e., unbranched) or branched hydrocarbon chain that is completely saturated or that contains one or more units of unsaturation, or a monocyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. In certain embodiments, an aliphatic group contains 1-4 aliphatic carbon atoms, and in yet other embodiments, an aliphatic group contains 1-3 aliphatic carbon atoms. In some embodiments, "cycloaliphatic" (or "carbocycle") refers to a monocyclic $C_3$-$C_6$ hydrocarbon that is completely saturated or that contains one or more units of unsaturation, but which is not aromatic, that has a single point of attachment to the rest of the molecule. Such cycloaliphatic groups include cycloalkyl, cycloalkenyl, and cycloalkynyl groups. Suitable aliphatic groups include, but are not limited to, linear or branched alkyl, alkenyl, alkynyl groups and hybrids thereof such as (cycloalkyl)alkyl, (cycloalkenyl)alkyl or (cycloalkyl)alkenyl. Exemplary aliphatic groups include allyl, vinyl, cyclopropylmethyl, methyl, ethyl, isopropyl, and the like.

The term "unsaturated," as used herein, means that a moiety has one or more units of unsaturation.

The term "lower alkyl," as used herein, refers to a hydrocarbon chain having up to 4 carbon atoms, preferably 1 to 3 carbon atoms, and more preferably 1 to 2 carbon atoms. The term "alkyl" includes, but is not limited to, straight and branched chains such as methyl, ethyl, n-propyl, isopropyl, n-butyl, isobutyl, sec-butyl, or t-butyl.

As used herein, an "effective amount" of a compound or pharmaceutically acceptable composition can achieve a desired therapeutic and/or prophylactic effect. In some embodiments, an "effective amount" is at least a minimal amount of a compound, or composition containing a compound, which is sufficient for treating one or more symptoms of a disorder or condition associated with modulation of peripheral μ opioid receptors, such as side effects associated with opioid analgesic therapy (e.g., gastrointestinal dysfunction (e.g., dysmotility constipation, etc.), nausea, emesis, (e.g., nausea), etc.). In certain embodiments, an "effective amount" of a compound, or composition containing a compound, is sufficient for treating one or more symptoms associated with, a disease associated with aberrant endogenous peripheral opioid or μ opioid receptor activity (e.g., idiopathic constipation, ileus, etc.).

The term "prefilled syringe" refers to a syringe that contains a drug product such as a solution of methylnaltrexone and is pre-packaged for use by a subject such as for self-administrationor administration by another such as a medical professional. In certain embodiments, a prefilled syringe is provided in a sterile package. In some embodiments, such a package contains a plurality of prefilled syringes.

The term "subject", as used herein, means a mammal and includes human and animal subjects, such as domestic animals (e.g., horses, dogs, cats, etc.).

The terms "suffer" or "suffering" as used herein refers to one or more conditions that a patient has been diagnosed with, or is suspected to have.

The terms "treat" or "treating," as used herein, refers to partially or completely alleviating, inhibiting, delaying onset of, preventing, ameliorating and/or relieving a disorder or condition, or one or more symptoms of the disorder or condition.

"Therapeutically active agent" or "active agent" refers to a substance, including a biologically active substance, that is useful for therapy (e.g., human therapy, veterinary therapy), including prophylactic and therapeutic treatment. Therapeutically active agents include organic molecules that are drug compounds, peptides, proteins, carbohydrates, monosaccharides, oligosaccharides, polysaccharides, nucleoprotein, mucoprotein, lipoprotein, synthetic polypeptide or protein, small molecules linked to a protein, glycoprotein, steroid, nucleic acid, DNA, RNA, nucleotide, nucleoside, oligonucleotides, antisense oligonucleotides, lipid, hormone, and vitamin. Therapeutically active agents include any substance used as a medicine for treatment, prevention, delay, reduction or amelioration of a disease, condition, or disorder. Among therapeutically active agents useful in the formulations of the present invention are opioid receptor antagonist compounds, opioid analgesic compounds, and the like. Further detailed description of compounds useful as therapeutically active agents is provided below. A therapeutically active agent includes a compound that increases the effect or effectiveness of a second compound, for example, by enhancing potency or reducing adverse effects of a second compound.

"Tungsten, or a derivative thereof" refers to tungsten, a salt thereof, an oxidized form thereof, or a tungsten-containing alloy. The term "tungsten" is used interchangeably with the phrase "tungsten, or a derivative thereof."

The expression "unit dosage form" as used herein refers to a physically discrete unit of inventive formulation appropriate for administration to a subject to be treated. It will be understood, however, that the total daily usage of the compositions of the present invention will be decided by the attending physician within the scope of sound medical judgment. The specific effective dose level for any particular subject or organism will depend upon a variety of factors including the disorder being treated and the severity of the disorder; activity of specific active agent employed; specific composition employed; age, body weight, general health, sex and diet of the subject; time of administration, and rate of excretion of the specific active agent employed; duration of the treatment; drugs and/or additional therapies used in combination or coincidental with specific compound(s) employed, and like factors well known in the medical arts.

2. Description of Exemplary Compounds:

As described generally above, the present invention provides a compound of formula I:

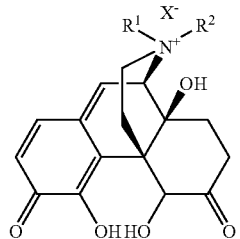

I wherein:

$R^1$ and $R^2$ are each independently $C_{1-6}$ aliphatic; and $X^-$ is a suitable anion.

One of ordinary skill in the art will recognize that the nitrogen atom depicted in formula I is a chiral center and, therefore, can exist in either the (R) or (S) configuration. According to one aspect, the present invention provides a compound of formula I wherein the compound is in the (R) configuration with respect to the nitrogen. In certain embodiments of the present invention, at least about 99.6%, 99.7%, 99.8%, 99.85%, 99.9%, or 99.95% of a compound of formula I is in the (R) configuration with respect to nitrogen.

As defined generally above, the $X^-$ group of formula I is a suitable anion. In certain embodiments, $X^-$ is the anion of a suitable Brønsted acid. Exemplary Brønsted acids include hydrogen halides, carboxylic acids, sulfonic acids, sulfuric acid, and phosphoric acid. In certain embodiments, $X^-$ is chloride, bromide, iodide, fluoride, sulfate, bisulfate, tartrate, nitrate, citrate, bitartrate, carbonate, phosphate, malate, maleate, fumarate sulfonate, methylsulfonate, formate, carboxylate, sulfate, methylsulfate or succinate salt. In certain embodiments, $X^-$ is trifluoroacetate. According to one aspect, $X^-$ is bromide.

It is readily apparent that a compound of formula I contains both a quaternized nitrogen group and a phenolic hydroxyl group. One of ordinary skill in the art will recognize that the phenolic hydroxyl group of a compound of formula I can form a salt with the quaternized nitrogen of a compound of formula I. Such salts can form between two molecules of a compound of formula I-a via an intermolecular interaction or can form between those groups of the same compound via an intramolecular interaction. The present invention contemplates both such salt forms. Thus, in certain embodiments, the present invention provides a compound of formula I-a:

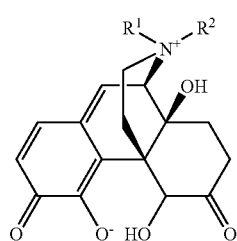

I-a wherein $R^1$ and $R^2$ are each independently $C_{1-6}$ aliphatic.

In some embodiments, the present invention provides a compound of formula I-b:

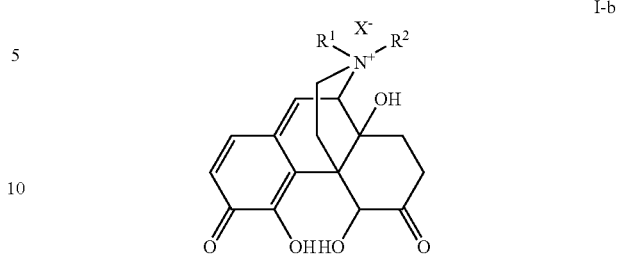

I-b wherein $R^1$ and $R^2$ are each independently $C_{1-6}$ aliphatic; and $X^-$ is a suitable anion.

In certain embodiments, the present invention provides a compound of formula I wherein $R^1$ is $C_{1-4}$ aliphatic and $R^2$ is lower alkyl. In other embodiments, the $R^1$ group is a (cycloalkyl)alkyl group or alkenyl group. According to certain embodiments, $R^1$ is cyclopropyl methyl or allyl. In other embodiments, $R^1$ is cyclopropyl methyl or allyl and $R^2$ is methyl. In some embodiments, $R^1$ is methyl and $R^2$ is cyclopropyl methyl or allyl.

According to one embodiment, the present invention provides a compound of formula II or II':

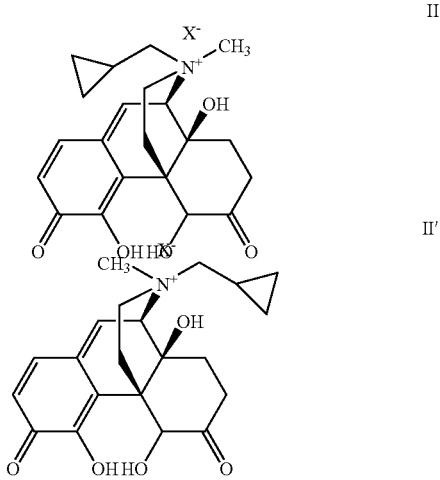

II

II' wherein each $X^-$ is a suitable anion as described herein.

In certain embodiments, the present invention provides compound II-a:

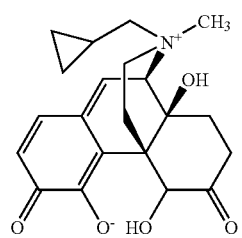

II-a

Exemplary compounds of formula II include compound II-1, II-2, and II-3:

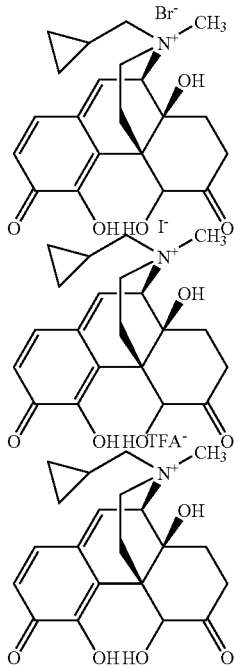

According to another aspect, the present invention provides a composition comprising:
(a) a compound of formula III or III':

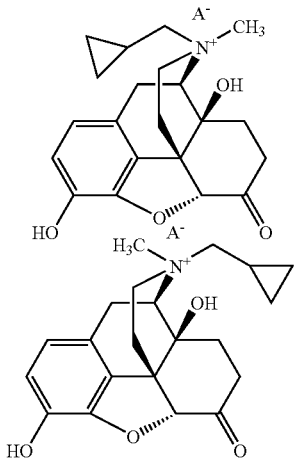

wherein A⁻ is a suitable anion,
(b) at least one compound of formula I:

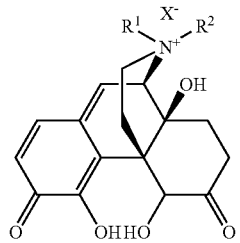

wherein:
$R^1$ and $R^2$ are each independently $C_{1-6}$ aliphatic; and
$X^-$ is a suitable anion; and
(c) optionally, a compound of formula IV:

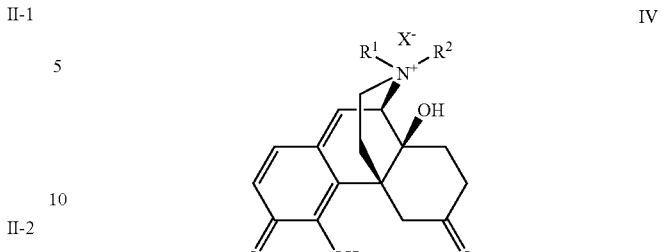

wherein:
$R^1$ and $R^2$ are each independently $C_{1-6}$ aliphatic; and
$X^-$ is a suitable anion.

In some embodiments, provided compositions are formulated for oral administration. In certain embodiments, a provided composition comprising a compound of formula III, a compound of formula I, and, optionally, a compound of formula IV is a solid composition wherein:
(a) at least about 99.6%, 99.7%, 99.8%, 99.85%, 99.9%, or 99.95% of the compound of formula III is in the (R) configuration with respect to nitrogen; and
(b) the compound of formula I is present in an amount of 60, 10, 5, 3.3, 2.5, 1 ppm or less.

In other embodiments, the present invention provides a composition comprising a compound of formula III, a compound of formula I, and a compound of formula IV, wherein the compounds of formula I and IV are present in amount of less than about 60, about 10, about 5, about 3.3, about 2.5, or about 1 ppm total. In some embodiments, provided solid formulations comprise from about 7% to about 75% or about 25% to about 65% or about 25% to about 55%. or about 40% to about 50% or about 20% to about 40% of a compound of formula III, based upon total weight of the solid formulation. In certain embodiments, provided solid formulations comprise from about 7%, about 8%, about 10%, about 20%, about 30%, about 40%, about 50%, about 60%, about 70%, or about 75% a compound of formula III, based upon total weight of the solid formulation.

In some embodiments, an oral solid formulation contains 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, or 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1025 mg, 1050 mg, 1075 mg, 1100 mg, 1125 mg, 1150 mg, 1175 mg, 1200 mg, 1225 mg, 1250 mg, 1275 mg, 1300 mg, 1325 mg, 1350 mg, 1375 mg, 1400 mg, 1425 mg, 1450 mg, 1475 mg, 1500 mg of a compound of formula III. In some embodiments, an oral solid formulation contains between 50 mg and 900 mg, inclusive, or between 150 mg and 450 mg, inclusive, of a compound of formula III. In some embodiments, an oral solid formulation contains 75 mg, 150 mg, 225 mg, 300 mg, 450 mg, 600 mg, or 900 mg of a compound of formula III. In certain embodiments, any such oral solid formulation wherein the compounds of formula I and IV are present in amount of less than about 60, about 10, about 5, about 3.3, about 2.5, or about 1 ppm total.

In some embodiments, the present invention provides a solid formulation for oral administration wherein said formulation comprises a compound of formula III, a compound of formula II, and optionally a compound of formula IV wherein the formulation provides no more than 1.5 micrograms of a compound of formula II per dose. In certain embodiments, the present invention provides a solid formulation for oral administration wherein said formulation comprises a compound of formula III, a compound of formula II, and a compound of formula IV wherein the formulation provides no more than 1.5 micrograms total of a compound of formula II and a compound of formula IV per dose.

In certain embodiments, such compositions are formulated in a liquid formulation. Such liquid formulations are described in detail in WO2008/019115, published Feb. 14, 2008, the entirety of which is hereby incorporated herein by reference. In some embodiments, the present invention provides a composition comprising a compound of formula III and a compound of formula I, where the amount of compound of formula I in the composition is less than about 25, about 100, about 125, about 150, about 185, about 187, or about 190 ppm. In some embodiments, the present invention provides a composition comprising a compound of formula III, a compound of formula I, and a compound of formula IV, wherein the compounds of formula I and IV are present in amount of less than about 25, about 100, about 125, about 150, about 185, about 187, or about 190 ppm total.

As defined generally above, the A⁻ group of formula III is a suitable anion. In certain embodiments, A⁻ is the anion of a suitable Brønsted acid. Exemplary Brønsted acids include hydrogen halides, carboxylic acids, sulfonic acids, sulfuric acid, and phosphoric acid. In certain embodiments, A⁻ is chloride, bromide, iodide, fluoride, sulfate, bisulfate, tartrate, nitrate, citrate, bitartrate, carbonate, phosphate, malate, maleate, fumarate sulfonate, methylsulfonate, formate, carboxylate, sulfate, methylsulfate or succinate salt. In certain embodiments, X⁻ is trifluoroacetate. According to one aspect, X⁻ is bromide.

It is readily apparent that a compound of formula III contains both a quaternized nitrogen group and a phenolic hydroxyl group. One of ordinary skill in the art will recognize that the phenolic hydroxyl group of a compound of formula III can form a salt with the quaternized nitrogen of a compound of formula III. Such salts can form between two molecules of a compound of formula III via an intermolecular interaction or can form between those groups of the same compound via an intramolecular interaction. The present invention contemplates both such salt forms.

International patent application publication number WO2006/127899 describes Compound III-1, (R)—N-methylnaltrexone bromide, which has the following structure:

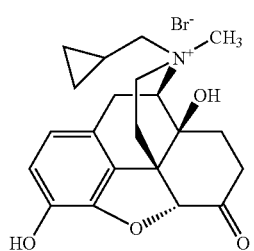

III-1 where the compound is in the (R) configuration with respect to the nitrogen. In certain embodiments of the present invention, at least about 99.6%, 99.7%, 99.8%, 99.85%, 99.9%, or 99.95% of Compound III-1 is in the (R) configuration with respect to nitrogen. Methods for determining the amount of (R)—N-methylnaltrexone bromide, present in a sample as compared to the amount of (S)—N-methylnaltrexone bromide present in that same sample, are described in detail in WO2006/127899, the entirety of which is hereby incorporated herein by reference. In other embodiments, Compound III-1 contains 0.15% or less (S)—N-methylnaltrexone bromide.

In certain embodiments, the present invention provides a compound of the present invention in isolated form. As used herein, the term "isolated" means that a compound is provided in a form that is separated from other components that might be present in that compound's usual environment (e.g., a reaction mixture, a chromatography eluent, a pharmaceutical composition, etc.). In certain embodiments, an isolated compound is in solid form. In some embodiments, an isolated compound is at least about 50% pure as determined by a suitable HPLC method. In certain embodiments, an isolated compound is at least about 60%, 70%, 80%, 90%, 95%, 98%, or 99% as determined by a suitable HPLC method.

In certain embodiments, the present invention provides a composition comprising: (a) a compound of formula III and/or III':

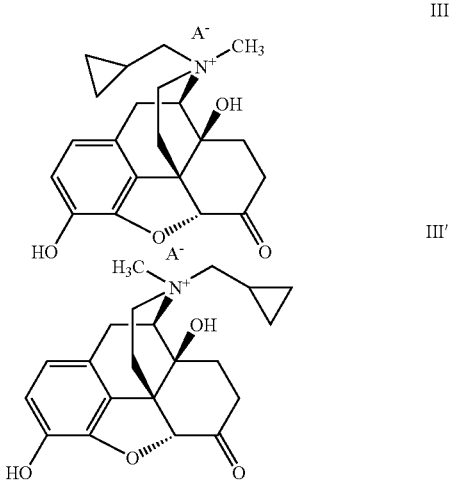

wherein A⁻ is a suitable anion, (b) at least one compound of formula II and/or II':

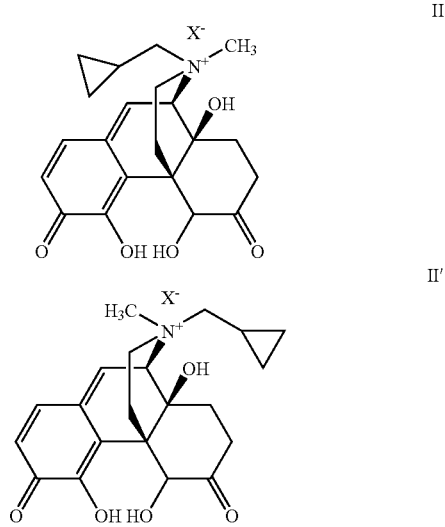

wherein X⁻ is a suitable anion as described herein; and
(c) optionally, a compound of formula IV-a and/or IV-a':

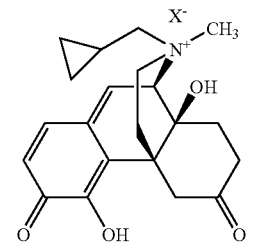

IV-a

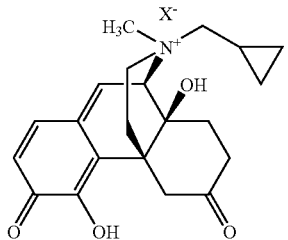

IV-a' wherein X⁻ is a suitable anion as described herein.

In certain embodiments, the present invention provides a solid composition comprising a compound of formula III, a compound of formula II, and, optionally, a compound of formula IV-a wherein:

(a) at least about 99.6%, 99.7%, 99.8%, 99.85%, 99.9%, or 99.95% of the compound of formula III is in the (R) configuration with respect to nitrogen; and (b) the compound of formula II is present in an amount of 60, 10, 5, 3.3, 2.5, 1 ppm or less.

In other embodiments, the present invention provides a composition comprising a compound of formula III, a compound of formula II, and, optionally, a compound of formula IV-a, wherein the compounds of formula II and IV-a are present in amount of less than about 60, about 10, about 5, about 3.3, about 2.5, or about 1 ppm total.

In certain embodiments, such compositions are formulated in a liquid formulation. In some embodiments, the present invention provides a liquid composition comprising a compound of formula III and a compound of formula II where the amount of compound of formula II in the composition is less than about 25, about 100, about 125, about 150, about 185, about 187, or about 190 ppm. In some embodiments, the present invention provides a composition comprising a compound of formula III, a compound of formula II, and, optionally, a compound of formula IV-a, wherein the compounds of formula II and IV-a, when present, are present in amount of less than about 25, about 100, about 125, about 150, about 185, about 187, or about 190 ppm total.

In other embodiments, the present invention provides a composition comprising: (a) compound III-1:

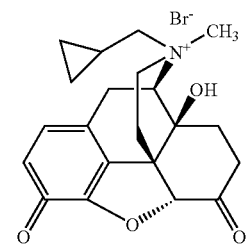

III-1

(b) compound II-1:

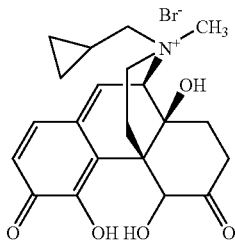

II-1 and (c) optionally, compound IV-1:

IV-1

In other embodiments, the present invention provides a solid composition comprising compound III-1, a II-1, and, optionally, compound IV-1, wherein at least about 99.6%, 99.7%, 99.8%, 99.85%, 99.9%, or 99.95% of the compound III-1 is in the (R) configuration with respect to nitrogen and compound II-1 is present in an amount of 60, 10, 5, 3.3, 2.5, 1 ppm or less. In other embodiments, the present invention provides a composition comprising compound III-1, compound II-1, and, optionally, compound IV-1, wherein the compounds II-1 and IV-1 are present in amount of less than about 60, about 10, about 5, about 3.3, about 2.5, or about 1 ppm total.

In some embodiments, the present invention provides a liquid composition comprising compound III-1 and compound II-1, wherein compound II-1 is present in amount of less than about 25, about 100, about 125, about 150, about 185, about 187, or about 190 ppm. In some embodiments, the present invention provides a liquid composition comprising compound III-1, compound II-1, and, optionally, compound IV-1, wherein the compounds II-1 and IV-1 are present in amount of less than about 25, about 100, about 125, about 150, about 185, about 187, or about 190 ppm total.

In certain embodiments, the present invention provides a prefilled syringe comprising a liquid composition comprising methylnaltrexone. Nonlimiting examples of such liquid compositions are described in detail in United States published patent application number US 2008-0070975, the entirety of which is hereby incorporated herein by reference. In some embodiments, the present invention provides a prefilled syringe comprising a unit dosage of a liquid composition which comprises methylnaltrexone or a pharmaceutically acceptable salt thereof, a calcium salt, and a chelating agent. In certain embodiments, the present invention provides a prefilled syringe, substantially free from tungsten, comprising a unit dosage of a liquid composition which comprises methylnaltrexone, a calcium chelating agent, and a buffering agent. In certain embodiments, the present invention provides a prefilled syringe, substantially free from tungsten, comprising a unit dosage of a liquid composition which comprises methylnaltrexone, a calcium chelating agent, a buffering agent, and an isotonicity agent. In some embodiments, the present invention provides a prefilled syringe, substantially free from tungsten, comprising a unit dosage of a liquid composition which comprises methylnaltrexone bromide, edetate calcium disodium, and glycine hydrochloride. In some embodiments, the present invention provides a prefilled syringe, substantially free from tungsten, comprising a unit dosage of a liquid composition which comprises methylnaltrexone bromide, edetate calcium disodium, glycine hydrochloride, and sodium chloride.

In certain embodiments, the liquid composition has a pH of between about pH 2.0 and about pH 6.0. In some embodiments, the pH of the formulation is between about pH 2.6 and about pH 5.0. In some embodiments, the pH of the formulation is between about pH 3.0 and about pH 4.0. In some embodiments, the pH of the formulation is between about pH 3.4 and about pH 3.6. In some embodiments, the pH of the formulation is about pH 3.5. In certain embodiments, the liquid composition has a pH of about 2.5 to about 6.

In some embodiments, the present invention provides a prefilled syringe comprising a liquid composition comprising methylnaltrexone in an amount from about 0.5 mg to about 200 mg, about 1 mg to about 80 mg, from about 5 mg to about 40 mg, or methylnaltrexone bromide in an amount of about 8 mg, about 12 mg, about 16 mg, about 18 mg, or about 24 mg.

In some embodiments, the present invention provides a prefilled syringe comprising a liquid composition comprising methylnaltrexone and a chelating agent in an amount from about 0.01 mg/mL to about 2 mg/mL or about 0.1 mg/mL to about 1 mg/mL in the formulation, or about 0.2 mg/mL to about 0.8 mg/mL of the formulation. In some embodiments, a chelating agent may be present in an amount from about 0.2 mg/mL, about 0.3 mg/mL, about 0.4 mg/mL, about 0.5 mg/mL, or about 0.6 mg/mL, in the formulation.

Exemplary chelating agents include ethylenediaminetetraacetic acid (also synonymous with EDTA, edetic acid, versene acid, and sequestrene), and EDTA derivatives, such as sodium EDTA, and potassium EDTA, diammonium EDTA, dipotassium EDTA, disodium EDTA, TEA-EDTA, tetrasodium EDTA, tripotassium EDTA, trisodium EDTA, HEDTA, and trisodium HEDTA, and related salts thereof. Other chelating agents include niacinamide and derivatives thereof and sodium desoxycholate and derivatives thereof, ethylene glycol-bis-(2-aminoethyl)-N,N,N',N'-tetraacetic acid (EGTA) and derivatives thereof, diethylenetriaminepentaacetic acid (DTPA) and derivatives thereof, N,N-bis(carboxymethyl)glycine (NTA) and derivatives thereof, nitrilotriacetic acid and derivatives thereof. Still other chelating agents include citric acid and derivatives thereof. Citric acid also is known as citric acid monohydrate. Derivatives of citric acid include anhydrous citric acid and trisodiumcitrate-dihydrate. In some embodiments, chelating agent is selected from EDTA or an EDTA derivative or EGTA or an EGTA derivative. In some embodiments chelating agent is EDTA disodium such as, for example, EDTA disodium hydrate.

In some embodiments, the present invention provides a prefilled syringe comprising a liquid composition comprising methylnaltrexone and a calcium salt in an amount from about 0.01 mg/mL to about 2 mg/mL or about 0.1 mg/mL to about 1 mg/mL, or about 0.2 mg/mL to about 0.8 mg/mL, about 0.2 mg/mL, about 0.3 mg/mL, about 0.4 mg/mL, about 0.5 mg/mL, or about 0.6 mg/mL.

Examplary of calcium salts include, but are not limited to calcium chloride, calcium acetate, calcium citrate, calcium sulfate, etc.

In some embodiments, the present invention provides a prefilled syringe comprising a liquid composition comprising methylnaltrexone and a calcium salt chelating agent in an amount from about 0.01 mg/mL to about 2 mg/mL or about 0.1 mg/mL to about 1 mg/mL, or about 0.2 mg/mL to about 0.8 mg/mL. In some embodiments, calcium salt chelating agent may be present in an amount from about 0.2 mg/mL, about 0.3 mg/mL, about 0.4 mg/mL, about 0.5 mg/mL, or about 0.6 mg/mL.

Common calcium salt chelating agents include, but are not limited to calcium ethylenediaminetetra acetic acid (EDTA) and calcium salt EDTA derivatives, calcium ethylene glycol-bis-(2-aminoethyl)-N,N,N',N'-tetraacetic acid (EGTA) and calcium salt EGTA derivatives, calcium diethylenetriaminepentaacetic acid (DTPA) and calcium salt DTPA derivatives, calcium N,N-bis(carboxymethyl)glycine (NTA) and calcium salt NTA derivatives, and calcium citrate and derivatives thereof. In some embodiments, chelating agent is selected from calcium EDTA or a calcium salt EDTA derivative or calcium EGTA or a calcium salt EGTA derivative. In some embodiments chelating agent is calcium EDTA disodium such as, for example, calcium EDTA disodium hydrate.

In some embodiments, the present invention provides a prefilled syringe comprising a liquid composition comprising methylnaltrexone and an isotonic agent. Common isotonic agents include agents selected from the group consisting of sodium chloride, mannitol, lactose, dextrose (hydrous or anhydrous), sucrose, glycerol, and sorbitol, and solutions thereof.

In some embodiments, the present invention provides a prefilled syringe comprising a liquid composition comprising methylnaltrexone and a stabilizing agent in an amount from about 0.01 mg/mL to about 2 mg/mL or about 0.05 mg/mL to about 1 mg/mL, or about 0.1 mg/mL to about 0.8 mg/mL. In some embodiments, stabilizing agent may be present in an amount from about 0.15 mg/mL, about 0.2 mg/mL, about 0.25 mg/mL, about 0.3 mg/mL, about 0.35 mg/mL, or about 0.4 mg/mL.

Exemplary stabilizing agents include glycine, benzoic acid, citric, glycolic, lactic, malic, and maleic acid. In some embodiments, the formulation comprises glycine. In some embodiments, glycine comprises glycine-HCl.

In certain embodiments, the present invention provides a prefilled syringe comprising a liquid composition comprising a compound of formula III and a compound of formula II, wherein the compound of formula II is present in amount of less than about 25, about 100, about 125, about 150, about 185, about 187, or about 190 ppm. In some embodiments, the present invention provides a liquid composition comprising a compound of formula III, a compound of formula II, and, optionally, a compound of formula IV, wherein the compounds of formulae II and IV are present in amount of less than about 25, about 100, about 125, about 150, about 185, about 187, or about 190 ppm total.

In some embodiments, a syringe, for use in preparing prefilled syringes in accordance with the present invention, is "tungsten free" or "substantially free" from tungsten. In some embodiments, a "tungsten free" or substantially free from tungsten syringe is commercially available from Becton Dickinson, Schott, and others. Such syringes may be referred to as "Ultra Low" Tungsten Syringes or "tungsten free".

In certain embodiments, "substantially free" from tungsten means a level of tungsten less than an amount that contributes to degradation of a compound of formula III. In certain embodiments, a syringe that is substantially free from tungsten contains tungsten in an amount of less than about 60 parts per billion, or less than about 50 parts per billion, or less than about 40 parts per billion. In some embodiments, a syringe that is substantially free from tungsten contains tungsten in an amount of less than about 12 parts per billion. It will be appreciated that syringes designated as "substantially free" from tungsten include those that are tungsten free. Levels of tungsten in the syringe can be measured by variety of techniques known to those skilled in the art such as those described in US 20080103438 and, in more detail, in Example 8, infra.

In some embodiments a syringe for use in preparing prefilled syringes in accordance with the present invention is a prefillable glass and/or polymer syringe. Such syringes are commercially available, for example, from Schott. In some embodiments, the polymer syringe is made of cycloolefin polymer.

Without wishing to be bound by any particular theory, it is believed that the presence of tungsten in a syringe contributes to the degradation of methylnaltrexone solution stored in such a syringe. Such degradation includes formation of a compound of formula I. Thus, in some aspects of the present invention, a methylnaltrexone solution is stored in a manner whereby the solution is isolated from tungsten (i.e., methylnaltrexone is not in contact with tungsten). In certain embodiments, the present invention provides a methylnaltrexone prefilled syringe that is free from tungsten, or a derivative thereof, or contains tungsten in an amount of less than about 60 parts per billion or less than about 50 parts per billion or less than about 40 parts per billion or less than about 12 parts per billion. Levels of tungsten can be measured for example by ICP-MS.

In certain embodiments, the present invention provides a prefilled syringe, substantially free from tungsten, comprising a liquid composition comprising compound III-1 and compound II-1, wherein compound II-1 is present in amount of less than about 25, about 100, about 125, about 150, about 185, about 187, or about 190 ppm. In some embodiments, the present invention provides a prefilled syringe, substantially free from tungsten, liquid composition comprising compound III-1, compound II-1, and, optionally, compound IV-1, wherein the compounds II-1 and IV-1 are present in amount of less than about 25, about 100, about 125, about 150, about 185, about 187, or about 190 ppm total.

In some embodiments, the present invention provides a prefilled syringe, substantially free from tungsten, comprising a liquid composition comprising about 8 mg of compound III-1 in about 0.4 mL water, and compound II-1, wherein compound II-1 is present in amount of less than about 25, about 100, about 125, about 150, about 185, about 187, or about 190 ppm. In certain embodiments, the present invention provides a prefilled syringe, substantially free from tungsten, comprising: (a) 8 mg of compound III-1; (b) 0.16 mg edetate calcium disodium; and (c) 0.12 mg glycine hydrochloride, wherein said prefilled syringe comprises compound II-1 in an amount of less than about 25, about 100, about 125, about 150, about 185, about 187, or about 190 ppm. In certain embodiments, the present invention provides a prefilled syringe, substantially free from tungsten, comprising: (a) 8 mg of compound III-1; (b) 0.4 mL water; (c) 2.6 mg sodium chloride; (d) 0.16 mg edetate calcium disodium; and (e) 0.12 mg glycine hydrochloride, wherein said prefilled syringe comprises compound II-1 in an amount of less than about 25, about 100, about 125, about 150, about 185, about 187, or about 190 ppm.

In some embodiments, the present invention provides a prefilled syringe, substantially free from tungsten, comprising a liquid composition comprising about 12 mg of compound III-1 in about 0.6 mL water, and compound II-1, wherein compound II-1 is present in amount of less than about 25, about 100, about 125, about 150, about 185, about 187, or about 190 ppm. In certain embodiments, the present invention provides a prefilled syringe, substantially free from tungsten, comprising: (a) 12 mg of compound III-1; (b) 0.24 mg edetate calcium disodium; and (c) 0.18 mg glycine hydrochloride, wherein said prefilled syringe comprises compound II-1 in an amount of less than about 25, about 100, about 125, about 150, about 185, about 187, or about 190 ppm. In certain embodiments, the present invention provides a prefilled syringe, substantially free from tungsten, comprising: (a) 12 mg of compound III-1; (b) 0.6 mL water; (c) 3.9 mg sodium chloride; (d) 0.24 mg edetate calcium disodium; and (e) 0.18 mg glycine hydrochloride, wherein said prefilled syringe comprises compound II-1 in an amount of less than about 25, about 100, about 125, about 150, about 185, about 187, or about 190 ppm.

In some embodiments, one or more provided prefilled syringes that are substantially free from tungsten and contains methylnaltrexone, as described herein, are stored in a container that shields the syringe from light. In certain embodiments, one or more prefilled syringes are stored in a blister pack which shields the syringes from light. In some embodiments, one or more prefilled syringes are stored in a box which shields the syringe from light.

In some embodiments, a prefilled syringe, that is substantially free from tungsten and contains methylnaltrexone, as described herein, provides a unit dosage of methylnaltrexone that is stable to degradation under typical ambient storage conditions for at least 9 months or at least 12 months, or at least 18 months or at least 24 months. As used herein, the term "typical ambient storage conditions" refers to 25° C./60% RH. In certain embodiments, the present invention provides a prefilled syringe, as described herein, wherein said prefilled syringe comprises compound II-1 in an amount of less than about 25 ppm for at least 9 months, at least 12 months, at least 14 months, at least 16 months, at least 18 months, or at least 24 months. In certain embodiments, the present invention provides a prefilled syringe, as described herein, wherein said prefilled syringe comprises compounds II-1 and/or IV-1 in an amount of less than about 25, about 100, about 125, about 150, about 185, about 187, or about 190 ppm total for at least 9 months, at least 12 months, at least 14 months, at least 16 months, at least 18 months, or at least about 24 months.

In certain embodiments, the present invention provides compound II-1 as a crystalline solid. In some embodiments, compound II-1 is provided as an amorphous solid.

As used herein, the term "substantially free of amorphous compound II-1" means that the crystalline solid contains no significant amount of amorphous compound II-1. In certain embodiments of the present invention, the term "substantially free of amorphous compound II-1" means that at least about 95% by weight of compound II-1 in the solid is in crystalline form. In certain embodiments of the invention, the term "substantially free of amorphous compound II-1" means that at least about 99% by weight of Compound 1 in the solid is in crystalline form.

As used herein, the term "substantially free of other forms of compound II-1" means that the solid contains no significant amount of another solid form of compound II-1. In certain embodiments of the present invention, the term "substantially free of other forms of compound II-1" means that at least about 95% by weight of compound II-1 is in the specified solid form. In certain embodiments of the invention, the term "substantially free of another form of compound II-1" means that at least about 99% by weight of compound II-1 is in the specified solid form.

The powder XRD of compound II-1 polymorph contained peaks at 9.8, 10.8, 12.7, 14.7, 15.0, 15.9, 16.7, 17.5, 18.7, 19.4, 20.5, 21.0, 21.7, 22.6, 23.0, 24.3, 24.8, 25.5, 25.9, 26.8, 27.2, 28.2, 28.8, 29.5, 30.1, 31.2, 32.1, 32.9, 33.5, 34.9, 36.0 and 38.5 degrees 2 theta. In certain embodiments, the present invention provides a crystalline form of compound II-1 characterized in that said form has one or more peaks in its powder X-ray diffraction pattern selected from 9.8, 10.8, 12.7, 14.7, 15.0, 15.9, 16.7, 17.5, 18.7, 19.4, 20.5, 21.0, 21.7, 22.6, 23.0, 24.3, 24.8, 25.5, 25.9, 26.8, 27.2, 28.2, 28.8, 29.5, 30.1, 31.2, 32.1, 32.9, 33.5, 34.9, 36.0 and 38.5 degrees 2 theta. In certain embodiments, the present invention provides a crystalline form of compound II-1 characterized in that said form has two or more peaks in its powder X-ray diffraction pattern selected from 9.8, 10.8, 12.7, 14.7, 15.0, 15.9, 16.7, 17.5, 18.7, 19.4, 20.5, 21.0, 21.7, 22.6, 23.0, 24.3, 24.8, 25.5, 25.9, 26.8, 27.2, 28.2, 28.8, 29.5, 30.1, 31.2, 32.1, 32.9, 33.5, 34.9, 36.0 and 38.5 degrees 2 theta. In certain embodiments, the present invention provides a crystalline form of compound II-1 characterized in that said form has substantially all of the peaks in its powder X-ray diffraction pattern selected from 9.8, 10.8, 12.7, 14.7, 15.0, 15.9, 16.7, 17.5, 18.7, 19.4, 20.5, 21.0, 21.7, 22.6, 23.0, 24.3, 24.8, 25.5, 25.9, 26.8, 27.2, 28.2, 28.8, 29.5, 30.1, 31.2, 32.1, 32.9, 33.5, 34.9, 36.0 and 38.5 degrees 2 theta.

Figure 15:
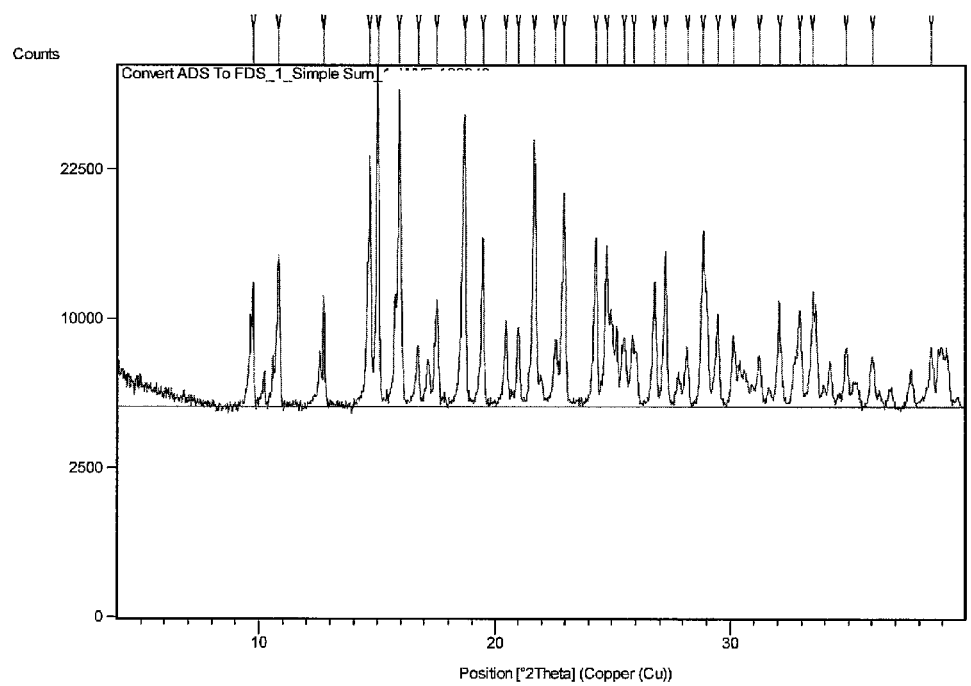
FIG. 15 depicts the X-ray diffraction pattern of crystalline compound II-1.

According to one aspect, compound II-1 polymorph has an XRD pattern containing substantially all of the peaks depicted in FIG. 15. As used herein, the phrase "substantially all of the peaks" means that the compound exhibits, in its XRD, at least about 80% of the peaks listed. In other embodiments, the phrase "substantially all of the peaks" means that the compound exhibits, in its XRD, at least about 85, 90, 95, 97, 98, or 99% of the peaks listed.

According to another embodiment, the present invention provides compound II-1 as an amorphous solid. Amorphous solids are well known to one of ordinary skill in the art and are typically prepared by such methods as lyophilization, melting, and precipitation from supercritical fluid, among others. Methods of preparing amorphous compound II-1 are described in the Examples section, infra.

In certain embodiments, the present invention provides amorphous compound II-1 substantially free of crystalline compound II-1. As used herein, the term "substantially free of crystalline compound II-1" means that the compound contains no significant amount of crystalline compound II-1. In certain embodiments of the present invention, at least about 95% by weight of compound II-1 present is amorphous compound II-1. In still other embodiments of the invention, at least about 99% by weight of compound II-1 present is amorphous compound II-1.

In other embodiments, the present invention provides a composition comprising amorphous compound II-1 and at least one crystalline form of compound II-1. Such crystalline forms of compound II-1 include compound II-1 polymorph as described herein or other crystalline forms of compound II-1 that may result from the preparation of, and/or isolation of, amorphous compound II-1. In certain embodiments, the present invention provides a composition comprising amorphous compound II-1 and at least one crystalline form of compound II-1 as described herein.

In some embodiments, the present invention provides a method comprising the steps of:
(a) providing a compound of formula III:

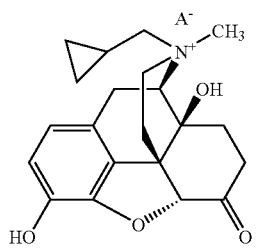

wherein A⁻ is a suitable anion; and
(b) treating the compound of formula III with an oxidizing agent to form a compound of formula II:

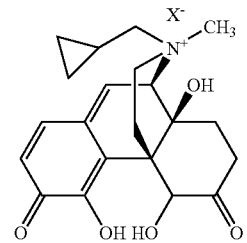

wherein X⁻ is a suitable anion.

Oxidizing agents suitable for the reaction with a compound of formula III to form a compound of formula II are well known to one of ordinary skill in the art. In some embodiments, the oxidizing agent is a peroxide, a benzoquinone, or a peracid. In certain embodiments, the oxidizing agent is hydrogen peroxide, t-butyl hydrogen peroxide, MCPBA (meta-chloroperbenzoic acid), peracetic acid, oxone (potassium peroxymonosulfate), or DDQ (2,3-dichloro-5,6-dicyanobenzoquinone).

In certain embodiments, the present invention provides a method comprising the steps of:
(a) providing compound III-1:

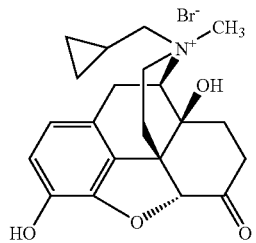

and
(b) treating the compound III-1 with an oxidizing agent to form compound II-1:

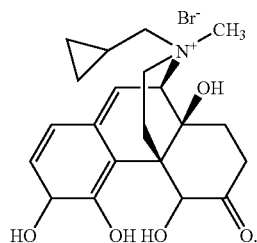

In some embodiments, the method for preparing compound II-1 from III-1, via oxidation reaction, further comprises the step of performing a salt exchange to afford compound II-3:

One of ordinary skill in the art will appreciate that compound II-3 is readily prepared from compound II-1 by, for example, HPLC purification utilizing an eluent that contains trifluoroacetic acid.

4. Uses, Formulation and Administration

Compound II-1 was identified as a new degradation product of (R)—N-methylnaltrexone bromide. Specifically, a stability study performed on (R)—N-methylnaltrexone bromide pre-filled syringes resulted in a new, unknown impurity. This impurity was identified by LC/MS as a new peak eluting at RRT 0.60. The peak was isolated by preparative HPLC, as detailed at Example 1. One of ordinary skill in the art would recognize that the compound of formula II isolated from the preparative HPLC, using the solvent eluent as described in the Exemplification, was the trifluoroacetic acid salt, compound II-3. In addition, compound II-1 was synthesized to confirm its structural identity. Thus, compounds of the present invention are useful as analytical standards for use in determining the purity of (R)—N-methylnaltrexone bromide as an active pharmaceutical ingredient.

In certain embodiments, the present invention provides a method comprising the steps of:
(a) providing a sample of (R)—N-methylnaltrexone bromide;
(b) performing an analysis of the sample of (R)—N-methylnaltrexone bromide; and
(c) determining the amount of compound II-1 in the sample of (R)—N-methylnaltrexone bromide.

In certain embodiments, the present invention provides a method comprising the steps of:
(a) providing a sample of (R)—N-methylnaltrexone bromide;
(b) performing an analysis of the sample of (R)—N-methylnaltrexone bromide; and
(c) determining the amount of compound II-1 and compound IV in the sample of (R)—N-methylnaltrexone bromide.

In certain embodiments, the present invention provides a method comprising the steps of:
(a) providing a sample of (R)—N-methylnaltrexone bromide;
(b) providing a sample of compound II-1; and
(c) performing HPLC analysis of the sample of (R)—N-methylnaltrexone bromide and the sample of compound II-1; and
(d) determining the amount of compound II-1 in the sample of (R)—N-methylnaltrexone bromide.

In certain embodiments, step (d) comprises determining that the amount of compound II-1 (or compound II-3, as appropriate) in the sample of (R)—N-methylnaltrexone bromide is less than about 60 ppm, about 10 ppm, about 5 ppm, about 3.3 ppm, about 2.5 ppm, or about 1.0 ppm. In some embodiments, step (d) comprises determining that the amount of compound II-1 (or compound II-3, as appropriate) in the sample of (R)—N-methylnaltrexone bromide is less than about 25, about 100, about 125, about 150, about 185, about 187, or about 190 ppm.

In some embodiments, the present invention provides a method comprising the steps of:
(a) providing an HPLC chromatogram of a sample of (R)—N-methylnaltrexone bromide;
(b) providing an HPLC chromatogram of a sample of compound II-1;
(c) comparing the HPLC chromatograms and determining the amount of compound II-1 in the sample of (R)—N-methylnaltrexone bromide.

In certain embodiments, step (c) comprises determining that the amount of compound II-1 (or compound II-3, as appropriate) in the sample of (R)—N-methylnaltrexone bromide is less than about 60 ppm, about 10 ppm, about 5 ppm, about 3.3 ppm, about 2.5 ppm, or about 1.0 ppm. In some embodiments, step (c) comprises determining that the amount of compound II-1 (or compound II-3, as appropriate) in the sample of (R)—N-methylnaltrexone bromide is less than about 25, about 100, about 125, about 150, about 185, about 187, or about 190 ppm.

In certain embodiments, step (b) further comprises providing a sample of compound IV-1 and step (c) further comprises determining the amount of compound IV-1 in the sample of (R)—N-methylnaltrexone bromide. In certain embodiments, step (c) comprises determining that the amount of compound II-1 and compound IV-1 in the sample of (R)—N-methylnaltrexone bromide is less than about 60 ppm, about 10 ppm, about 5 ppm, about 3.3 ppm, about 2.5 ppm, or about 1 ppm total. In certain embodiments, step (c) comprises determining that the amount of compound II-1 and compound IV-1 in the sample of (R)—N-methylnaltrexone bromide is less than about 25, about 100, about 125, about 150, about 185, about 187, or about 190 ppm.

In some embodiments, step (c) comprises determining that the sample of (R)—N-methylnaltrexone bromide provides no more than 1.5 micrograms of compound II-1 and compound IV-1 per dose (i.e., per day).

In certain embodiments, compounds of the present invention are useful for the study of peripheral mu opioid antagonists in biological and pathological phenomena and the comparative evaluation of peripheral mu opioid antagonists.

In certain embodiments, a compound of formula I is useful as a peripheral mu opioid receptor antagonist. According to another aspect of the present invention, pharmaceutically acceptable compositions are provided, comprising a compound of formula I, as described herein, and optionally comprising a pharmaceutically acceptable carrier, adjuvant, or vehicle. In certain embodiments of the present invention, such pharmaceutically acceptable compositions optionally further comprise one or more additional therapeutic agents.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remingtons Pharmaceutical Sciences,* 17th edition, ed. Alfonoso R. Gennaro, Mack Publishing Company, Easton, Pa. (1985) discloses various carriers used in formulating pharmaceutically acceptable compositions and known techniques for the preparation thereof. Except insofar as any conventional carrier medium is incompatible with the salt of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In certain embodiments, the invention relates to compositions comprising at least one compound of formula I and one or more pharmaceutically acceptable carriers, excipients, or diluents. Such compositions are prepared in accordance with acceptable pharmaceutical procedures, such as, for example, those described in *Remingtons*, which is incorporated herein by reference in its entirety. Pharmaceutically acceptable carriers are those carriers that are compatible with the other ingredients in the formulation and are biologically acceptable.

The compositions of the present invention are administered orally or parenterally, neat, or in combination with conventional pharmaceutical carriers. Applicable solid carriers can include one or more substances that can also act as flavoring agents, lubricants, solubilizers, suspending agents, fillers, glidants, compression aids, binders, tablet-disintegrating agents, or encapsulating materials. In powders, the carrier is a finely divided solid that is in admixture with the finely divided active ingredient. In tablets, the active ingredient is mixed with a carrier having the necessary compression properties in suitable proportions and compacted in the shape and size desired. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers can be used in preparing solutions, suspensions, emulsions, syrups and elixirs. The active ingredient can be dissolved or suspended in a pharmaceutically acceptable liquid carrier such as water, an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form.

In certain embodiments, the compositions of the present invention are administered rectally or vaginally in the form of a conventional suppository. For administration by intranasal or intrabronchial inhalation or insufflation, the compositions of the present invention can be formulated into an aqueous or partially aqueous solution, which can then be utilized in the form of an aerosol. The compositions of the present invention can also be administered transdermally through the use of a transdermal patch containing the active compound and a carrier that is inert to the active compound, is non-toxic to the skin, and allows delivery of the agent for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable. A variety of occlusive devices can be used to release the active ingredient into the blood stream such as a semipermeable membrane covering a reservoir containing the active ingredient with or without a carrier, or a matrix containing the active ingredient. Other occlusive devices are known in the literature.

In some embodiments, the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The amount of composition of the present invention provided to a subject will vary depending upon what is being administered, the purpose of the administration, such as prophylaxis or therapy, the state of the subject, the manner of administration, and the like. In therapeutic applications, compositions of the present invention are provided to a subject suffering from a condition in an amount sufficient to treat or at least partially treat the symptoms of the condition and its complications. An amount adequate to accomplish this is a "therapeutically effective amount" as described previously herein. The dosage to be used in the treatment of a specific case must be subjectively determined by the attending physician. The variables involved include the specific condition and the size, age, and response pattern of the subject. The treatment of substance abuse follows the same method of subjective drug administration under the guidance of the attending physician. Generally, a starting dose is about 5 mg per day with gradual increase in the daily dose to about 150 mg per day, to provide the desired dosage level in the subject.

In some embodiments, the present invention provides a method comprising administering to a subject an 8 mg or 12 mg dose of a compound of formula III via subcutaneous injection. In certain embodiments, the present invention provides a method comprising the steps of:

(i) providing a prefilled syringe, substantially free from tungsten, comprising a unit dosage of a liquid composition comprising 8 mg of compound III-1 and compound II-1, wherein compound II-1 is present in amount of less than about 25, about 100, about 125, about 150, about 185, about 187, or about 190 ppm and/or where the amount of compound II-1 and compound IV-1 is present in amount of less than about 25, about 100, about 125, about 150, about 185, about 187, or about 190 ppm in total;

(ii) administering the unit dosage to a subject via subcutaneous injection.

In certain embodiments, the present invention provides a method comprising the steps of:
(i) providing a prefilled syringe, substantially free from tungsten, comprising a unit dosage of a liquid composition comprising 8 mg of compound III-1 in 0.4 mL water, and compound II-1, wherein compound II-1 is present in amount of less than about 25, about 100, about 125, about 150, about 185, about 187, or about 190 ppm and/or where the amount of compound II-1 and compound IV-1 is present in amount of less than about 25, about 100, about 125, about 150, about 185, about 187, or about 190 ppm in total;
(ii) administering the unit dosage to a subject via subcutaneous injection.

In certain embodiments, the present invention provides a method comprising the steps of:
(i) providing a prefilled syringe, substantially free from tungsten, comprising a unit dosage of a liquid composition comprising: (a) 8 mg of compound III-1; (b) 0.16 mg edetate calcium disodium; and (c) 0.12 mg glycine hydrochloride, wherein said prefilled syringe comprises compound II-1 in an amount of less than about 25, about 100, about 125, about 150, about 185, about 187, or about 190 ppm and/or where the amount of compound II-1 and compound IV-1 is present in amount of less than about 25, about 100, about 125, about 150, about 185, about 187, or about 190 ppm in total;
(ii) administering the unit dosage to a subject via subcutaneous injection.

In certain embodiments, the present invention provides a method comprising the steps of:
(i) providing a prefilled syringe, substantially free from tungsten, comprising a unit dosage of a composition comprising: (a) 8 mg of compound III-1; (b) 0.4 mL water; (c) 2.6 mg sodium chloride; (d) 0.16 mg edetate calcium disodium; and (e) 0.12 mg glycine hydrochloride, wherein said prefilled syringe comprises compound II-1 in an amount of less than about 25, about 100, about 125, about 150, about 185, about 187, or about 190 ppm and/or where the amount of compound II-1 and compound IV-1 is present in amount of less than about 25, about 100, about 125, about 150, about 185, about 187, or about 190 ppm in total;
(ii) administering the unit dosage to a subject via subcutaneous injection.

In certain embodiments, the present invention provides a method comprising the steps of:
(i) providing a prefilled syringe, substantially free from tungsten, comprising a unit dosage of a liquid composition comprising 12 mg of compound III-1 and compound II-1, wherein compound II-1 is present in amount of less than about 25, about 100, about 125, about 150, about 185, about 187, or about 190 ppm and/or where the amount of compound II-1 and compound IV-1 is present in amount of less than about 25, about 100, about 125, about 150, about 185, about 187, or about 190 ppm in total;
(ii) administering the unit dosage to a subject via subcutaneous injection.

In certain embodiments, the present invention provides a method comprising the steps of:
(i) providing a prefilled syringe, substantially free from tungsten, comprising a unit dosage of a liquid composition comprising 12 mg of compound III-1 in 0.6 mL water, and compound II-1, wherein compound II-1 is present in amount of less than about 25, about 100, about 125, about 150, about 185, about 187, or about 190 ppm and/or where the amount of compound II-1 and compound IV-1 is present in amount of less than about 25, about 100, about 125, about 150, about 185, about 187, or about 190 ppm in total;
(ii) administering the unit dosage to a subject via subcutaneous injection.

In certain embodiments, the present invention provides a method comprising the steps of:
(i) providing a prefilled syringe, substantially free from tungsten, comprising a unit dosage of a liquid composition comprising: (a) 12 mg of compound III-1; (b) 0.24 mg edetate calcium disodium; and (c) 0.18 mg glycine hydrochloride, wherein said prefilled syringe comprises compound II-1 in an amount of less than about 25, about 100, about 125, about 150, about 185, about 187, or about 190 ppm and/or where the amount of compound II-1 and compound IV-1 is present in amount of less than about 25, about 100, about 125, about 150, about 185, about 187, or about 190 ppm in total;
(ii) administering the unit dosage to a subject via subcutaneous injection.

In certain embodiments, a subject weighs between about 62 and about 114 kg. In some embodiments, the subject is suffering from opioid induced constipation, including but not limited to, for example, subjects who are terminally ill or suffer from chronic pain.

In other embodiments of the present invention, the compositions contain a compound of either of formula I or II, in an amount of at least about 97, 97.5, 98, 98.5, 99, 99.5, 99.8 weight percent where the percentages are based on the free base of said compound and on the total weight of the composition. In other embodiments, the composition containing a compound of either of formula I or II contains no more than about 2.0 area percent HPLC of total organic impurities and more preferably no more than about 1.5 area percent HPLC total organic impurities relative to the total area of the HPLC chromatogram.

In other embodiments of the present invention, a composition is provided comprising a compound of formula III, at least one compound of formula I or II, and at least one pharmaceutically acceptable carrier. In some embodiments, such compositions contain a compound of formula I or II in an amount of about 1 weight percent to about 99 weight percent, where the percentages are based on the free base of said compound and on the total weight of the composition. In other embodiments, the composition containing a compound of formula I or II contains no more than about 2.0 area percent HPLC of total organic impurities and more preferably no more than about 1.5 area percent HPLC total organic impurities relative to the total area of the HPLC chromatogram.

In certain embodiments, the present invention is directed to a composition, as described herein, comprising a prodrug of a compound of formula I. The term "prodrug," as used herein, means a compound that is convertible in vivo by metabolic means (e.g. by hydrolysis) to a compound of formula I. Various forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991), Bundgaard, et al., Journal of Drug Delivery Reviews, 8:1-38 (1992), Bundgaard, J. of Pharmaceutical Sciences, 77:285 et seq. (1988); and Higuchi and Stella (eds.) Prodrugs as Novel Drug Delivery Systems, American Chemical Society (1975), each of which is hereby incorporated by reference in its entirety.

Combination Products and Combined Administration

In certain embodiments, inventive compositions, and formulations thereof, may be administered alone to treat one or more disorders as described herein, or alternatively may be administered in combination with (whether simultaneously or sequentially) one or more other active agents useful to treat one or more disorders as described herein. Thus, an inventive composition, or formulation thereof, can be administered concurrently with, prior to, or subsequent to, one or more active agents.

In certain embodiments, inventive compositions include one or more other active agents in addition to a compound of formula I that is not a compound of formula I. In certain embodiments, the present invention provides a formulation that delivers a compound of formula I and at least one additional active agent.

In some embodiments, inventive formulations comprise both an opioid and a compound of formula I. Such combination products, containing both an opioid and a compound of formula I would allow simultaneous relief of pain and minimization of opioid-associated side effects (e.g., gastrointestinal effects (e.g., delayed gastric emptying, altered GI tract motility), etc.).

Opioids useful in treatment of analgesia are known in the art. For example, opioid compounds include, but are not limited to, alfentanil, anileridine, asimadoline, bremazocine, burprenorphine, butorphanol, codeine, dezocine, diacetylmorphine (heroin), dihydrocodeine, diphenoxylate, ethylmorphine, fedotozine, fentanyl, funaltrexamine, hydrocodone, hydromorphone, levallorphan, levomethadyl acetate, levorphanol, loperamide, meperidine (pethidine), methadone, morphine, morphine-6-glucoronide, nalbuphine, nalorphine, nicomorphine, opium, oxycodone, oxymorphone, papaveretum, pentazocine, propiram, propoxyphene, remifentanil, sufentanil, tilidine, trimebutine, and tramadol. In some embodiments the opioid is at least one opioid selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, nicomorphine, oxycodone, oxymorphone, papaveretum, pentazocine, propiram, propoxyphene, sufentanil and/or tramadol. In certain embodiments of the present invention, the opioid is selected from morphine, codeine, oxycodone, hydrocodone, dihydrocodeine, propoxyphene, fentanyl, tramadol, and mixtures thereof. In a particular embodiment, the opioid is loperamide. In other embodiments, the opioid is a mixed agonist such as butorphanol. In some embodiments, the subjects are administered more than one opioid, for example, morphine and heroin or methadone and heroin.

The amount of additional active agent(s) present in combination compositions of this invention will typically be no more than the amount that would normally be administered in a composition comprising that active agent as the only therapeutic agent. In certain embodiments of the present invention, the amount of additional active agent will range from about 50% to 100% of the amount normally present in a composition comprising that compound as the only therapeutic agent.

In certain embodiments, inventive formulations may also be used in conjunction with and/or in combination with conventional therapies for gastrointestinal dysfunction to aid in the amelioration of constipation and bowel dysfunction, For example, conventional therapies include, but may not be limited to functional stimulation of the intestinal tract, stool softening agents, laxatives (e.g., diphelymethane laxatives, cathartic laxatives, osmotic laxatives, saline laxatives, etc), bulk forming agents and laxatives, lubricants, intravenous hydration, and nasogastric decompression.

Uses and Kits of Inventive Formulations

As discussed above, the present invention provides compounds and compositions useful in antagonizing undesirable side effects of opioid analgesic therapy (e.g., gastrointestinal effects (e.g., delayed gastric emptying, altered GI tract motility), etc.). Furthermore, a provided compound or composition may be used as to treat subjects having disease states that are ameliorated by binding μ opioid receptors, or in any treatment wherein temporary suppression of the μ opioid receptor system is desired (e.g., ileus, etc.). In certain embodiments of the present invention, methods of use of formulations are in human subjects.

Accordingly, administration of provided compound or composition may be advantageous for treatment, prevention, amelioration, delay or reduction of side effects of opioid use, such as, for example, gastrointestinal dysfunction (e.g., inhibition of intestinal motility, constipation, GI sphincter constriction, nausea, emesis (vomiting), biliary spasm, opioid bowel dysfunction, colic, dysphoria, pruritus, urinary retention, depression of respiration, papillary constriction, cardiovascular effects, chest wall rigidity and cough suppression, depression of stress response, and immune suppression associated with use of narcotic analgesia, etc, or combinations thereof. Use of a provided compound or composition may thus be beneficial from a quality of life standpoint for subjects receiving opioids, as well as to reduce complications arising from chronic constipation, such as hemorrhoids, appetite suppression, mucosal breakdown, sepsis, colon cancer risk, and myocardial infarction.

In some embodiments, a provided compound or composition is useful for administration to a subject receiving acute opioid administration. In some embodiments, a provided compound or composition is useful for administration to subjects suffering from post-operative gastrointestinal dysfunction.

In other embodiments, a provided compound or composition is also useful for administration to subjects receiving chronic opioid administration (e.g., terminally ill patients receiving opioid therapy such as an AIDS patient, a cancer patient, a cardiovascular patient; subjects receiving chronic opioid therapy for pain management; subjects receiving opioid therapy for maintenance of opioid withdrawal). In some embodiments, the subject is a subject using opioid for chronic pain management. In some embodiments, the subject is a terminally ill patient. In other embodiments the subject is a person receiving opioid withdrawal maintenance therapy.

Alternative or additional uses for a provided compound or composition may be to treat, reduce, inhibit, or prevent effects of opioid use including, e.g., aberrant migration or proliferation of endothelial cells (e.g., vascular endothelial cells), increased angiogenesis, and increase in lethal factor production from opportunistic infectious agents (e.g., *Pseudomonas aeruginosa*). Additional advantageous uses of a provided compound or composition include treatment of opioid-induced immune suppression, inhibition of angiogenesis, inhibition of vascular proliferation, treatment of pain, treatment of inflammatory conditions such as inflammatory bowel syndrome, treatment of infectious diseases and diseases of the musculokeletal system such as osteoporosis, arthritis, osteitis, periostitis, myopathies, and treatment of autoimmune diseases.

In certain embodiments, a provided compound or composition may be used in methods for preventing, inhibiting, reducing, delaying, diminishing or treating gastrointestinal dysfunction, including, but not limited to, irritable bowel syndrome, opioid-induced bowel dysfunction, colitis, postoperative or postpartum ileus, nausea and/or vomiting, decreased gastric motility and emptying, inhibition of the stomach, and small and/or large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, abdominal or epigastric pain and discomfort, constipation, idiopathic constipation, post-operative gastrointestinal dysfunction following abdominal surgery (e.g., colectomy (e.g., right hemicolectomy, left hemicolectomy, transverse hemicolectomy, colectomy takedown, low anterior resection)), and delayed absorption of orally administered medications or nutritive substances.

Provided forms of a provided compound or composition are also useful in treatment of conditions including cancers involving angiogenesis, immune suppression, sickle cell anemia, vascular wounds, and retinopathy, treatment of inflammation associated disorders (e.g., irritable bowel syndrome), immune suppression, chronic inflammation.

In still further embodiments, veterinary applications (e.g., treatment of domestic animals, e.g. horse, dogs, cats, etc.) of use of a provided compound or composition are provided. Thus, use of provided formulations in veterinary applications analogous to those discussed above for human subjects is contemplated. For example, inhibition of equine gastrointestinal motility, such as colic and constipation, may be fatal to a horse. Resulting pain suffered by the horse with colic can result in a death-inducing shock, while a long-term case of constipation may also cause a horse's death. Treatment of equines with peripheral opioid receptor antagonists has been described, e.g., in U.S. Patent Publication No. 20050124657 published Jan. 20, 2005.

It will also be appreciated that a provided compound or composition can be employed in combination therapies, that is, a provided compound or composition can be administered concurrently with, prior to, or subsequent to, one or more other desired therapeutics or medical procedures. Particular combination therapies (therapeutics or procedures) to employ in a combination regimen will take into account compatibility of the desired therapeutics and/or procedures and the desired therapeutic effect to be achieved. It will also be appreciated that therapies employed may achieve a desired effect for the same disorder (for example, a formulation may be administered concurrently with another compound used to treat the same disorder), or they may achieve different effects (e.g., control of any adverse effects). As used herein, additional therapeutic compounds which are normally administered to treat or prevent a particular disease, or condition, are known as "appropriate for the disease, or condition, being treated".

In other embodiments, a provided compound or composition and unit dose forms are useful in preparation of medicaments, including, but not limited to medicaments useful in the treatment of side effects of opioid use (e.g., gastrointestinal side effects (e.g., inhibition of intestinal motility, GI sphincter constriction, constipation) nausea, emesis, vomiting, dysphoria, pruritus, etc.) or a combination thereof. Compounds of the present invention, and pharmaceutically acceptable compositions and formulations thereof, are useful for preparations of medicaments, useful in treatment of patients receiving acute opioid therapy (e.g., patients suffering from post-operative gastrointestinal dysfunction receiving acute opioid administration) or subjects using opioids chronically (e.g., terminally ill patients receiving opioid therapy such as an AIDS patient, a cancer patient, a cardiovascular patient; subjects receiving chronic opioid therapy for pain management; or subjects receiving opioid therapy for maintenance of opioid withdrawal). Still further, preparation of medicaments useful in the treatment of pain, treatment of inflammatory conditions such as inflammatory bowel syndrome, treatment of infectious diseases, treatment of diseases of the musculokeletal system such as osteoporosis, arthritis, osteitis, periostitis, myopathies, treatment of autoimmune diseases and immune suppression, therapy of post-operative gastrointestinal dysfunction following abdominal surgery (e.g., colectomy (e.g., right hemicolectomy, left hemicolectomy, transverse hemicolectomy, colectomy takedown, low anterior resection), idiopathic constipation, and ileus (e.g., post-operative ileus, post-partum ileus), and treatment of disorders such as cancers involving angiogenesiss, chronic inflammation and/or chronic pain, sickle cell anemia, vascular wounds, and retinopathy.

Still further encompassed by the invention are pharmaceutical packs and/or kits comprising a provided compound or composition and a container (e.g., a foil or plastic package, or other suitable container). Optionally instructions for use are additionally provided in such kits.

As described herein, the present invention provides methods for determining the purity of a sample of (R)—N-methylnaltrexone bromide. In certain embodiments, such methods can utilize reference standards. The term "reference standard" as used herein refers to "highly characterized specimens of drug substances, excipients, impurities, degradation products, dietary supplements, compendial reagents and performance calibrators. They are required for use in conducting official USP-NF tests and assays." as defined by the United States Pharmaceopeia. As would be appreciated by one of ordinary skill in the art, USP Reference Standards are also used as calibrators (e.g., particle count, melting point, and standardization of titrants and as blanks and controls). Reference Standards are used mainly in chromatographic and spectrophotometric procedures. In certain embodiments, the present invention provides compound II-1 as a reference standard. In some embodiments, the present invention provides a kit comprising a compound II-1 reference standard and optionally one or more reference standards of (R)—N-methylnaltrexone bromide, Impurity B, Impurity C, Impurity D, Impurity E, Impurity F, Impurity G, Impurity H, and Impurity I, as described in detail in Example 1, below.

In order that the invention described herein may be more fully understood, the following examples are set forth. It should be understood that these examples are for illustrative purposes only and are not to be construed as limiting this invention in any manner.

All features of each of the aspects of the invention apply to all other aspects mutatis mutandis.

EXEMPLIFICATION

General Procedures

Compound III-1 can be prepared, for example, according to the methods described in detail in International Patent Application publication number WO2006/127899, the entirety of which is hereby incorporated herein by reference.

Mass Spectral Analysis was performed using an Agilent 1100 HPLC system coupled with Applied Biosystems-PE SCIEX QSTAR PULSAR i quadrupole time-of-flight tandem mass spectrometer equipped with an electrospray ionization ion source operated in the positive ionization mode. The HPLC eluent was split to allow a flow at approximately 50 μL/min into the ion source of the mass spectrometer.

NMR spectroscopic analysis of compound II-1 was performed in DMSO-$d_6$ and the spectra were acquired on a Bruker DRX-500 NMR spectrometer equipped with a triple resonance inverse detection (TXI) probe. TMS was used as an internal reference for the proton resonances ($\delta^1$H at 0.00) and the solvent, DMSO-$d_6$, used as an internal standard for the carbon resonances ($\delta^{13}$C at 39.5).

The following abbreviations are used herein and have the following meanings:

KEY TO ABBREVIATIONS

| Abbreviation | Full Description |
|---|---|
| δ = | Chemical Shift |
| 2D = | Two Dimensional |
| amu = | Atomic Mass Units |
| COSY = | Correlation Spectroscopy |
| DMSO-$d_6$ = | Dimethylsulfoxide-$d_6$ |
| Da = | Daltons |
| dd = | Doublet of doublets |
| ESI-MS = | Electrospray Ionization Mass Spectrometry |
| HMBC = | Heteronuclear Multiple Bond Correlation |
| HPLC = | High Performance Liquid Chromatography |
| HSQC = | Heteronuclear Single Quantum Coherence |
| M = | Mass |
| m/z = | mass to charge |
| mDa = | milliDaltons |
| min = | Minutes |
| MNTX = | Methylnaltrexone bromide |
| MS = | Mass Spectrometry |
| MS/MS = | Mass Spectrometry/Mass Spectrometry |
| MV = | Millivolts |
| nm = | Nanometers |
| NMR = | Nuclear Magnetic Resonance |
| ppm = | parts per million |
| ROESY = | Rotating Frame Overhauser Effect Spectroscopy |
| td = | Triplet of doublets |
| TFA = | Trifluoroacetic acid |
| TMS = | Tetramethylsilane |
| TRIS = | Trishydroxymethylaminomethane |
| UV = | Ultraviolet |
| UV-VIS = | Ultraviolet-Visible |

Example 1

Isolation and Characterization of RRT 0.60

Previously, at least three degradation products of methylnaltrexone (compound III-1) were identified from HPLC analysis in 20 mg/mL isotonic saline solution (identified as RRT peaks at about 0.72, 0.89, and 1.48 when products were analyzed by HPLC). See, e.g., U.S. Patent Application Publication No. 20040266806, published Dec. 30, 2004, and WO2008/019115, published Feb. 14, 2008. Recently, methylnaltrexone-containing pre-filled syringes were examined for production of degradants. A new degradation product was observed, having a RRT at about 0.60. FIG. 1 depicts the LC/MS result of a stability study of such a pre-filled syringe at 40° C. and 75% relative humidity after 6 months.

For HPLC analysis a Prodigy ODS-3 15 cm×2.0 mm, 3 μm particles (Phenomenex) HPLC column at a flow rate of 0.25 mL/min, using the following eluent:

Mobile Phase: Strength (Isocratic: 75:25 (v/v) 0.1% TFA in Water/Methanol Purity: (Gradient):
Mobile Phase A=95:5 (v/v) 0.1% TFA in Water/Methanol
Mobile Phase B=35:65 (v/v) 0.1% TFA in Water/Methanol Gradient Program:

| Time (Min) | % Mobile Phase A |
|---|---|
| 0 | 100 |
| 45 | 50 |
| 45.1 | 100 |
| 60 | 100 |

Column Temperature: 50° C.
Flow: 0.25 mL/minute
Detection: UV, 280 nm or 310 nm
Injection volume: 20 μL
Sample Solvent: 0.05M Dibasic Sodium Phosphate pH 6.8

The following standards of compounds and known impurities were identified with associated calculated relative retention times ("RRT") and relative response factors ("RRF"):

| Compound | RRT | RRF |
|---|---|---|
| Impurity A: Diol degradant (II-1) | 0.60 | 0.0068 |
| Impurity B: Ring contracted | 0.79 | 1.00 |
| Impurity C: Quinone degradant | 0.89 | 0.0126 |
| Impurity D: S-Methylnaltrexone bromide | 0.91 | 1.09 |
| Methylnaltrexone bromide | 1.00 | 1.00 |
| Impurity E: Naltrexone base | 1.16 | 0.79 |
| Impurity F: 2,2,bis-methylnaltrexone bromide | 1.45 | 0.54 |
| Impurity G: O-Methylnaltrexone methobromide | 1.55 | 1.08 |
| Impurity H: Aldol dimer | 1.64 | 0.86 |
| Impurity I: Hoffmann elimination | 2.26 | 0.16 |

Impurity B, the RRT 0.79 degradant referred to as "Ring contracted," was identified as a ring contracted form of (R)—N-methylnaltrexone bromide and has the following structure:

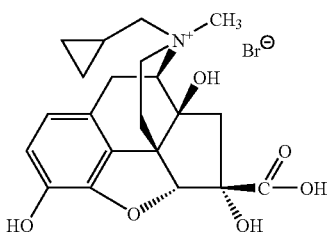

Impurity C, also referred to herein as compound IV-1, the RRT 0.89 degradant referred to as "Quinone degradant," was identified as a light degradation product of (R)—N-methylnaltrexone bromide, and has the following structure:

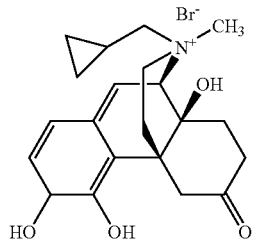

In certain embodiments, the present invention provides a composition comprising one or more of Impurity A, Impurity B, Impurity C, Impurity D, Impurity E, Impurity F, Impurity G, Impurity H, and Impurity I. In some embodiments, the present invention provides a kit comprising a vial comprising each of (R)—N-methylnaltrexone bromide, Impurity A, Impurity B, Impurity C, Impurity D, Impurity E, Impurity F, Impurity G, Impurity H, and Impurity I. In certain aspects, the present invention provides a kit comprising each of (R)—N-methylnaltrexone bromide, Impurity A, Impurity B, Impurity C, Impurity D, Impurity E, Impurity F, Impurity G, Impurity H, and Impurity I, wherein each impurity compound is contained within a separate vial.

Figure 2:
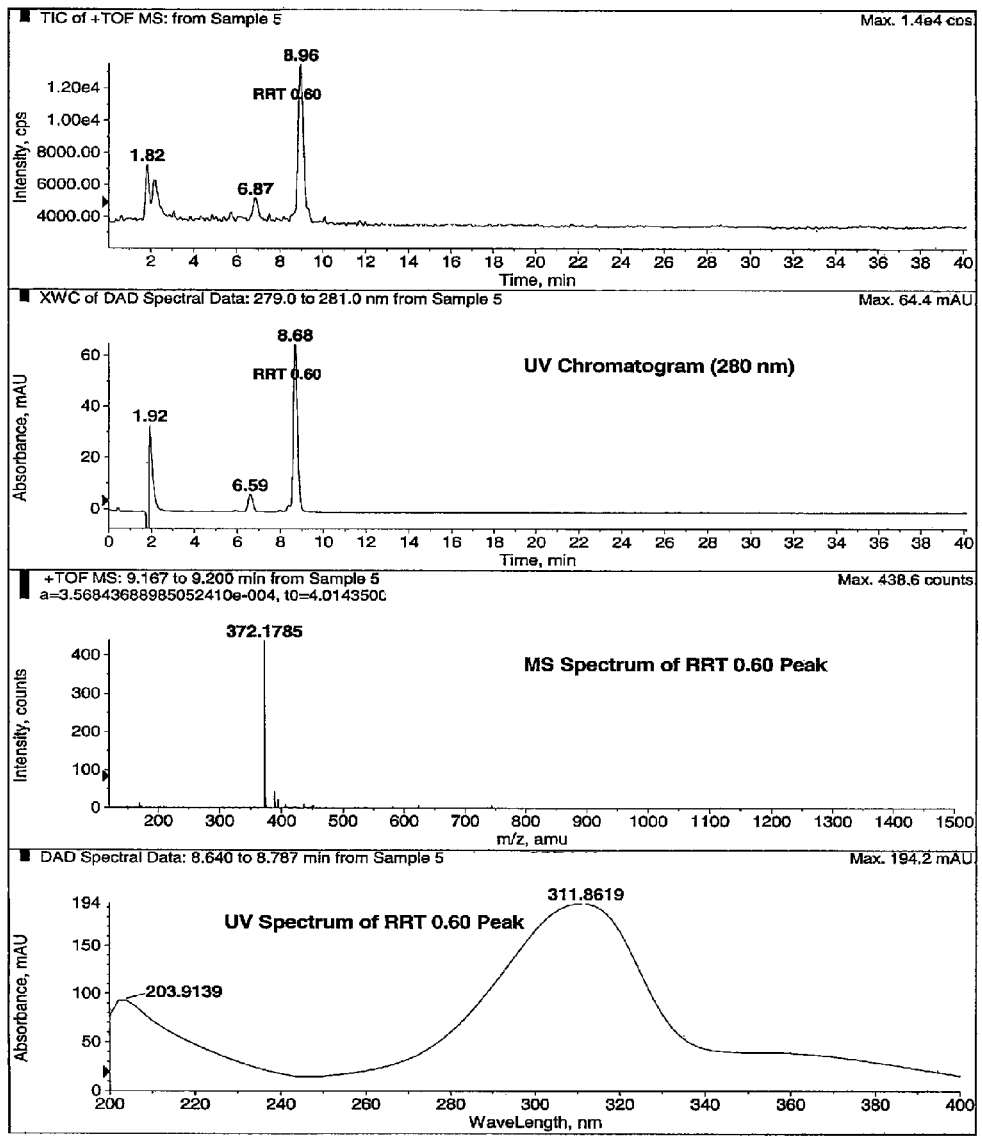
FIG. 2 depicts the total ion chromatogram (TIC), UV chromatogram (λ=280 nm), mass and UV spectra obtained for the RRT 0.60 peak.

Impurity A, the RRT 0.60 compound, referred to above as "Diol degradant," was isolated and characterized and corresponds to compound II-1. Specifically, LC/MS was conducted on the unknown peak eluting at RRT 0.60 in the (R)—N-methylnaltrexone pre-filled syringe stability sample. FIG. 2 depicts the total ion chromatogram (TIC), UV chromatogram (λ=280 nm), mass and UV spectra obtained for the RRT 0.60 peak. The UV spectrum has a unique absorption around 310 nm, which is similar to the previously identified quinone compound which as a RRT of about 0.89.

The measured accurate mass of 372.1809 amu corresponds to the elemental composition of C21H26NO5+ (error: 0.4 mDa). Its molecular formula indicates that the unknown peak contains one more oxygen atom than the above-depicted quinone compound.

Example 2

Synthetic Preparation of Compounds II-1 and II-3:

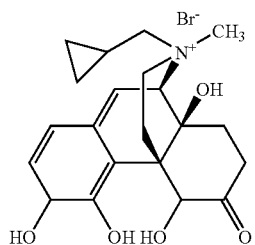

II-1

Method A

A solution of compound III-1 was dissolved in 1M TRIS pH 8 buffer and $H_2O_2$ (30%) was added in a 1:1.2 molar ratio. Before HPLC injection, the reaction was stopped by addition of TFA and the solution changed from brown/red to yellow. The solution was injected into a preparative HPLC with a Sunfire column (50×250 mm, C18, 5 μm), flow rate of 100 mL/min, and a mobile phase that started at 6% MeOH/0.25% TFA for 1 min and then was changed to a gradient of 12% MeOH/0.25% TFA in 30 min. The collected fraction was diluted with two parts of water and the compound was adsorbed onto a reverse phase polymeric sorbent (Strata-X from Phenomenex). The column was placed under vacuum to remove all remaining liquid and acetonitrile was used to elute the compound.

Figure 12:
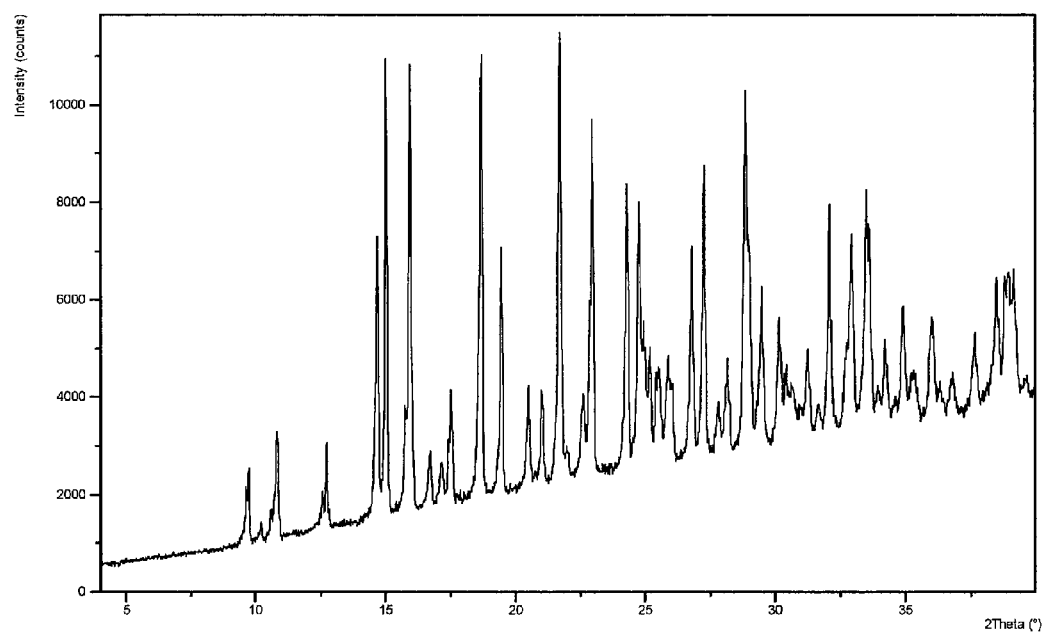
FIG. 12 depicts the X-ray diffraction pattern of crystalline compound II-1.
Figure 13:
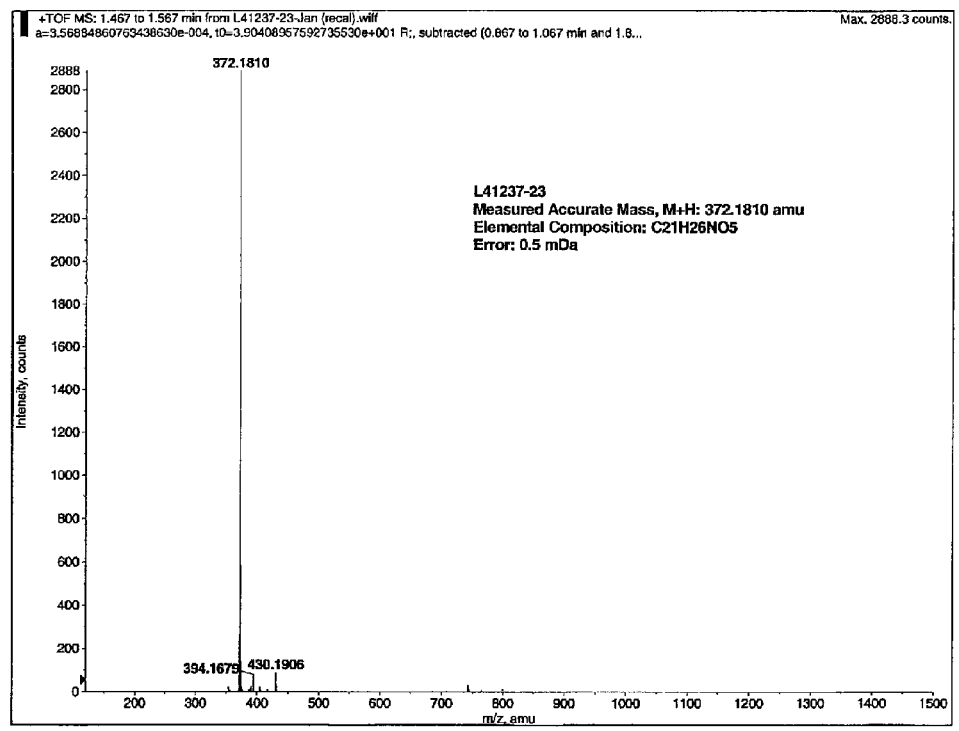
FIG. 13 depicts the mass spectrogram and mass measurement of the M+H ion of compound II-1 crystals.
Figure 14:
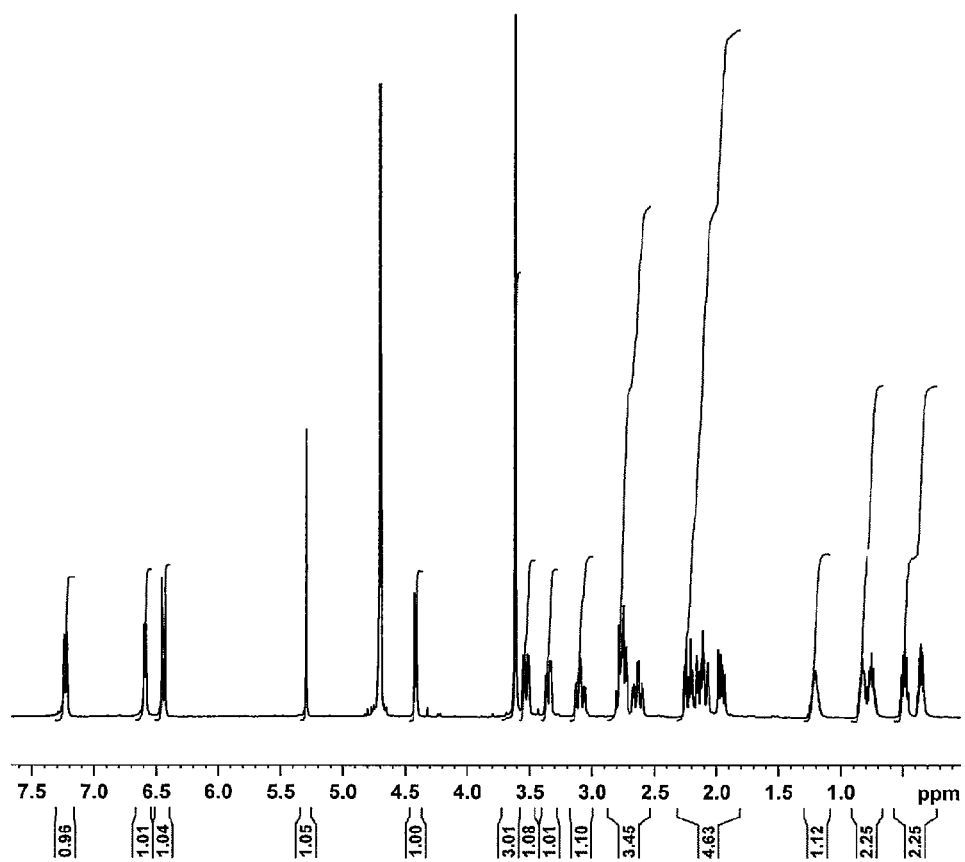
FIG. 14 depicts the $^1$H NMR spectrum of compound II-1.

About 20% water was added to the eluent which was then passed through a strong anion exchange column charged with bromide (Strata-SAX from Phenomenex). Acetonitrile was removed from the eluent by extraction with dichloromethane. The pH of the aqueous layer was adjusted to 4.2 (the optimum acidity to avoid hydrolysis), and then lyophilized to get a red powder. The compound was crystallized by dissolving the red powder in water and putting the solution in a water bath at 70° C., which caused crystals to form immediately. The crystals were filtered and dried under vacuum to provide compound II-1 as red crystals. The X-ray diffraction pattern for the resulting crystalline compound II-1 is depicted in FIG. 12. The mass spectrogram of the resulting crystalline compound II-1 is depicted in FIG. 13. The $^1$H NMR of the resulting crystalline compound II-1 is depicted in FIG. 14.

Method B

A solution of compound III-1 was dissolved in 1M TRIS pH 8 buffer and $H_2O_2$ (30%) was added in a 1:2 molar ratio. After about 30 minutes at room temperature, the reaction was stopped by addition of TFA and the solution changed from brown/red to yellow. The solution was injected into a preparative HPLC with a Sunfire column (50×250 mm, C18, 5 μm), flow rate of 100 mL/min, and a mobile phase that started at 6% MeOH/0.25% TFA for 1 min and then was changed to a gradient of 12% MeOH/0.25% TFA in 30 min. The collected fraction was immediately frozen and lyophilized to afford compound II-3 as a yellow solid.

Figure 3:
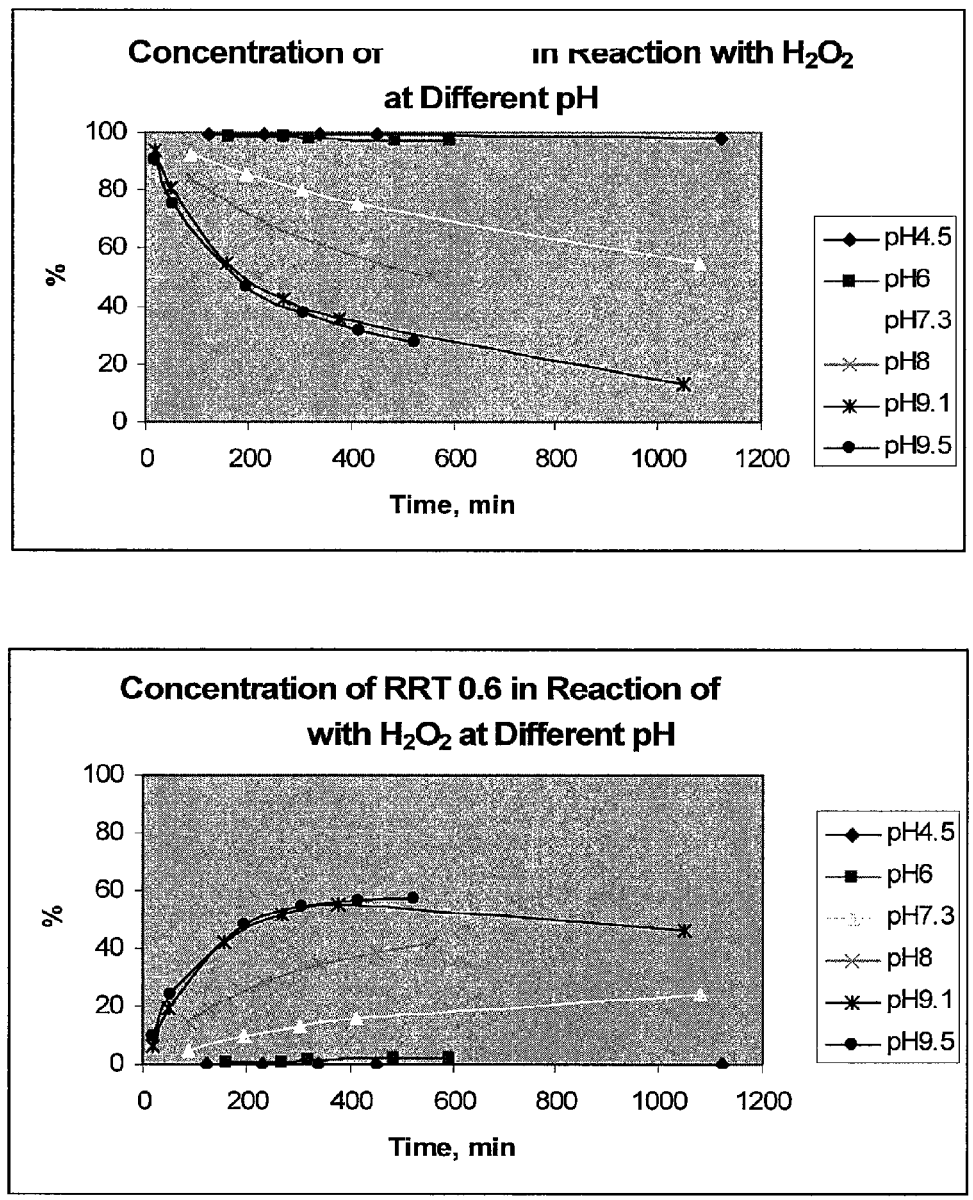
FIG. 3 depicts the effect of pH on reaction of compound III-1 with $H_2O_2$ to form compound II-1.

The reaction of compound III-1 with $H_2O_2$ to form compound II-3 was performed under different pH conditions to determine the effect of pH upon the reaction. It was found that at acidic pH the reaction of compound III-1 with $H_2O_2$ is very slow, whereas at basic pH the reaction is faster, following increase of pH (see FIG. 3).

Structural elucidation of compound II-3 was determined using: UV spectroscopy; ESI-MS; MS/MS; $^1$H NMR, $^{13}$C NMR, and 2 dimensional NMR techniques, as described in detail below. Positional numbering is as depicted below.

NMR Results

The $^1$H and $^{13}$C NMR resonances were assigned using COSY, HSQC, HMBC and ROESY spectra. The assignments are set forth in Table 1, below.

TABLE 1

$^1$H and $^{13}$C Resonance Assignments for Compound II-1 in DMSO-$d_6$

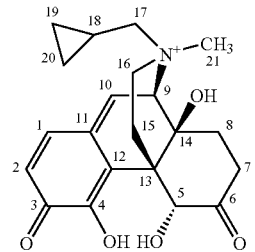

| Position | Group | Carbon shift[a] | Proton shift[b] |
|---|---|---|---|
| 1 | CH | 141.0 | 7.33 (doublet, J = 9.6 Hz) |
| 2 | CH | 127.1 | 6.38 (doublet, J = 9.6 Hz) |
| 3 | C | 182.2 | — |
| 4 | C | 151.1 | — |
| 4-OH | OH | — | 12.21 |
| 5 | CH | 74.8 | 5.08 |
| 6 | C | 205.7 | — |
| 7 | CH$_2$ | 35.1 | 2.70, 2.16 |
| 8 | CH$_2$ | 34.2 | 1.93 |
| 9 | CH | 66.7 | 4.44 (doublet, J = 7.0 Hz) |
| 10 | CH | 129.1 | 6.59 (doublet, J = 7.0 Hz) |
| 11 | C | 139.3 | — |
| 12 | C | 113.5 | — |
| 13 | C | 48.5 | — |
| 14 | C | 72.4 | — |
| 14-OH | OH | — | 6.82 |
| 15 | CH$_2$ | 24.8 | 2.50, 1.95 |

TABLE 1-continued

¹H and ¹³C Resonance Assignments for Compound II-1 in DMSO-d₆

| Position | Group | Carbon shift[a] | Proton shift[b] |
|---|---|---|---|
| 16 | CH₂ | 53.8 | 3.35 (dd, J = 13.8, 3.3 Hz), 3.01 (td, J = 13.8, 3.1 Hz) |
| 17 | CH₂ | 70.7 | 3.51 (dd, J = 13.4, 5.0 Hz), 2.87 (dd, J = 13.4, 9.2 Hz) |
| 18 | CH | 4.0 | 1.34 |
| 19 | CH₂ | 5.4 | 0.77, 0.57 |
| 20 | CH₂ | 3.2 | 0.72, 0.40 |
| 21 | CH₃ | 49.7 | 3.59 |

[a]Shifts relative to DMSO-d6 (δ¹³C = 39.5).
[b]Shifts relative to TMS (δ¹H = 0.0).

Figure 6:
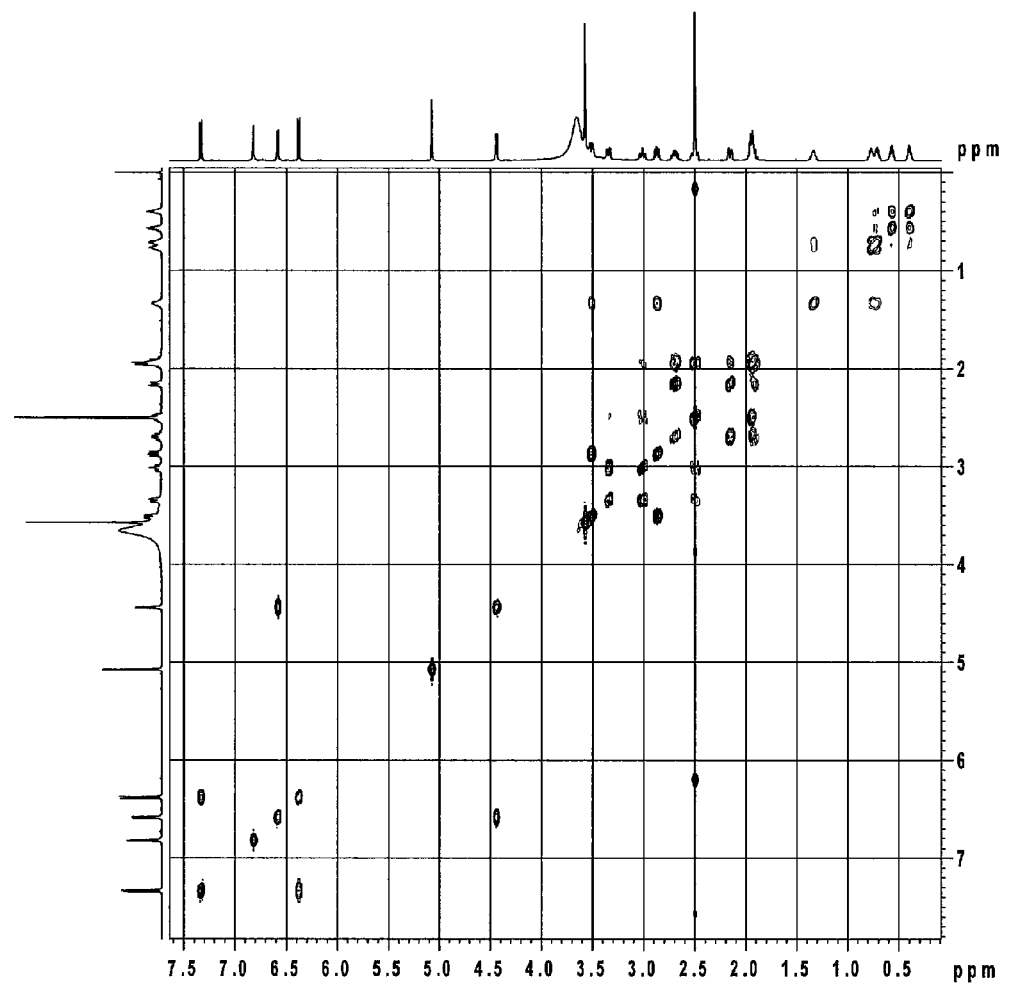
FIG. 6 depicts the COSY spectrum of compound II-1.
Figure 7:
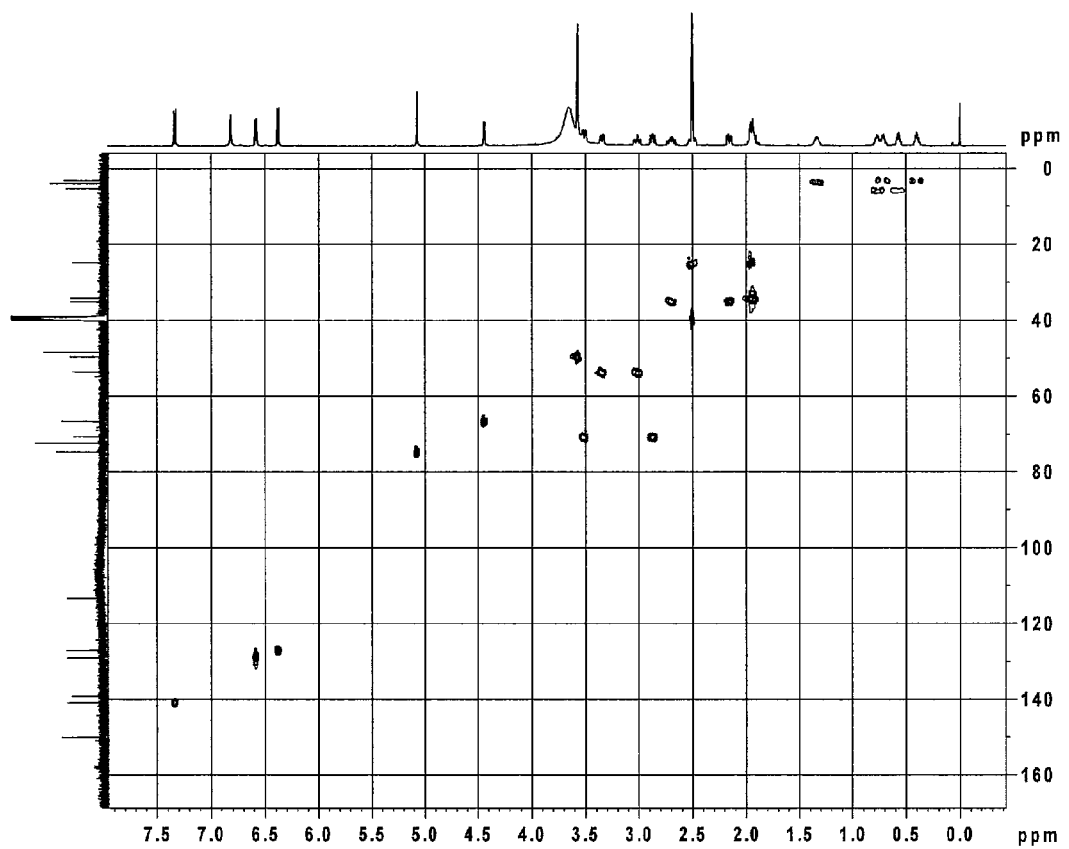
FIG. 7 depicts the HSQC spectrum of compound II-1.

The COSY spectrum (FIG. 6) shows that all the ¹H-¹H spin systems are the same as those observed for the quinone compound, Impurity D, except for H-5. In the quinone compound, Impurity D, C-5 is a methylene carbon with two well resolved diastereotopic protons and in compound II-1, H-5 is a methine proton at δ 5.08. The presence of the C-5 methine was confirmed by the HSQC spectrum (FIG. 7) which shows that H-5 is attached to a carbon at δ 74.8, a typical chemical shift for a carbon attached to oxygen.

Figure 8:
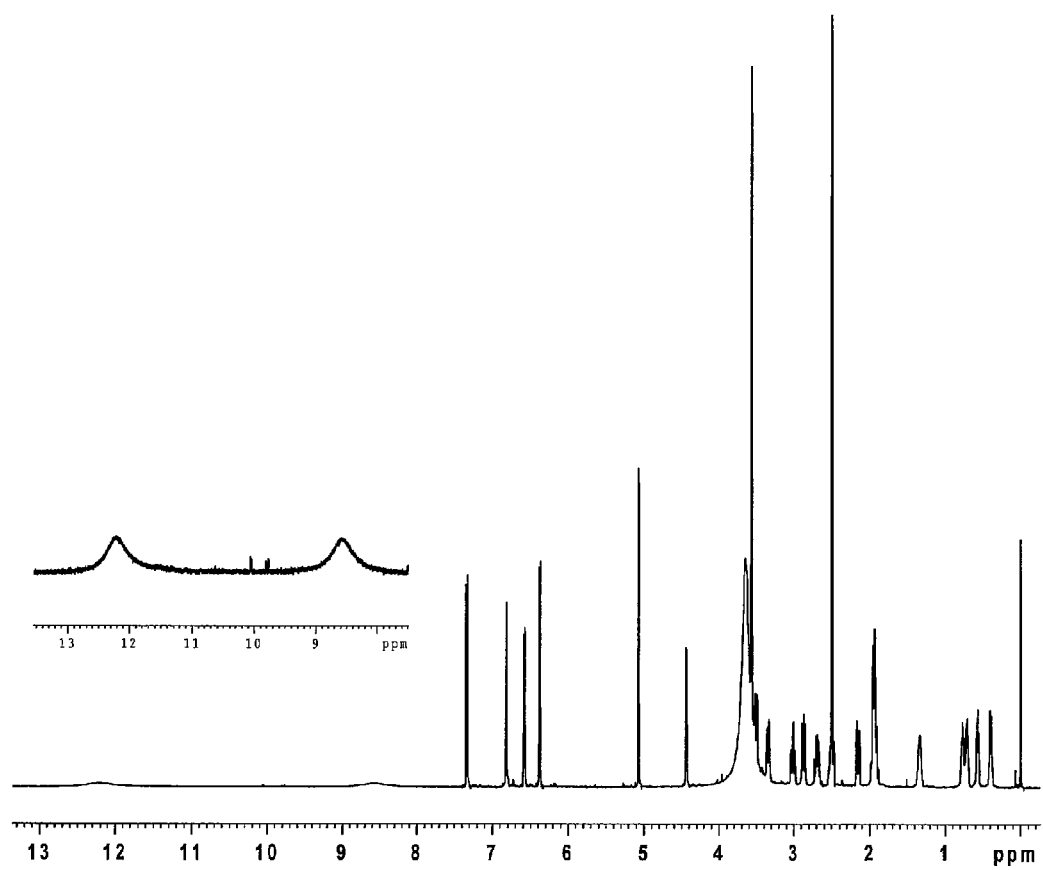
FIG. 8 depicts the $^1$H NMR spectrum of compound II-1.

In the ¹H NMR spectrum (FIG. 8) there are two hydroxyl protons observed at δ 12.21 and 8.58, assigned to the C-4 and C-5 OH groups, respectively. Their downfield chemical shifts and broad peak shape imply that they are very close each other, indicating that the C-5 hydroxyl is in the a orientation as depicted below.

Figure 9:
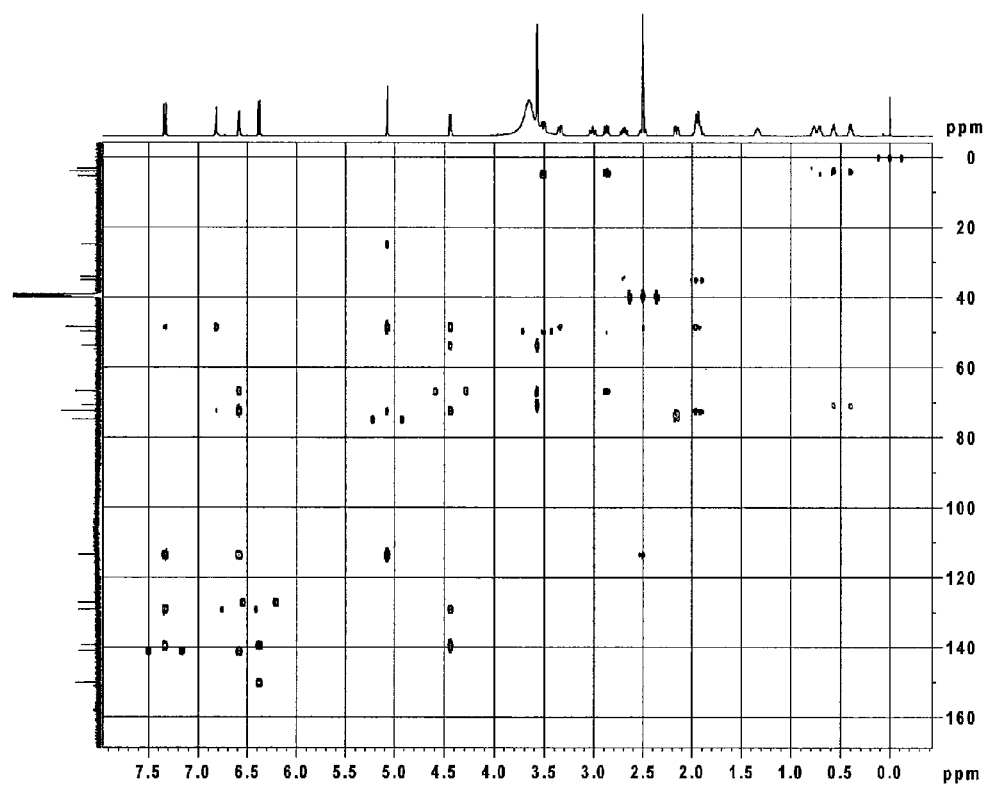
FIG. 9 depicts the HMBC spectrum of compound II-1.

The HMBC spectrum (FIG. 9) provides additional evidence that the hydroxyl group at C-5 is facing down. H-5 shows a strong three bond correlation to C-12, requiring their anti-coplanar relationship as depicted below:

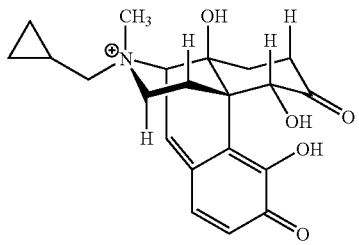

Figure 10:
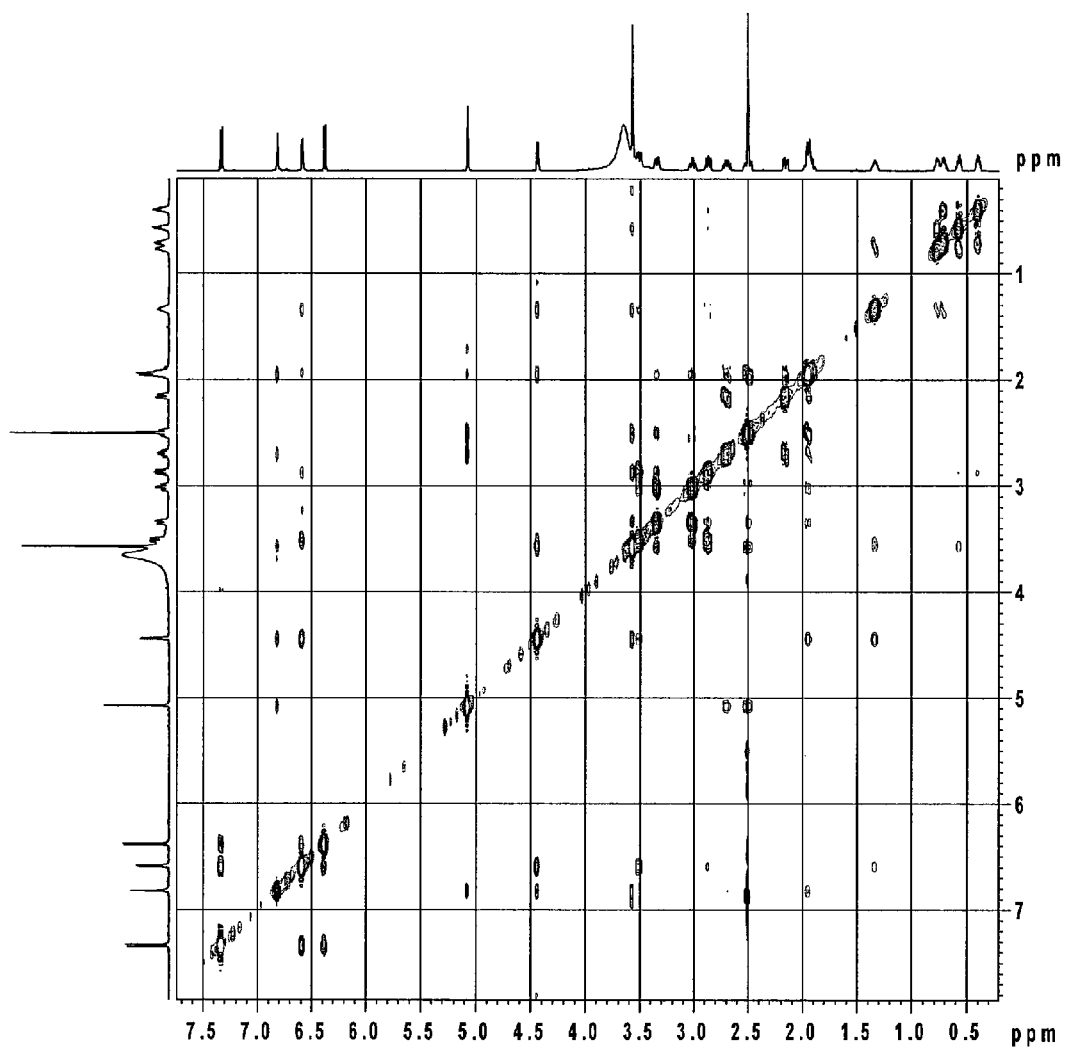
FIG. 10 depicts the ROESY spectrum of compound II-1.
Figure 11:
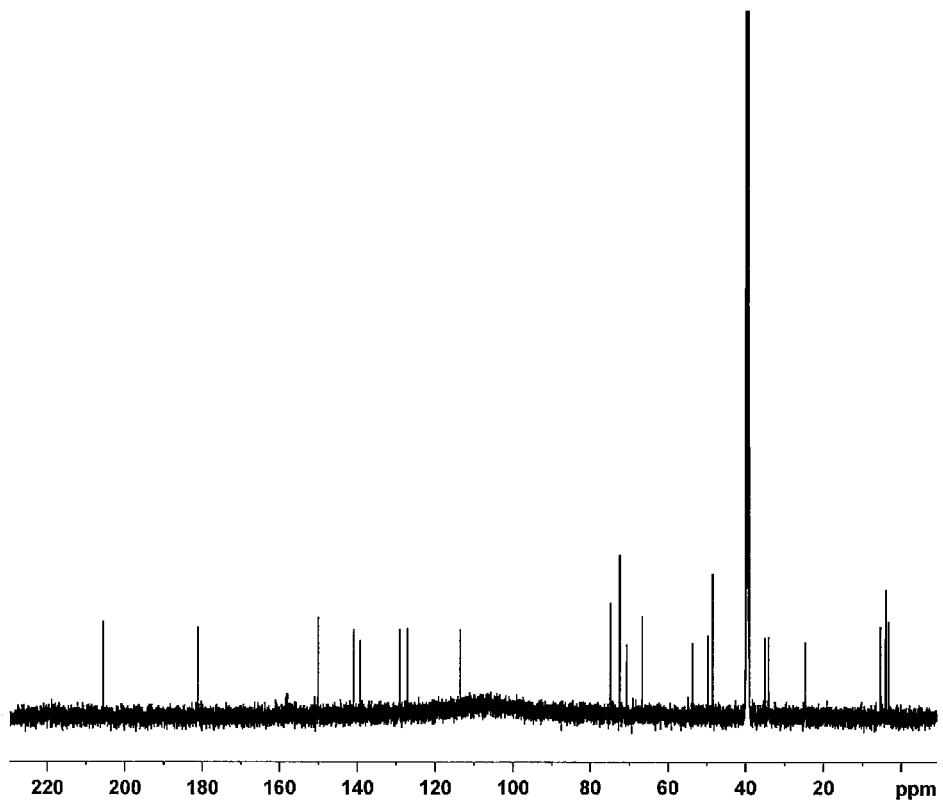
FIG. 11 depicts the $^{13}$C NMR spectrum of compound II-1.

The axial orientation of H-5 is confirmed by the ROESY spectrum (FIG. 10). H-5 shows 1,3-diaxal type of NOEs to C-14-OH at δ 6.82, H-8 at δ 2.70, and H-14 at δ 2.50. The ¹³C NMR spectrum of compound II-3 is shown in FIG. 11.

Example 3

Comparison of Synthetic Compound II-3 and Isolated RRT 0.60

Figure 4:
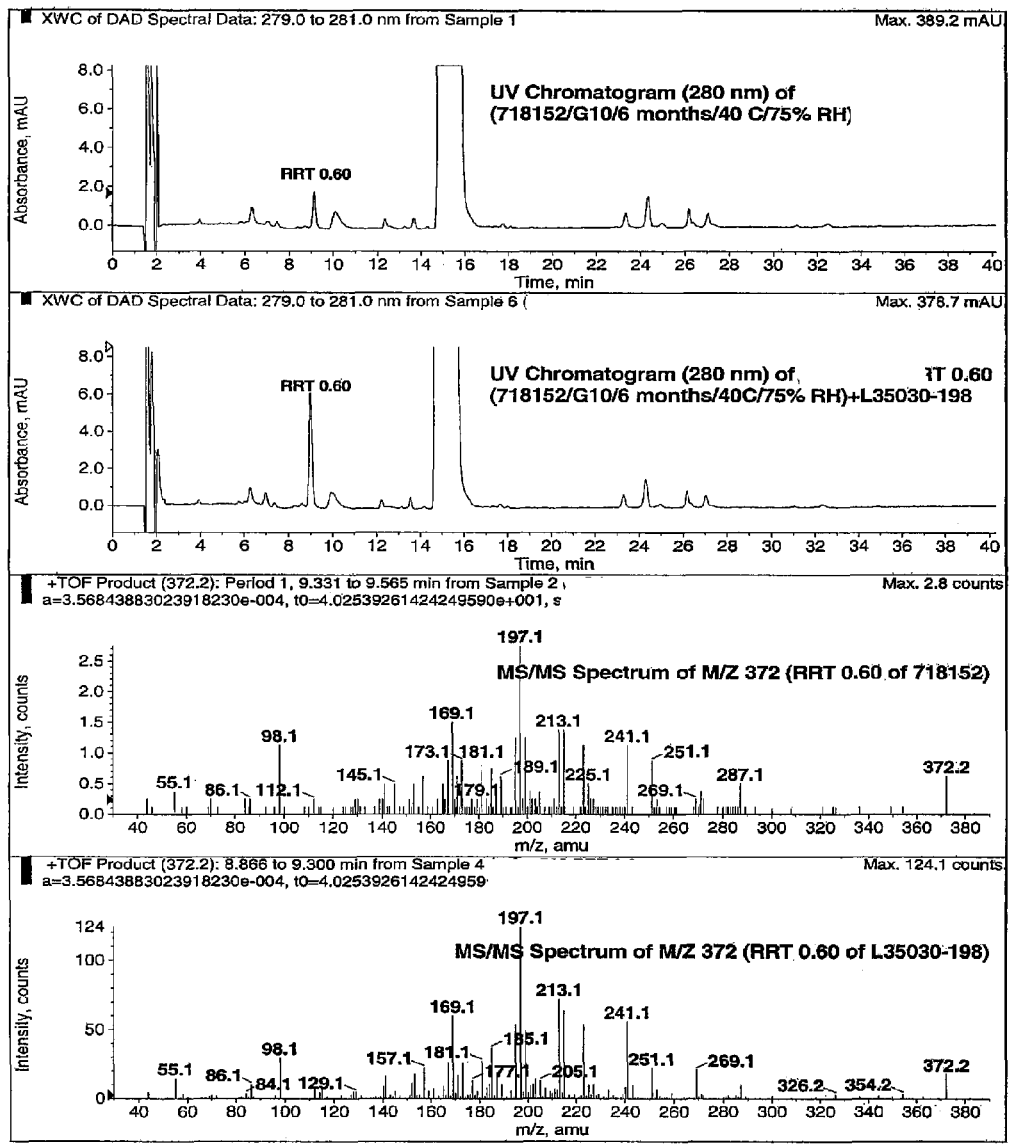
FIG. 4 shows the UV chromatogram of a stability sample and the chromatogram of a stability sample spiked with compound II-1 prepared according to Example 2.
Figure 5:
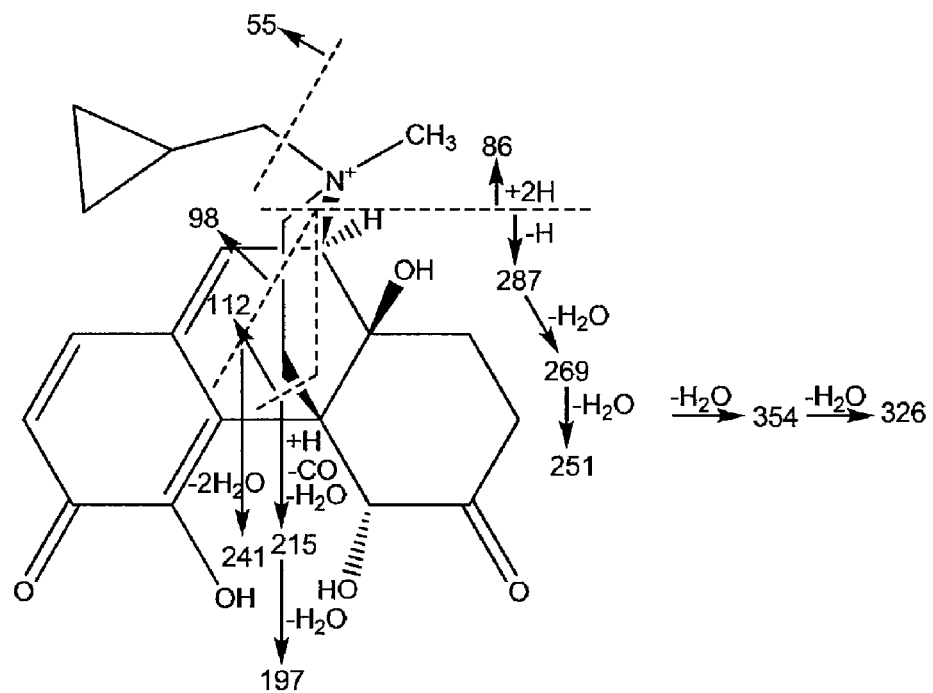
FIG. 5 depicts the fragmentation assignments of compound II-1 with the chemical structure based on NMR data.

Compound II-3, prepared according to Example 2, Method B, was analyzed by LC-MS. As depicted in FIG. 2, the major peak eluting around 9 minutes has the same mass and UV spectra as the RRT 0.60 peak. Also, the measured accurate mass of 372.1785 amu provides the same ionic formula (error: −2.0 mDa). In addition, compound II-3, prepared according to Example 2, Method B, was spiked into the sample obtained from the stability study described at Example 1. FIG. 4 shows the UV chromatograms of both the non-spiked and spiked samples. The peak at RRT 0.60 clearly indicates that the synthetic compound II-3 is the same compound. LC-MS/MS was conducted on the ion of m/z 372 to get structural information. MS/MS data for the RRT 0.60 peak and the synthetic sample are shown in the bottom two boxes in FIG. 4. Both spectra are quite similar although the synthetic compound provides much better fragment ion intensities. Fragmentation assignments with the chemical structure based on NMR data are shown in FIG. 5. The LC/MS data are consistent with the structure as determined by NMR experiments.

Example 4

Evaluation of Oxidation Method:

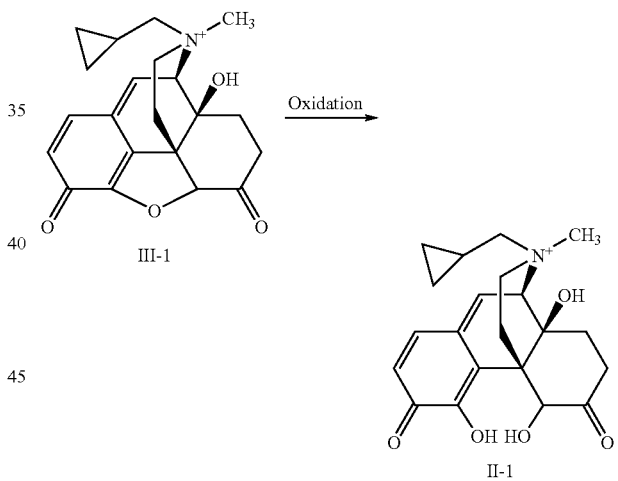

As described above in Example 2, compound II-1 was prepared by oxidation of compound III-1 with H₂O₂. A screen of additional oxidizing reagents was performed to optimize yield and purity of the oxidation reaction. A summary of the reactions performed is set forth in Tables A though E, below. As used herein, the term "SLI" refers to the single largest impurity.s As summarized in Table A, below, reactions were performed at room temperature using 1 equivalent of different oxidizing agents.

For each reaction, 0.5 g of III-1 was combined with 6 mL of TRIS.HCl (1M, pH 8.0) in water. Oxidizing reagent (1 equivalent) was added and the resulting mixture stirred at room temperature for the designated time. All reactions were monitored by HPLC at 280 nM. % values reported as is from the chromatogram

TABLE A

| | Oxidant/Rx Conditions | Time (h) | HPLC % | | | |
|---|---|---|---|---|---|---|
| | | | % II-1 | % III-1 | % SLI | % other imps |
| 1 | 30% $H_2O_2$ 0.13 mL | 2.5 | 28 | 64.5 | 3.0 | 4.5 |
| | | 4.5 | 32 | 60 | 4.0 | 4.0 |
| | | 20 | 43.6 | 34.2 | 8.0 | 14.2 |
| 2 | 70% tBuOOH 0.16 mL | 2.5 | 4.7 | 93 | 0.7 | 1.6 |
| | | 4.5 | 7.1 | 90 | 1.2 | 1.7 |
| | | 20 | 20 | 70.9 | 3.3 | 5.8 |
| 3 | Oxone + Acetone + $NaHCO_3$ 0.7 g Acetone 0.36 mL $NaHCO_3$ 0.33 g | 2.5 | 14 | 29 | 16.0 | 41.0 |
| | | 4.5 | 14 | 29 | 16.0 | 41.0 |
| | | 20 | 12.8 | 25 | 14.7 | 47.5 |
| 4 | DDQ 0.26 g | 2.5 | 0.3 | 11 | 28.0 | 61.7 |
| | | 4.5 | 0.3 | 11 | 25.0 | 63.7 |
| | | 20 | 0.3 | 10.9 | 21.8 | 67.0 |
| 5 | 32% Peracetic acid 0.24 mL | 2.5 | 8.8 | 47 | 10.0 | 34.2 |
| | | 4.5 | 8.8 | 47 | 10.0 | 34.2 |
| | | 20 | 8.4 | 45.6 | 10.8 | 35.2 |
| 6 | 77% mCPBA 0.256 g | 2.5 | 25.1 | 42.9 | 6.9 | 25.1 |
| | | 4.5 | 25 | 42 | 7.1 | 25.9 |
| | | 20 | 25 | 38.4 | 6.3 | 30.3 |

As summarized in Table B, below, oxidation reactions were performed with varying equivalents of oxidizing reagent (i.e., oxidant) and varying reaction times.

For each reaction, 0.5 g of III-1 was combined with 6 mL of TRIS.HCl (1M, pH 8.0) in water and cooled to ~10° C. Oxidizing reagent (in the specified amount) was added and the resulting mixture stirred at room temperature for the designated time.

TABLE B

| | Oxidant | Equivs. | Time (h) | HPLC % | | | |
|---|---|---|---|---|---|---|---|
| | | | | % II-1 | % III-1 | % SLI | % other imps |
| 1 | 30% $H_2O_2$ 0.26 mL | 2 | 2 | 2 | 91 | 2.5 | 4.5 |
| | | | 4 | 2.3 | 87 | 4.4 | 6.3 |
| | | | 20 | 3.4 | 84.6 | 4.9 | 7.1 |
| 2 | 30% $H_2O_2$ 0.65 mL | 5 | 2 | 0 | 93 | 2 | 5 |
| | | | 4 | 0 | 92 | 2.6 | 4.4 |
| 3 | 70% tBuOOH 0.32 mL | 2 | 2 | 7.2 | 90.1 | 1.4 | 1.3 |
| | | | 3 | 17.2 | 78 | 2.2 | 2.6 |
| | | | 20 | 40.5 | 46.5 | 4.3 | 8.7 |
| | | | 1 h at 50 C. | 39.6 | 35.6 | 5.9 | 18.9 |
| | | | 44 | 43.1 | 29.1 | 5.3 | 22.5 |
| | | | 72 | 43 | 22 | 8.3 | 26.7 |
| | | | 90 | 44.3 | 19 | 10.3 | 26.4 |
| 4 | 70% tBuOOH 0.8 mL | 5 | 2 | 13.3 | 82 | 2.1 | 2.6 |
| | | | 4 | 28 | 66 | 2.3 | 3.7 |
| | | | 20 | 53.7 | 33.1 | 3.2 | 10 |
| | | | 1 h at 50 C. | 49.6 | 25.4 | 9.4 | 15.6 |
| | | | 44 | 54 | 19.3 | 9.7 | 17 |
| | | | 72 | 55.1 | 12.3 | 6.8 | 25.8 |
| | | | 90 | 53.4 | 10.7 | 6.9 | 29 |
| 5 | 77% mCPBA 0.512 g | 2 | 2 | 24.5 | 38.5 | 9.9 | 27.1 |
| | | | 20 | 20.2 | 30.4 | 12.7 | 36.7 |
| 6 | 77% mCPBA 1.28 g | 5 | 2 | 18.6 | 31.6 | 15.3 | 34.5 |
| | | | 20 | 13.8 | 25.7 | 11 | 49.5 |

As summarized in Table C, below, oxidation reactions were performed with $H_2O_2$ and tBHP in varying equivalents and prolonged stirring at room temperature.

For each reaction, 0.5 g of III-1 was combined with 6 mL of TRIS.HCl (1M, pH 8.0) in water. The oxidant was added and the resulting mixture stirred for the designated time.

TABLE C

| | Oxidant | Equivs. | Time (h) | HPLC % | | | |
|---|---|---|---|---|---|---|---|
| | | | | % II-1 | % III-1 | % SLI | % Other imps |
| 1 | 30% H$_2$O$_2$ (0.13 mL) | 1 | 2 | 22.3 | 72 | 2 | 3.7 |
| | | | 18 | 35.4 | 43.8 | 7.1 | 13.7 |
| | | | 28 | 40.4 | 32.8 | 8.2 | 17.6 |
| | | | 44 | 44.5 | 21.7 | 8.8 | 25 |
| 2 | 30% H$_2$O$_2$ | 2 (0.26 mL) | 20 | 5.9 | 89.1 | 1.1 | 3.9 |
| 3 | 30% H$_2$O$_2$ | 5 (0.65 mL) | 20 | 2.1 | 94.3 | 2 | 1.6 |
| 4 | 70% TBHP | 5 (0.8 mL) | 2 | 15 | 82.8 | 0.9 | 1.3 |
| | | | 18 | 54.2 | 37.2 | 2.3 | 6.3 |
| | | | 28 | 60 | 28.5 | 2.4 | 9.1 |
| | | | 44 | 63.2 | 20.2 | 3.2 | 13.4 |
| | | | 92 | 62 | 11.4 | 6.9 | 19.7 |
| 5 | 70% TBHP | 10 (1.6 mL) | 2 | 19.5 | 77.1 | 1.4 | 2 |
| | | | 18 | 60.4 | 30 | 2 | 7.6 |
| | | | 28 | 64.3 | 22.2 | 3.2 | 10.3 |
| | | | 44 | 65.4 | 15.6 | 6.6 | 12.4 |
| | | | 92 | 62 | 8.9 | 11.5 | 17.6 |

As summarized in Table D, below, oxidation reactions were performed with tBHP in varying equivalents and prolonged stirring at elevated temperature (35° C.).

For each reaction, 0.5 g of III-1 was combined with 6 mL of TRIS HCl (1M, pH 8.0) in water. Oxidant was added in the designated amount and the reaction stirred for the designated time at 35° C.

TABLE D

| | Oxidant | Equivs. | Time (h) | HPLC % | | | % other imps |
|---|---|---|---|---|---|---|---|
| | | | | % II-1 | % III-1 | % SLI | |
| 1 | 70% TBHP | 2 | 2 | 21.7 | 73.1 | 1.3 | 3.9 |
| | | | 18 | 45.3 | 34 | 3.7 | 17 |
| 2 | 70% TBHP | 5 | 2 | 33.8 | 61.6 | 1.5 | 3.1 |
| | | | 18 | 56 | 22.5 | 5.2 | 16.3 |
| 3 | 70% TBHP | 10 | 2 | 40 | 53 | 2.4 | 4.6 |
| | | | 18 | 54.1 | 17.5 | 14.3 | 14.1 |

As summarized in Table E, below, oxidation reactions were performed with tBHP in varying solvents.

For each reaction, 0.5 g of III-1 was combined with 3 mL of TRIS.HCl buffer (1M, pH 8.0) and designated solvent (3 mL). 70% TBHP (5 equivs) was added and the resulting mixture stirred at room temperature for 48 hours.

TABLE E

| | Oxidant | Solvent | HPLC % 280 nM | | | |
|---|---|---|---|---|---|---|
| | | | % II-1 | % III-1 | % SLI | % other imps |
| 1 | TBHP, 2eq. | None | 52 | 36 | 3.5 | 8.5 |
| 2 | TBHP | None | 63 | 22.6 | 3.3 | 11.1 |
| 3 | TBHP | EtOH | 26 | 61 | 6.6 | 6.4 |
| 4 | TBHP | NMP | 15 | 77 | 3.9 | 4.1 |
| 5 | TBHP | DME | 23 | 60 | 10 | 7 |
| 6 | TBHP | THF | 31 | 47 | 13 | 9 |

Example 5

Tungstate Stability Studies

A short-term evaluation was conducted to investigate the effect of tungstate on methylnaltrexone bromide for the formation of RRT 0.60 under the stressed conditions of high temperature and oxygen exposure. For the stressed sample, the formulation was spiked with 1 mM sodium tungstate and sparged with oxygen for one hour at room temperature. The solution was then autoclaved at 121° C. for one hour. Control samples were also prepared where each solution was prepared without exposure to tungstate, oxygen or heat.

After the stressed conditions discussed above, the sample exposed to tungsten, oxygen and heat produced 28 ppm of RRT 0.60 degradant. This degradant was observed at lower levels in the control samples. Based on this study, tungsten may aid in catalyzing the formation of the RRT 0.60 degradant. The levels of RRT 0.60 degradant observed in the control samples show that temperature and oxygen content are also contributing factors in this oxidative degradation reaction.

| Tungstate Evaluation - Short-term Stressed Study | | | |
|---|---|---|---|
| 1 mM Tungstate | Oxygen | Autoclave | RRT 0.60 (ppm) |
| Sample 1 | | | ≦7 ppm |
| Sample 2 | | X | ≦7 ppm |
| Sample 3 | | X | 9 |
| Sample 4 | X | X | ≦7 ppm |
| Sample 5 | X | | X | 17 |
| Sample 6 | X | X | X | 28 |

A long-term evaluation of 18 months was conducted to investigate the effect of tungstate on methylnaltrexone bromide for the formation of RRT 0.60 under standard conditions in standard Sterile, Clean, Ready to Fill (SCF™) syringes (1 mL Becton Dickinson (BD) Syringe, Type 1 borosilicate glass with stainless steel needle 27G×½ inch, BD Stopper 11510, West 4023/50 grey bromobutyl rubber. Coating: contact side with Daikyo Fluro Tec, remaining part with B2-40 coating, BD Rigid Needle Shield with FM27/0 rubber needle shield and polypropylene rigid shield cover). In this study, syringes containing either an 8 mg methylnaltrexone unit dosage (8 mg methylnaltrexone in 0.4 mL water with 2.6 mg sodium chloride, 0.16 mg edetate calcium disodium, and 0.12 mg glycine hydrochloride) or a 12 mg methylnaltrexone unit dosage (12 mg methylnaltrexone in 0.6 mL water 3.9 mg sodium chloride, 0.24 mg edetate calcium disodium, and 0.18 mg glycine hydrochloride) were stored under the following conditions: 25° C./60% RH, 30° C./75% RH, and 40° C./75% RH. The results of this study show that the RRT 0.60 compounds formed to a level of 40 ppm at 25° C. and 60% RH and up to 204 ppm at 30° C. and 75% RH. After 6 months at 40° C. and 75% RH, 145 ppm was observed. These results are shown in Table 2, below.

TABLE 2

Amount of RRT 0.60 (ppm) in Standard SCF Syringes*

| Batch# | Time Zero | 1 month | 3 months | 6 months | 9 months | 12 months | 18 months |
|---|---|---|---|---|---|---|---|
| Condition: 25° C./60% RH | | | | | | | |
| G16 8 mg | <7 | 8 | 13 | 13 | 17 | 18 | 26 |
| G17 8 mg | <7 | <7 | 16 | 13 | 18 | 19 | 27 |
| G18 8 mg | <7 | <7 | 10 | 12 | 15 | 18 | 40 |
| G19 12 mg | <7 | <7 | 15 | 14 | 18 | 14 | 36 |
| G20 12 mg | <7 | <7 | 14 | 8 | 18 | 19 | 24 |
| G21 12 mg | <7 | <7 | 11 | 16 | 16 | 14 | 31 |
| Condition: 30° C./75% RH | | | | | | | |
| G16 8 mg | NA | 8 | 15 | 16 | 28 | 26 | 101 |
| G17 8 mg | NA | 9 | 12 | 20 | 23 | 22 | 70 |
| G18 8 mg | NA | <7 | 12 | 11 | 28 | 34 | 90 |
| G19 12 mg | NA | 10 | 14 | 12 | 21 | 23 | 55 |
| G20 12 mg | NA | <7 | 18 | 30 | 22 | 29 | 86 |
| G21 12 mg | NA | <7 | 16 | 21 | 28 | 90 | 204 |
| Condition: 40° C./75% RH | | | | | | | |
| G16 8 mg | NA | 10 | 33 | 100 | NA | NA | NA |
| G17 8 mg | NA | 21 | 57 | 47 | NA | NA | NA |
| G18 8 mg | NA | 14 | 22 | 145 | NA | NA | NA |
| G19 12 mg | NA | 20 | 50 | 121 | NA | NA | NA |
| G20 12 mg | NA | 18 | 47 | 116 | NA | NA | NA |
| G21 12 mg | NA | 11 | 69 | 102 | NA | NA | NA |

Note:
All values reported in ppm, acquired by the 310 nm HPLC method.
LOQ = 7 ppm
NA = not applicable Another stability study was conducted to investigate the effect of storing methylnaltrexone bromide in an "ultra low" tungsten syringe (Becton Dickenson) for the formation of RRT 0.60 (1 mL BD Syringe, Type 1 borosilicate glass with stainless steel needle 29G×½ inch, (ultra low tungsten), BD Stopper 11510, West 4023/50 grey bromobutyl rubber, Coating: contact side with Daikyo Fluro Tec, remaining part with B2-40 coating. BD Rigid Needle Shield, with thermoplastic elastomer (TPE) needle shield and polypropylene rigid shield cover). The results of this study show that no RRT 0.60 compound formed at a level of 25 ppm or greater after 6 months at 40° C. and 75% relative humidity or 9 months at 25° C. and 60% relative humidity. These results are shown in Table 3, below.

TABLE 3

Amount of RRT 0.60 (ppm) in Ultra Low Tungsten Syringes*

| Conditions | MNTX | $T_0$ | 1 mo | 3 mo | 6 mo | 9 mo | 12 mo |
|---|---|---|---|---|---|---|---|
| 25° C./60% RH | 8 mg | <7 | <7 | <7 | <7 | 7 | 14 |
| 30° C./75% RH | 8 mg | <7 | <7 | 9 | <7 | 11 | 20 |
| 40° C./75% RH | 8 mg | <7 | <7 | 14 | 14 | NA | NA |

*All values reported in ppm, acquired by the 310 nm HPLC method.
LOQ = 7 ppm
NA = not applicable Example 6

X-Ray Diffraction Study of Compound II-1 Polymorph

The powder XRD analysis of compound II-1 polymorph, prepared according to Example 2, Method A, was performed on a X'PERT-MPD Powder X-ray Diffractometer.

The samples were ground to a fine powder and packed into a cavity style sample holder with a zero background plate. The peak positions characterized by powder X-ray diffraction of angle position (2θ) are as depicted in FIG. 15. In certain embodiments, the present invention provides a crystalline form of compound II-1 characterized in that said form has a powder X-ray diffraction pattern substantially similar to that depicted in FIG. 15.

Example 7

HPLC Method

As described herein, detection and quantification of potential impurities of methylnaltrexone bromide is an important, and regulated, aspect of drug quality and purity. Another aspect of the invention provides an analytical method useful for detecting Impurity A, also referred to herein as the RRT 0.60 degradant, impurity, or compound and also as compound II-1, at levels required by regulatory standards. In certain embodiments, the analytical method is capable of detecting Impurity A at a level of about 2.5 ppm in a sample of N-methylnaltrexone bromide. In some embodiments, the analytical method is capable of detecting Impurity A at a level of less than about 25, about 100, about 125, about 150, about 185, about 187, or about 190 ppm in a sample of N-methylnaltrexone bromide. In certain embodiments, such an analytical method is as follows:
 Column: Prodigy ODS (3) 15 cm×4.6 mm, 3 μm particles;
 Flow rate: 1.0 mL/min;
 Detection: 310 nm UV;
 Column Temperature: 37° C.;
 Autosampler Temperature: 5° C.;
 Sample Solvent: pH 5.0 Sodium Acetate buffer with EDTA (prepared from dissolving about 238 g NaOAc in 3 L of water. Add 45 mL glacial acetic acid and dilute to 50 L with water);

Mobile Phase A=950 mL/50 mL/1 mL Water/Methanol/TFA;
Mobile Phase B=500 mL/500 mL/1 mL Water/Methanol/TFA;
Gradient Program:

| Time (Min) | % Mobile Phase A | % Mobile Phase B |
|---|---|---|
| 0 | 93 | 7 |
| 20 | 73 | 27 |
| 20.1 | 0 | 100 |
| 25 | 0 | 100 |
| 25.1 | 93 | 7 |

Preparation of a standard sample of N-methylnaltrexone bromide, at a concentration of 0.0004 mg/mL, is performed as follows: 20 mg of N-methylnaltrexone bromide is weighed into two separate 100.0 mL volumetric flasks. 50 mL of sample solvent is added to dissolve the N-methylnaltrexone bromide and the resulting solution is diluted to volume with sample solvent. 2.0 mL of the resulting solution are pipetted into the second 100 mL volumetric flask which is then diluted to volume with sample solvent.

The amount of compound II-1 present in a sample of (R)—N-methylnaltrexone bromide is calculated using the following equation:

$$\text{Compound II} - 1(\text{ppm}) = \frac{(Ai)(Cr)(V)(RF)(1000000)}{(Ar)(Ws)}$$

where:
Ai=Area of impurity peak from the sample chromatogram;
Cr=Concentration of (R)—N-methylnaltrexone bromide in the standard preparation (mg/mL);
V=Volume of the sample solution (mL);
RF=Response Factor correction for compound II-1;
1000000=Conversion factor (ppm);
Ar=Average area of (R)—N-methylnaltrexone bromide from the standard chromatogram;
Ws=Sample weight of (R)—N-methylnaltrexone bromide (mg).

Example 8

Levels of tungsten, or derivatives thereof, may be measured by any technique including the method described in US 20080103438. Levels of tungsten, or derivatives thereof, in empty syringes can be determined by extraction followed by ICP-MS analysis. Such extraction and analytical methods are known to one of ordinary skill in the art and include those described in EPA Methods 6020A and 200.8, the entirety of which is hereby incorporated herein by reference.

Different techniques may provide different results depending on how aggressively the tungsten or derivatives thereof is removed from the glass medical container for testing (i.e., more aggressive techniques, such as with acids, remove higher levels of tungsten residue). For example, a glass medical container can be washed, i.e., extracted, with an acid-containing solution and the extract measured for tungsten such as described in Wang, et al., Journal of Pharmaceutical and Biomedical Analysis, 19 (1999) 937-943, "Determination of Tungsten in Bulk Drug Substance and Intermediates by ICP-AES and ICP-MS", which is incorporated herein by reference in its entirety. Similar methodology can be used for measuring tungsten-containing residue levels.

The following method is a general method that may be used to determine the amount of tungsten present in an empty syringe:

1. filling a glass medical container (e.g., empty syringe) with purified water (e.g., prepared by laboratory purification system, Millipore Milli Ro 4) and sealing the glass medical container (e.g., with a tip cap);
2. placing the filled glass medical container into an ultrasonic bath containing water at ambient temperature for 60 minutes;
3. removing the glass medical container and dispensing the contained solution into a sample vessel; and
4. measuring the concentration of the tungsten in the solution by Inductively Coupled Plasma Mass Spectrometry (ICP/MS).

Example 9

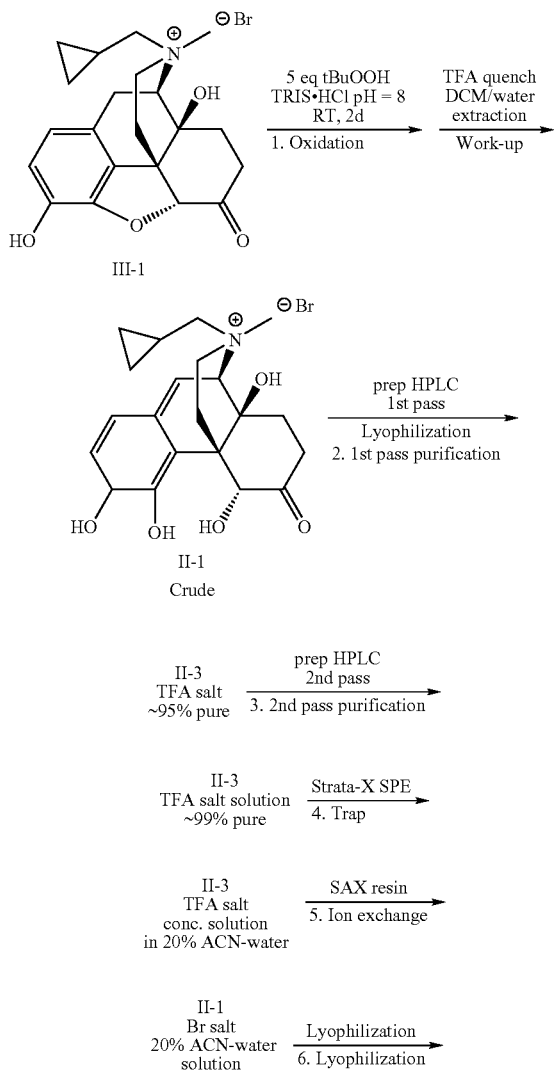

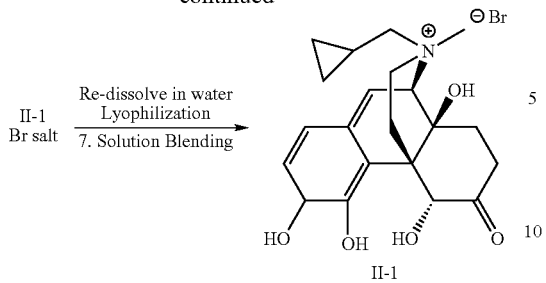

II-1
Br salt
Re-dissolve in water
Lyophilization
7. Solution Blending

II-1

According to the general scheme above, a solution of compound III-1 was dissolved in 1M TRIS pH 8 buffer and t-butyl hydroperoxide (5 molar equivalents) was added and the resulting mixture stirred at room temperature for two days. The reaction was stopped by addition of TFA and the solution was extracted with dichromomethane. The aqueous phase was separated and concentrated for HPLC injections. Preparative HPLC purification was performed on a Sunfire column (50×250 mm, C18, 5 μm from Waters) at flow rate of 50 mL/min with a mobile phase that started at 5% ACN/0.1% TFA and was changed to a gradient of 10% ACN/0.1% TFA over 30 min. The collected fractions were lyophilized and subjected to a second pass purification at the same condition as the first pass. The pooled fraction were applied on a reverse phase SPE (solid phase extraction) tube (Strata-X from Phenomenex) which was placed under vacuum to remove all remaining liquid. Then 20% acetonitrile/water was used to elute the compound, which was then passed through a strong anion exchange SPE tube (Strata-SAX from Phenomenex) pretreated with sodium bromide. The collected solution was lyophilized to afford compound II-1 as a red powder.

More specifically, 100 g N-(cyclopropylmethyl)-noroxymorphone methobromide (III-1) was charged into a magnetically stirred 2 l flask with thermocouple followed by the addition of 600 ml tris(hydroxymethyl)aminoethane. The slurry was then charged with 180 ml 70% t-butyl hydroperoxide (5 equivalents), at which time the slurry becomes solution and gradually darkens in color. The solution was stirred for 69 hours at ambient temperature and was measured at 62-67% conversion by HPLC. The solution was then charged with 20 ml trifluoroacetic acid to pH 2 and was washed with 800 ml methylene chloride. The layers were separated and again the aqueous was washed with 200 ml methylene chloride. The waste organic fractions were combined and back extracted with 2×200 ml water. All aqueous fractions were then combined to wash with 2×400 ml of fresh methylene chloride. The layers were then separated and the aqueous portion (~1.1 L) containing compound II-3 was isolated (yield unknown) and stored at −20 C to await the purification step. The analytical method utilized to assess % conversion was as follows:

Analytical Method for Crude Aqueous Product
Agilent 1100 HPLC
column: 4.6 mm×150 mm Sunfire C18
λ280 nm
flow rate: 1 ml/min
Gradient:

| Time | % A water w/0.1% TFA | % B acetonitrile w/0.1% TFA |
|---|---|---|
| 0 | 95 | 5 |
| 10 | 85 | 15 |
| 12 | 5 | 95 |
| 15 | 5 | 95 |
| 16 | 95 | 5 |
| 20 | 95 | 5 |

The crude compound II-3 was purified by preparatory HPLC using the following method.
Varian PrepStar pumps with Varian Prostar 320 Detector
column: 50 mm×250 mm Sunfire C18 5 micron
λ260 nm
flow rate: 50 ml/min
Gradient

| Time | % A water w/0.1% TFA | % B acetonitrile w/0.1% TFA |
|---|---|---|
| 0 | 95 | 5 (flow rate = 0) |
| 1 | 95 | 5 (flow rate = 50 ml/min) |
| 31 | 90 | 10 |
| 35 | 10 | 90 |
| 40 | 10 | 90 |
| 42 | 95 | 5 |
| 47 | 95 | 5 |
| 48 | 95 | 5 (flow rate = 0) |

The first pass preparatory HPLC purification was done by injecting 100 ml per injection and collecting 50 ml fractions with the use of an automated fraction collector. Typically, fractions 15-22 were collected, combined and lyophilized.

The second pass preparatory HPLC purification was done by loading the collected crude TFA salt material (crude II-3), about 2 g each, diluted with 20 ml water, back to the prep column with same gradient and buffer system. Fractions 23-29 were typically collected and combined. This combined fraction was then diluted 1:1 with water, split into 4 equal volumes and then applied onto 4 Strata-X SPE Giga Tube (60 ml, reverse phase resin trap) which have been prepared with following procedure:

Flush procedure for reverse phase column (Strata X 33 micron);
Elute 3 bed volumes of acetonitrile followed by 3 bed volumes of water; and
The tube was vacuum dried for 5 min before the desired fraction was eluted by 20% ACN-water and collected (~20 ml×4).

The combined solution was split into 4 equal volume and applied onto 4 Strata SAX SPE Giga Tube (60 ml, strong anion exchange resin) which were prepared with the following procedure:

Flush procedure for ion exchange column Strata SAX 55 micron; and
Elute 3 bed volumes of acetonitrile followed by 3 bed volumes of 1M sodium bromide followed by 5 bed volumes of water.

The desired fraction was collected and the tube was washed by 20% ACN-water until no colored solution was eluted. A total of ~45 ml×4 was collected, pooled and lyophilized.

The multi-lots of lyophilized material were re-dissolved in water (~16 g in 150 ml of water) and lyophilized to afford 15.9 g of II-1 as a dark red fluffy solid.

While we have described a number of embodiments of this invention, it is apparent that our basic examples may be altered to provide other embodiments that utilize the compounds and methods of this invention. Therefore, it will be appreciated that the scope of this invention is to be defined by

We claim:
1. A prefilled syringe comprising a liquid composition comprising a compound of formula III:

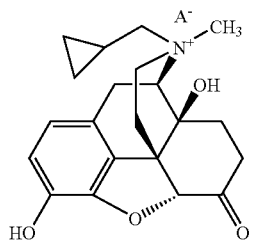

wherein A⁻ is a suitable anion;
wherein the prefilled syringe is substantially free of tungsten; and
wherein the liquid composition comprises less than about 190 ppm of a compound of formula II:

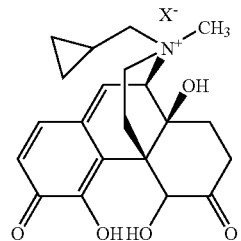

wherein X⁻ is a suitable anion.

2. The prefilled syringe according to claim 1, wherein the liquid composition comprises less than about 190 ppm total of the compound of formula II and a compound of formula IV:

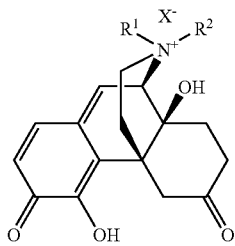

wherein:
R¹ and R² are each independently $C_{1-6}$ aliphatic; and
X⁻ is a suitable anion.

3. A prefilled syringe comprising a liquid composition comprising a compound of formula III-1:

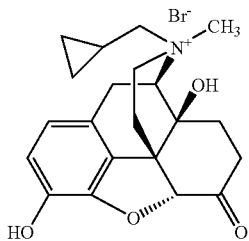

wherein the liquid composition comprises less than about 190 ppm of a compound of formula II-1:

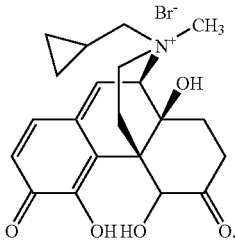

4. The prefilled syringe according to claim 3, comprising less than about 190 ppm total of compound II-1 and compound IV-1:

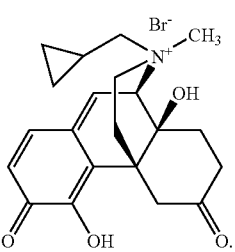

5. The prefilled syringe according to claim 1, comprising 8 mg of compound III-1:

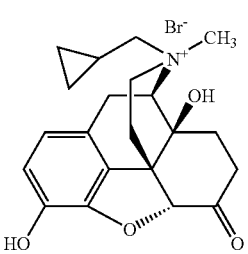

in 0.4 mL water, and compound II-1:

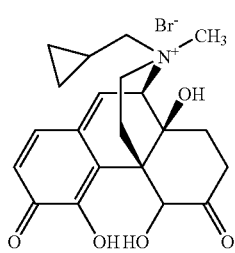

wherein compound II-1 is present in an amount of less than about 190 ppm.

6. The prefilled syringe according to claim 5, wherein the liquid composition further comprises 2.6 mg sodium chloride, 0.16 mg edetate calcium disodium, and 0.12 mg glycine hydrochloride.

7. The prefilled syringe according to claim 1, comprising 12 mg of compound III-1:

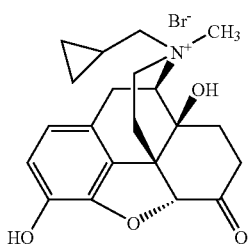

in 0.6 mL water, and compound II-1:

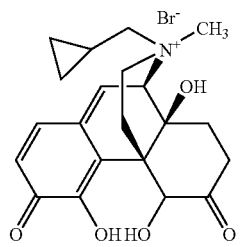

wherein compound II-1 is present in an amount of less than about 190 ppm.

8. The prefilled syringe according to claim 7, wherein the liquid composition further comprises 3.9 mg sodium chloride, 0.24 mg edetate calcium disodium, and 0.18 mg glycine hydrochloride.

9. A method comprising the steps of:
(i) providing a prefilled syringe, substantially free from tungsten, comprising a unit dosage of a liquid composition comprising 8 mg or 12 mg of compound III-1:

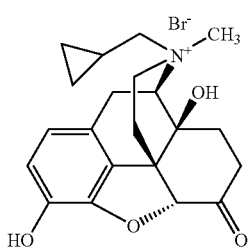

in 0.4 mL or 0.6 mL water, and compound II-1:

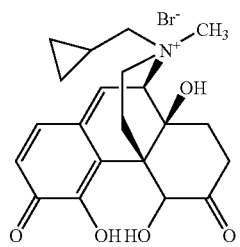

wherein compound II-1 is present in an amount of less than about 190 ppm; and
(ii) administering the unit dosage to a subject via subcutaneous injection.

10. The method according to claim 9, wherein the subject is suffering from opioid induced constipation.

11. The method according to claim 9, wherein the tungsten is present in an amount of less than 50 parts per billion.

12. The method according to claim 11, wherein the tungsten is present in an amount of less than 12 parts per billion.

13. The method according to claim 9, wherein the liquid composition further comprises edetate calcium disodium and glycine hydrochloride.

14. The prefilled syringe of claim 3, wherein the prefilled syringe is substantially free of tungsten.

15. The prefilled syringe of claim 1, wherein the liquid composition comprises less than about 187 ppm of the compound of formula II.

16. The prefilled syringe of claim 15, wherein the liquid composition comprises less than about 185 ppm of the compound of formula II.

17. The prefilled syringe of claim 15, wherein the liquid composition comprises less than about 150 ppm of the compound of formula II.

18. The prefilled syringe of claim 15, wherein the liquid composition comprises less than about 125 ppm of the compound of formula II.

19. The prefilled syringe of claim 15, wherein the liquid composition comprises less than about 100 ppm of the compound of formula II.

20. The prefilled syringe of claim 15, wherein the liquid composition comprises less than about 25 ppm of the compound of formula II.

21. The prefilled syringe of claim 2, wherein the liquid composition comprises less than about 187 ppm total of the compound of formula II and the compound of formula IV.

22. The prefilled syringe of claim 21, wherein the liquid composition comprises less than about 185 ppm total of the compound of formula II and the compound of formula IV.

23. The prefilled syringe of claim 21, wherein the liquid composition comprises less than about 150 ppm total of the compound of formula II and the compound of formula IV.

24. The prefilled syringe of claim 21, wherein the liquid composition comprises less than about 125 ppm total of the compound of formula II and the compound of formula IV.

25. The prefilled syringe of claim 21, wherein the liquid composition comprises less than about 100 ppm total of the compound of formula II and the compound of formula IV.

26. The prefilled syringe of claim 21, wherein the liquid composition comprises less than about 25 ppm total of the compound of formula II and the compound of formula IV.

27. The prefilled syringe of claim 3, wherein the liquid composition comprises less than about 187 ppm of the compound of formula II-1.

28. The prefilled syringe of claim 27, wherein the liquid composition comprises less than about 185 ppm of the compound of formula II-1.

29. The prefilled syringe of claim 27, wherein the liquid composition comprises less than about 150 ppm of the compound of formula II-1.

30. The prefilled syringe of claim 27, wherein the liquid composition comprises less than about 125 ppm of the compound of formula II-1.

31. The prefilled syringe of claim 27, wherein the liquid composition comprises less than about 100 ppm of the compound of formula II-1.

32. The prefilled syringe of claim 27, wherein the liquid composition comprises less than about 25 ppm of the compound of formula II-1.

33. The prefilled syringe of claim 4, comprising less than about 187 ppm total of the compound of formula II-1 and the compound of formula IV-1.

34. The prefilled syringe of claim 33, comprising less than about 185 ppm total of the compound of formula II-1 and the compound of formula IV-1.

35. The prefilled syringe of claim 33, comprising less than about 150 ppm total of the compound of formula II-1 and the compound of formula IV-1.

36. The prefilled syringe of claim 33, comprising less than about 125 ppm total of the compound of formula II-1 and the compound of formula IV-1.

37. The prefilled syringe of claim 33, comprising less than about 100 ppm total of the compound of formula II-1 and the compound of formula IV-1.

38. The prefilled syringe of claim 33, comprising less than about 25 ppm total of the compound of formula II-1 and the compound of formula IV-1.

39. The prefilled syringe of claim 5 or 7, wherein compound II-1 is present in an amount of less than 187 ppm.

40. The prefilled syringe of claim 39, wherein compound II-1 is present in an amount of less than 185 ppm.

41. The prefilled syringe of claim 39, wherein compound II-1 is present in an amount of less than 150 ppm.

42. The prefilled syringe of claim 39, wherein compound II-1 is present in an amount of less than 125 ppm.

43. The prefilled syringe of claim 39, wherein compound II-1 is present in an amount of less than 100 ppm.

44. The prefilled syringe of claim 39, wherein compound II-1 is present in an amount of less than 25 ppm.

45. The method of claim 9, wherein compound II-1 is present in an amount of less than 187 ppm.

46. The method of claim 45, wherein compound II-1 is present in an amount of less than 185 ppm.

47. The method of claim 45, wherein compound II-1 is present in an amount of less than 150 ppm.

48. The method of claim 45, wherein compound II-1 is present in an amount of less than 125 ppm.

49. The method of claim 45, wherein compound II-1 is present in an amount of less than 100 ppm.

50. The method of claim 45, wherein compound II-1 is present in an amount of less than 25 ppm.

* * * * *